United States Patent
Wu et al.

(10) Patent No.: US 9,701,725 B2
(45) Date of Patent: Jul. 11, 2017

(54) ANTI-CANCER DNA VACCINE EMPLOYING PLASMIDS ENCODING SIGNAL SEQUENCE, MUTANT ONCOPROTEIN ANTIGEN, AND HEAT SHOCK PROTEIN

(75) Inventors: Tzyy-Choou Wu, Stevenson, MD (US); Chien-Fu Hung, Timonium, MD (US)

(73) Assignee: The Johns Hopkins University, Baltimore, MD (US)

( * ) Notice: Subject to any disclaimer, the term of this patent is extended or adjusted under 35 U.S.C. 154(b) by 2039 days.

(21) Appl. No.: 10/555,669

(22) PCT Filed: May 5, 2004

(86) PCT No.: PCT/US2004/013756
§ 371 (c)(1),
(2), (4) Date: Dec. 5, 2008

(87) PCT Pub. No.: WO2004/098526
PCT Pub. Date: Nov. 18, 2004

(65) Prior Publication Data
US 2010/0278871 A1    Nov. 4, 2010

Related U.S. Application Data

(60) Provisional application No. 60/467,602, filed on May 5, 2003.

(51) Int. Cl.
*C07K 14/35* (2006.01)
*A61K 39/12* (2006.01)
*A61K 39/00* (2006.01)

(52) U.S. Cl.
CPC .......... *C07K 14/35* (2013.01); *A61K 39/0011* (2013.01); *A61K 39/12* (2013.01); *A61K 2039/53* (2013.01); *A61K 2039/54* (2013.01); *A61K 2039/55516* (2013.01); *A61K 2039/585* (2013.01); *A61K 2039/6043* (2013.01); *C07K 2319/02* (2013.01); *C12N 2710/20022* (2013.01); *C12N 2710/20034* (2013.01)

(58) Field of Classification Search
None
See application file for complete search history.

(56) References Cited

U.S. PATENT DOCUMENTS

| | | |
|---|---|---|
| 4,898,730 A | 2/1990 | Levy et al. |
| 5,217,879 A | 6/1993 | Huang et al. |
| 5,328,984 A | 7/1994 | Pastan et al. |
| 5,348,945 A | 9/1994 | Berberian et al. |
| 5,426,097 A | 6/1995 | Stern et al. |
| 5,503,829 A | 4/1996 | Ladant et al. |
| 5,547,846 A | 8/1996 | Bartsch et al. |
| 5,582,831 A | 12/1996 | Shinitzky |
| 5,591,716 A | 1/1997 | Siebert et al. |
| 5,618,536 A | 4/1997 | Lowy et al. |
| 5,629,161 A | 5/1997 | Muller et al. |
| 5,674,486 A | 10/1997 | Sobol et al. |
| 5,744,133 A | 4/1998 | Lathe et al. |
| 5,750,119 A | 5/1998 | Srivastava |
| 5,821,088 A | 10/1998 | Darzins et al. |
| 5,830,464 A | 11/1998 | Srivastava |
| 5,834,309 A | 11/1998 | Thompson et al. |
| 5,837,251 A | 11/1998 | Srivastava |
| 5,844,089 A | 12/1998 | Hoffman et al. |
| 5,854,202 A | 12/1998 | Dedhar |
| 5,855,891 A | 1/1999 | Lowy et al. |
| 5,935,576 A | 8/1999 | Srivastava |
| 5,948,646 A | 9/1999 | Srivastava |
| 5,951,975 A | 9/1999 | Falo, Jr. et al. |
| 5,962,318 A | 10/1999 | Rooney et al. |
| 5,997,869 A | 12/1999 | Goletz et al. |
| 6,007,821 A | 12/1999 | Srivastava et al. |
| 6,013,262 A | 1/2000 | Frazer et al. |
| 6,017,544 A | 1/2000 | Srivastava |
| 6,017,735 A | 1/2000 | O'Hare et al. |
| 6,020,309 A | 2/2000 | Campo et al. |
| 6,030,618 A | 2/2000 | Srivastava |
| 6,046,158 A | 4/2000 | Ariizumi et al. |
| 6,066,716 A | 5/2000 | Wallen et al. |
| 6,235,523 B1 | 5/2001 | Gajewczyk et al. |
| 6,296,843 B1 | 10/2001 | Debinski |
| 6,331,388 B1 | 12/2001 | Malkovsky et al. |
| 6,399,070 B1 | 6/2002 | Srivastava et al. |
| 6,403,080 B1 | 6/2002 | Segal |
| 6,410,027 B1 | 6/2002 | Srivastava |
| 6,410,028 B1 | 6/2002 | Srivastava |
| 6,524,825 B1 | 2/2003 | Mizzen et al. |

(Continued)

FOREIGN PATENT DOCUMENTS

| CA | 2413543 | 1/2002 |
|---|---|---|
| EP | 0451550 A2 | 10/1991 |

(Continued)

OTHER PUBLICATIONS

Genbank Accession # NP_214864, dnaK [*Mycobacterium tuberculosis* H37Rv], Sep. 7, 2001.*
Edmonds and Vousden, A point mutational analysis of Human Papillomavirus Type 16 E7 Protein, 1989, Journal of Virology, vol. 63, No. 6, pp. 2650-2656.*
Wei-Hsu Chen, et al., "Modulatory Effects of the Human Heat Shock Protein 70 on DNA Vaccination," J Biomed Sci 2000, pp. 412-418.
Aguiar et al., "Enhancement of the immune response in rabbits to a malaria DNA vaccine by immunization with a needle-free jet device," Vaccine, 20:275-280 (2001).
Alexander et al., "Development of High Potency Universal DR-Restricted Helper Epitopes by Modification of High Affinity DR-Blocking Peptides," Immunity, 1:751-761 (1994).

(Continued)

*Primary Examiner* — Benjamin P Blumel
(74) *Attorney, Agent, or Firm* — Foley Hoag LLP

(57) ABSTRACT

Novel nucleic acid vectors comprising sequences encoding (a) an antigen, (b) a signal peptide, and (c) a heat shock protein, are disclosed, as are methods for using such vectors to induce antigen-specific immune responses and to treat tumors.

16 Claims, 5 Drawing Sheets

(56) References Cited

U.S. PATENT DOCUMENTS

| | | | |
|---|---|---|---|
| 6,541,010 B1 | 4/2003 | Johnston et al. | |
| 6,734,173 B1 | 5/2004 | Wu et al. | |
| 7,001,995 B1 | 2/2006 | Neeper et al. | |
| 7,153,931 B1 | 12/2006 | Fischer et al. | |
| 7,318,928 B2 | 1/2008 | Wu et al. | |
| 7,342,002 B2 | 3/2008 | Wu et al. | |
| 2001/0034042 A1 | 10/2001 | Srivastava | |
| 2002/0064771 A1 | 5/2002 | Zhong et al. | |
| 2002/0091246 A1 | 7/2002 | Pardoll et al. | |
| 2002/0110566 A1* | 8/2002 | Neefe et al. | 424/204.1 |
| 2002/0164338 A1 | 11/2002 | Iversen | |
| 2002/0182586 A1 | 12/2002 | Morris et al. | |
| 2003/0229202 A1 | 12/2003 | Guo et al. | |
| 2004/0028693 A1 | 2/2004 | Wu et al. | |
| 2004/0086845 A1 | 5/2004 | Wu et al. | |
| 2004/0106128 A1 | 6/2004 | Majumdar et al. | |
| 2004/0259247 A1 | 12/2004 | Tuschl et al. | |
| 2005/0048467 A1 | 3/2005 | Sastry et al. | |
| 2005/0054820 A1 | 3/2005 | Wu et al. | |
| 2005/0277605 A1 | 12/2005 | Wu et al. | |
| 2006/0051354 A1 | 3/2006 | Simard et al. | |
| 2006/0189556 A1 | 8/2006 | Yu et al. | |
| 2006/0258584 A1 | 11/2006 | Lind et al. | |
| 2007/0026076 A1 | 2/2007 | Wu et al. | |
| 2013/0331546 A1 | 12/2013 | Ohlfest et al. | |

FOREIGN PATENT DOCUMENTS

| | | |
|---|---|---|
| EP | 0 763 740 | 3/1997 |
| EP | 1363983 | 11/2001 |
| EP | 1222289 | 7/2002 |
| EP | 1363660 | 11/2003 |
| EP | 1644048 | 4/2006 |
| KR | 10-0835879 B1 | 6/2008 |
| KR | 10-2013-0012936 | 2/2013 |
| KR | 10-2014-0138507 | 12/2014 |
| WO | WO-89/12455 | 12/1989 |
| WO | WO-92/05248 | 4/1992 |
| WO | WO-93/20844 | 10/1993 |
| WO | WO-94/04696 | 3/1994 |
| WO | WO-94/29459 | 12/1994 |
| WO | WO-95/17212 | 6/1995 |
| WO | WO-96/36643 | 11/1996 |
| WO | WO-97/03703 | 2/1997 |
| WO | WO-97/06685 | 2/1997 |
| WO | WO-97/41440 | 11/1997 |
| WO | WO-98/20135 | 5/1998 |
| WO | WO-98/23735 | 6/1998 |
| WO | WO-98/32866 | 7/1998 |
| WO | WO-98/48003 | 10/1998 |
| WO | WO-99/07860 | 2/1999 |
| WO | WO-99/07869 | 2/1999 |
| WO | WO-99/42121 | 8/1999 |
| WO | WO-99/42472 | 8/1999 |
| WO | WO-99/58658 | 11/1999 |
| WO | WO-99/65940 | 12/1999 |
| WO | WO-01/029233 | 4/2001 |
| WO | WO-02/012281 | 2/2002 |
| WO | WO-02/061113 | 8/2002 |
| WO | WO-02/074920 | 9/2002 |
| WO | WO-02/009645 | 1/2003 |
| WO | WO-03/008543 | 1/2003 |
| WO | WO-03/010235 | 2/2003 |
| WO | WO-03/080111 | 10/2003 |
| WO | WO-03/083052 | 10/2003 |
| WO | WO-03/085085 | 10/2003 |
| WO | WO-2004/030636 | 4/2004 |
| WO | WO-2004/060304 | 7/2004 |
| WO | WO-2004/098526 | 11/2004 |
| WO | WO-2005/047501 | 5/2005 |
| WO | WO-2005/081716 | 9/2005 |
| WO | WO-2006/073970 | 7/2006 |
| WO | WO-2006/081323 | 8/2006 |
| WO | WO-2006/120474 | 11/2006 |
| WO | WO-2007/027751 | 3/2007 |
| WO | WO-2007/071997 | 6/2007 |
| WO | WO-2009/007336 | 1/2009 |
| WO | WO-2010/129339 A2 | 11/2010 |

OTHER PUBLICATIONS

Anonymous: "E7 vaccine (NSC 723254)," Timeless Success Story, Online, XP002394109 (2002).

Anthony et al., "Priming of CD8 CTL Effector Cells in Mice by Immunizationwith a Stress-Protein-Influenza Virus Nucleoprotein Fusion Molecule," Vaccine, 17(4):373-383 (1999).

Asea et al., "Novel Signal Transduction Pathway Utilized by Extracellular HSP70," Journal of Biological Chemistry, 277(7):15028-15034 (2002).

Ausbel, et al., Current Protocols in Molecular Biology, John Wiley & Sons, 1989.

Babiuk et al., "Immunization of animals: from DNA to the dinner plate," Veterinary Immunology and Immunopathology, 72:189-202 (1999).

Bae et al., "Therapeutic Synergy of Human Papillomavirus E7 Subunit Vaccines plus Cisplatin in an Animal Tumor Model: Casual Involvement of Increased Sensitivity of Cisplatin-Treated Tumors to CTL-Mediated Killing in Therapeutic Synergy," Clin. Cancer Res., 13(1):341-349 (2007).

Banchereau, J., "Dendritic Cells: Therapeutic Potentials," Transfus Sci., 18(2):313-326 (1997).

Banu et al., "Modulation of Haematopoietic Progenitor Development by FLT-3 Ligand,"Cytokine, 11(9):679-688 (1999).

Barrios et al., "Mycobacterial heat-shock proteins as carrier molecules. II: The use of the 70-kDa mycobacterial heat-shock protein as carrier for conjugated vaccines can circumvent the need for adjuvants and Bacillus Calmette Guerin priming," Eur. J. Immunol., 22:1365-1372 (1992).

Basu et al., "Calreticulin, A Peptide-Binding Chaperone of the Endoplasmic Reticulum, Elicits Tumor- and Peptide-Specific Immunity," Journal of Experimental Medicine, 189(5):797-802 (1999).

Becker et al., "CD40, an extracellular receptor for binding and uptake of Hsp70-peptide complexes," Journal of Cell Biology, 158(7):1277-1285 (2002).

Beissbarth et al., "Increased efficiency of folding and peptide loading of mutant MHC class I molecules," Eur. J. Immunol., 30:1203-1213 (2000).

Bennett et al., "Calnexin Association Is Not Sufficient to Protect T Cell Receptor α Proteins from Rapid Degradation in CD4+CD8+ Thymocytes," The Journal of Biological Chemistry 273(37):23674-23680 (1998).

Benton et al., "DNA Vaccine Strategies for the Treatment of Cancer," Curr Top Microbiol Immunol., 226:1-20 (1998).

Bhoola et al., "Diagnosis and management of epithelial ovarian cancer," Obstet. Gynecol., 107(6):1399-1410 (2006).

Biragyn et al., "Genetic fusion of chemokines to a self tumor antigen induces protective, T-Cell dependent antitumor immunity," Nature Biotechnology, 17:253-258 (1993) Abstract.

Blachere et al., "Heat shock Protein-peptide complexes, Reconstituted in vitro, Elicit Peptide-specific cytotoxic T Lymphocyte Response and Tumor Immunity," J. Exp. Med., 186(8):1315-1322 (1997).

Blachere et al. "Heat shock proteins against cancer," J. of Immunotherapy Emphasis Tumor Immunol., 14:352-356 (1993).

Bohm et al., "Routes of plasmid DNA vaccination that prime murine humoral and cellular immune responses," Vaccine, 16:949-954 (1998).

Boyle et al. "Enhanced responses to a DNA vaccine encoding a fusion antigen that is directed to sites of immune induction," Nature, 392:408-411 (1998).

Bredenbeek et al., "Sindbis Virus Expression Vectors: Packaging of RNA Replicons by Using Defective Helper RNAs," Journal of Virology, 67(11):6439-6446 (1993).

Breitburd et al., "Human papillomavirus vaccines," Cancer Biology, 9:431-445 (1999).

(56) References Cited

OTHER PUBLICATIONS

Brossart et al., "Identification of HLA-A2-Restricted T-Cell Epitopes Derived From the MUC1 Tumor Antigen for Broadly Applicable Vaccine Therapies," Blood, 93(12):4309-4317 (1999).
Buck et al., "Efficient Intracellular Assembly of Papillomaviral Vectors," Journal of Virology, 78(2):751-757 (2004).
Bueler et al., "Induction of Antigen-Specific Tumor Immunity by Genetic and Cellular Vaccines against MACE: Enhanced Tumor Protection by Coexpression of Granulocyte-Macrophage Colony-Stimulating Factor and B7-1," Molecular Medicine, 2(5):545-555 (1996).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, 111:2129-2138 (1990).
Carbonetti et al., "Intracellular Delivery of a Cytolytic T-Lymphocyte Epitope Peptide by Pertussis Toxin to Major Histocompatibioity Complex Class I without Involvement of the Cytosolic Class I Antigen Processing Pathway," Infection and Immunity 67(2):602-607 (1999).
Cavill et al., "Generation of a Monoclonal Antibody Against Human Calreticulin by Immunization with a Recombinant Calreticulin Fusion Protein: Application in Paraffin-Embedded Sections," Appl. Immunohistochemistry & Molecular Morphology 7(2):150-155 (1999).
Celluzzi et al., "Peptide-pulsed Dendritic Cells Induce Antigen-specific, CTL-mediated Protective Tumor Immunity," J. Exp. Med. 183:283-287 (1996).
Chang et al., "Cancer Immunotherapy Using Irradiated Tumor Cells Secreting Heat Shock Protein 70," Cancer Res., 67(20):10047-10057 (2007).
Chang, C-L. et al., "Control of human mesothelin-expressing tumors by DNA vaccines." Gene Therapy 1-10 (2007).
Chavin, K. et al., "Obesity Induces Expression of Uncoupling Protein-2 in Hepatocytes and Promotes Liver ATP Depletion." J. Biol. Chem. 274(9):5692-5700 (1999).
Chen, C-H. et al., "Antigen-specific immunotherapy for human papillomavirus 16 E7-expressing tumors grown in the liver." Journal of Hepatology 33:91-98 (2000).
Chen, C-H. et al., "Boosting with recombinant vaccinia increases HPV-16 E7-specific T cell precursor frequencies of HPV-16 E7-expressing DNA vaccines," Vaccine, 18:2015-2022 (2000).
Chen et al., Design of a genetic immunotoxin to eliminate toxin immunogenicity, Gene Therapy, 2:116-123 (1992).
Chen, C-H et al., "Enhancement of DNA Vaccine Potency by Linkage of Antigen Gene to an HSP70 Gene," Cancer Research, 60(4):1035-1042 (2000).
Chen, C-H. et al., "Gene gun-mediated DNA vaccination induces antitumor immunity against human papillomavirus type 16 E7-expressing murine tumor metastases in the liver and lungs." Gene Therapy, 6:1972-1981 (1999).
Chen et al., "Human pappillomavirus type 16 nucleoprotein E7 is a tumor rejection antigen," PNAS, 88:110-114 (1991).
Chen et al., "Induction of Cytotoxic T Lymphocytes Specific for a Syngeneic Tumor Expressing the E6 Oncoprotein of Human Papillomavirus Type 16," Journal of Immunology, 148:2617-2621 (1992).
Chen et al., "Mycobacterial heat shock protein 65 enhances antigen cross-presentation in dendritic cells independent of Toll-like receptor 4 signaling," Journal of Leukocyte Biology, 75:260-266 (2004).
Chen, C-H. et al. "Recombinant DNA vaccines protect against tumors that are resistant to recombinant vaccinia vaccines containing the same gene." Gene Therapy, 8:128-138 (2001).
Cheng et al., "Bax-independent inhibition of apoptosis by Bcl-$x_L$," Nature, 379(8):554-556 (1996).
Cheng, W-F. et al., "CD8+ T cells, NK cells and IFN-$\gamma$ are important for control of tumor with downregulated MHC class I expression by DNA vaccination." Gene Therapy 10:1311-1320, (2003).

Cheng, W-F. et al., "Cancer Immunotherapy Using Sindbis Virus Replicon Particles Encoding a VP22-Antigen Fusion." Human Gene Therapy. 13:553-568 (2002).
Cheng, W.-F., et al., "Characterization of DNA Vaccines Encoding the Domains of Calreticulin for Their Ability to Elicit Tumor-Specific Immunity and Antiangiogenesis," Vaccine, 23(29):3864-3874 (2005).
Cheng, W-F. et al. "Enhancement of Sindbis Virus Self-Replicating RNA Vaccine Potency by Linkage of Herpes Simplex Virus Type 1 VP22 Protein to Antigen." Journal of Virology, 75(5): 2368-2376 (2001).
Cheng, W-F. et al. "Enhancement of Sindbis Virus Self-Replicating RNA Vaccine Potency by Linkage of *Mycobacterium tuberculosis* Heat Shock Protein 70 Gene to an Antigen Gene." Journal of Immunology, 166:6218-6226 (2001).
Cheng, W-F. et al., "Enhancement of Sindbis Virus Self-Replicating RNA Vaccine Potency by Targeting Antigen to Endosomal/Lysosomal Compartments." Human Gene Therapy 12:235-252 (2001).
Cheng, W-F. et al., "Repeated DNA Vaccinations Elicited Qualitatively Different Cytotoxic T Lymphocytes and Improved Protective Antitumor Effects." J Biomed Sci 9:675-687 (2002).
Cheng et al. (Report on Results of Monographic Study # NSC91-2314-B-002-377, National Taiwan University, National Scientific Committee, available to public Oct. 31, 2003).
Cheng, W-F. et al., "Tumor-specific immunity and antiangiogenesis generated by a DNA vaccine encoding calreticulin linked to a tumor antigen." J. Clin. Invest. 108:669-678 (2001).
Cho et al., "Enhanced cellular immunity to hepatitis C virus nonstructural proteins by codelivery of granulocyte macrophage-colony stimulating factor gene in intramuscular DNA immunization," Vaccine, 17:1136-1144 (1999).
Chow et al., "Development of Thi1 and Th2 Populations and the Nature of Immune Responses to Hepatitis B Virus DNA Vaccines Can Be Modulated by Codelivery of Various Cytokine Genes," The Journal of Immunology, 160(3):1320-1329 (1998).
Chu et al., "Cancer Immunotherapy Using Adjuvant-Free, Fusion Protein Encoding M. Golvis BCG HSP65 and HPV16 E7," FASEB Journal 12(5), Mar. 20, 1998 Abstract XP000960840.
Chu et al., Immunotherapy of a human papillomavirus (HPV) type 16 E7-expressing tumour by administration of fusion protein comprising *Mycobacterium bovis* bacille Calmette-Guerin (BGG) hsp65 and HPV 16 E7, Clin. Exp. Immunol., 121(2):216-225 (2000).
Ciupitu et al., "Immunization with a Lymphocytec Choriomeningitis Virus Peptide Mixed Heat Sbcok Protein 70 Results in Protective Antiviral Immunity and Specific Cytotoxic T Lymphocytes," J. Exp. Med., 187(5):685-691 (1998).
Corr et al., "Costimulation Provided by DNA Immunization Enhances Antitumor Immunity," The Journal of Immunology, 159(10):4999-5004 (1997).
Coukos et al., "Immunotherapy for gynaecological malignancies," Expert Opin. Biol. Ther., 5(9):1193-1210 (2005).
Crum et al., "Vaccines for Cervical Cancer," Cancer Journal from Scientific American, 9(5):368-376 (2003).
Davidoff et al., "Immune Response to P53 is Dependent upon P53/HSP70 Complexes in Breast Cancers," Proceedings of the National Academy of Sciences of USA, 89(8):3442 (1992).
Debinsky et al., "A Wide Range of Human Cancers Express Interleukin 4 (IL-4) Receptors That Can Be Targeted with Chimeric Toxin Composed of IL-4 and *Pseudomonas* Exotoxin," The Journal of Biological Chemistry, 268(19):14065-14070 (1993).
de Jong et al., "Enhancement of human papillomavirus (HPV) type 16 E6 and E7-specific T-cell immunity in healthy volunteers through vaccination with TA-CIN, an HPV16 L2E7E6 fusion protein vaccine," Vaccine, 20:3456-3464 (2002).
Devaraj, K. et al., "Development of HPV Vaccines for HPV-Associated Head and Neck Squamous Cell Carcinoma," Crit. Rev. Oral Biol. Med. 14(5):345-362, (2003).
Dialynas et al., "Characterization of the Murine T Cell Surface Molecule Designated L3T4, Identified by Monocolonal Antibody GK1.5: Similarity of L3T4 to the Human Leu-3/T4 Molecule," J. Immunol., 131(5):2445-2451 (1983).

(56) References Cited

OTHER PUBLICATIONS

Donnelly et al., "DNA Vaccines," Annual Review of Immunology, 15:617-48 (1997).
Donnelly et al., "DNA Vaccines: Progress and Challenges," J. Immunol., 175:633-639 (2005).
Donnelly et al., "Targeted delivery of peptide epitopes to class I major histocompatibility molecules by a modified *Pseudomonas* exotoxin," Proc. Natl. Acad. Sci. USA 90:3530-3534 (1993).
Drake et al., "Assessing tumor growth and distribution in a model of prostate cancer metastasis using bioluminescence imaging," Clin. Exp. Metastasis, 22:674-684 (2005).
Eggleton, P. and Llewellyn, D.H., "Pathophysiological Roles of Calreticulin in Autoimmune Disease," Scand. J. Immunol. 49:466-473 (1999).
Eiben et al., "Establishment of an HLA-a*0201 Human Papillovavrus Type 16 Tumor Model to Determine the Efficacy of Vaccination Strategies in HLA-A*0201 Transgenic Mice," Cancer Research, 62:5792-5799 (2002).
Eisenbraun et al., "Examination of parameters affecting the elicitation of humoral immune responses by particle bombardment-mediated genetic immunization," DNA Cell Biol., 12(9):791-797 (1993).
Elliott et al., "Intercellular trafficking and protein delivery by a herpesvirus structural protein," Cell, 88(2):223-233 (1997).
Elsaghier et al., "Localisation of Linear Epitopes at the Carboxy-Terminal End of the Mycobacterial 71 KDA Heat Shock Protein," Molecular Immunology 29(9):1153-1156 (1992).
Feltkamp et al., "Vaccination with cytotoxic T lymphocyte epitope-containing peptide protects against a tumor induced by human papillomavirus type 16-transformed cells," Eur. J. Immunol., 23(9):2242-2249 (1993).
Fernando et al., "Expression, purification and immunological characterization of the transforming protein E7, from cervical cancer-associated human papilloma virus type 16," Clin. Exp. Immunol., 115:397-403 (1999).
Flohe et al., "Human Heat Shock Protein 60 Induces Maturation of Dendritic Cells Versus a Th1-Promoting Phenotype," The Journal of Immunology, 170:2340-2348 (2003).
Fominaya et al., "Target Cell-specific DNA Transfer Mediated by a Chimeric Multidomain Protein," The Journal of Biological Chemistry, 271(18):10560-10568 (1996).
Fomsgaard et al., "Improved Humoral and Cellular Immune Responses Against the gp120 V3 Loop of HIV-1 Following Genetic Immunization with a Chimeric DNA Vaccine Encoding the V3 Inserted into the Hepatitis B Surface Antigen," Scand J. Immunol., 47(4):289-95 (1998).
Forni et al., "Cytokine gene-engineered vaccines," Curr. Opin. Mol. Ther. Feb;1(1):34-38 (Abstract) (1999).
Frydman et al., "Folding of nascent polypeptide chains in a high molecular mass assembly with molecular chaperones," Nature, 370:111-117 (1994).
Galloway, D.A., "Papillomavirus vaccines in clinical trials," Lancet Infect. Dis., 3(8):469-475 (2003).
Gao et al., "Immune response to human papillomavirus type 16 E6 gene in a live vaccinia vector," Journal of General Virology, 75:157-164 (1994).
Gavarasana et al., "Prevention of Carcinoma of Cervix with Human Papillomavirus Vaccine," Indian Journal of Cancer, 37:57-66 (2000).
Geissler et al., "Enhancement of Cellular and Humoral Immune Responses to Hepatitis C Virus Protein Using DNA Based Vaccines Augmented with Cytokine-Expressing Plasmids," The Journal of Immunology, 158(3):1231-1237 (1997).
Georgopoulos et al., "Role of the Major Heat Shock Proteins as Molecular Chaperones," Annu. Rev. Cell. Bio., 9:601-634 (1993).
Goletz et al., "Delivery of Antigens to the MHC Class I Pathway Using Bacterial Toxins," Human Immunology, 54:129-136 (1997).
Grandis et al., "Head and Neck Cancer: Meeting Summary and Research Opportunities," Cancer Research, 64:8126-8129 (2004).

Graner et al., "Immunoprotective Activities of Multiple Chaperone Proteins Isolated from Murine B-Cell Leukemia/Lymphoma," Clinical Cancer Research, 6:909-915 (2000).
Haas et al., "cDNA cloning of the immunoglobulin heavy chain binding protein," Proc. Natl. Acad. Sci. USA, 85:2250-2254 (1988).
Hannum et al., "Ligand for FLT3/FLK2 Receptor Tyrosine Kinase Regulates Growth of Haematopoietic Stem Cells and is Encoded by Variant RNAs," Nature 368:643-8 (1994).
Hansen et al., "Structural features of MHC class I molecules that might facilitate alternative pathways of presentation," Immunology Today, 21(2):83-88 (2000).
Harris et al., "Calreticulin and Calnexin Interact with Different Protein and Glycan Determinants During the Assembly of MHC Class I," The Journal of Immunology 160:5404-5409 (1998).
Hartl, F., "Molecular chaperones in cellular protein folding," Nature, 381:571-579 (1996).
Hasan et al., "Nucleic acid immunization: concepts and techniques associated with third generation vaccines," Journal of Immunological Methods, 229:1-22 (1999).
Hauser et al., "Secretory heat-shock protein as a dendritic cell-targeting molecule: a new strategy to enhance the potency of genetic vaccines," Gene Therapy, 11:924-932 (2004).
He et al., "Viral Recombinant Vaccines to the E6 and E7 Antigens of HPV-16," Virology, 270:146-161 (2000).
Heikema et al., "Generation of heat shock protein-based vaccines by intracellular loading of gp96 with antigen peptides," Immunology Letters, 57(1-3):69-74 (1997).
Heller, J. et al., "Tetra-O-methyl Nordihydroguaiaretic Acid Induces G2 Arrest in Mammalian Cells and Exhibits Tumoricidal Activity in Vivo," Cancer Research 61:5499-5504, (2001).
Hendrick et al., "Molecular chaperone functions of heat-shock proteins," Annu. Rev. Biochem., 62:349-384 (1993).
Higgins et al., "Fast and Sensitive Multiple Sequence Alignments on a Microcomputer," Comput. Appl. Biosci. 5(2):151-153 (1989).
Hokey et al., "DNA vaccines for HIV: challenges and opportunities," Springer Semin. Immunopathol., 28(3):267-279 (2006).
Hope et al., "Flt-3 Ligand, in Combination with Bovine Granulocyte-Macrophage Colony-Stimulating Factor and Interleukin-4, Promotes the Growth of Bovine Bone Marrow Derived Dendritic Cells," Scand. J. Immunol., 51:60-66 (2000).
Hsieh, C-J. et al., "Enhancement of vaccinia vaccine potency by linkage of tumor antigen gene to gene encoding calreticulin." Vaccine 22:3993-4001. (2004).
Hsu, K-F. et al., "Enhancement of suicidal DNA vaccine potency by linking *Mycobacterium tuberculosis* heat shock protein 70 to an antigen." Gene Therapy 8, 376-383 (2001).
Huang, C-H. et al. "Cancer Immunotherapy using a DNA vaccine encoding a single-chain trimer of MHC class I linked to an HPV-16 E6 immunodominant CTL epitope." Gene Therapy. 12:1180-1186 (2005).
Huang, C-C. et al., "Generation of Type-Specific Probes for the Detection of Single-Copy Human Papillomavirus by a Novel In Situ Hybridization Method," Mod. Pathol. 11(10):971-977 (1998).
Huang, C-C. et al., "HPV In Situ Hybridization with Catalyzed Signal Amplification and Polymerase Chain Reaction in Establishing Cerebellar Metastasis of a Cervical Carcinoma." Human Pathology, 30(5):587-591. (1999).
Huang, Q. et al., "In Vivo Cytotoxic T Lymphocyte Elicitation by Mycobacterial Heat Shock Protein 70 Fusion Proteins Maps to a Discrete Domain and Is CD4+ T Cell Independent," J. Exp. Med., 191(2):403-408 (2000).
Hung, C-F. et al. "A DNA vaccine encoding a single-chain trimer HLA-A2 linked to human mesothelin peptide generates anti-tumor effects against human mesothelin-expressing tumors." Vaccine 25:127-135 (2007).
Hung, C-F. et al., "Cancer Immunotherapy Using a DNA Vaccine Encoding the Translocation Domain of a Bacterial Toxin Linked to a Tumor Antigen." Cancer Research 61: 3698-3703 (2001).
Hung, C-F. et al., "Control of mesothelin-expressing ovarian cancer using adoptive transfer of mesothelin peptide-specific CD8+ T cells." Gene Therapy, pp. 1-9 (2007).

(56) References Cited

OTHER PUBLICATIONS

Hung et al., "Control of mesothelin-expressing ovarian cancer using adoptive transfer of mesothelin peptide-specific CD8+ T cells," Gene Therapy, 14(12):921-929 (2007).
Hung, C-F. et al., "DNA Vaccines Encoding li-PADRE Generates Potent PADRE-specific CD4+ T-Cell Immune Responses and Enhances Vaccine Potency." Mol. Ther. 15(6):1211-1219 (2007).
Hung, C-F. et al., "Enhancement of DNA Vaccine Potency by Linkage of Antigen Gene to a Gene Encoding the Extracellular Domain of Fms-like Tyrosine Kinase 3-Ligand." Cancer Research 61:1080-1088, (2001).
Hung, C-F. et al., "Enhancing Major Histocompatibility Complex Class I Antigen Presentation by Targeting Antigen to Centrosomes," Cancer Research. 63: 2393-2398, (2003).
Hung, C-F., et al., "Improving DNA Vaccine Potency by Linking Marek's Disease Virus Type 1 VP22 to an Antigen," Journal of Virology, 76(6):2676-2682 (2002).
Hung, C-F. et al., "Improving DNA vaccine potency via modification of professional antigen presenting cells." Current Opinion in Molecular Therapeutics, 5(1):20-24 (2003).
Hung et al., "Improving vaccine potency through intercellular spreading and enhanced MHC class I presentation of antigen," J. Immunology, 166(9):5733-5740 (2001).
Hung, C-F. et al., "Modifying professional antigen-presenting cells to enhance DNA vaccine potency," Methods in Molecular Medicine, 127:199-220 (2006).
Hung, C-F. et al., "Vaccinia virus preferentially infects and controls human and murine ovarian tumors in mice." Gene Therapy. 14:20-29 (2007).
Hunt et al., "Characterization and sequence of a mouse hsp70 gene and its expression in mouse cell lines," Gene, 87(2):199-204 (1990).
Hunt et al., "Conserved features of eurkaryotic hsp70 genes revealed by comparison with the nucleotide sequence of human hsp70," Proc. Natl. Acad. Sci. USA, 82:6455-6459 (1985).
Indraccolo et al., "Generation of expression plasmids for angiostatin, endostatin and TIMP-2 for cancer gene therapy," Int. J. Biological Markers, 14(4):251-256 (1999) (Abstract).
Iwasaki et al., "Enhanced CTL Responses Mediated by Plasmid DNA Immunogens Encoding Costimulatory Molecules and Cytokines," The Journal of Immunology, 158(10):4591-4601 (1997).
Jaffee et al., "Novel allogeneic granulocyte-macrophage colony-stimulating factor-secreting tumor vaccine for pancreatic cancer: a phase I trial of safety and immune activation," J. Clin. Oncol., 19(1):145-156 (2001).
Jager et al., "Simultaneous Humoral and Cellular Immune Response against Cancer-Testis Antigen NY-ESO-1: Definition of Human Histocompatibility Leukocyte Antigen (HLA)-A2-binding Peptide Epitopes," J. Exp. Med., 187:265-270 (1998).
Janetzki et al., "Generation of Tumor-Specific Cytotoxic T Lymphocytes and Memory T Cells by Immunization with Tumor-Derived Heat Shock Protein gp96," Journal of Immunotherapy, 21(4):269-276 (1998).
Jenkins et al., "Bioluminescent Imaging (BLI) to Improve and Refine Traditional Murine Models of Tumor Growth and Metastasis," Clin. Exp. Metastatis, 20(8):733-744 (2003).
Ji, H et al., "Antigen-Specific Immunotherapy for Murine lung Metastatic Tumors Expressing Human Papillomavirus Type 16 E7 Oncoprotein." Int. J. Cancer: 78, 41-45 (1998).
Ji, H et al., "Targeting Human Papillomavirus Type 16 E7 to the Endosomal/Lysosomal Compartment Enhances the Antitumor Immunity of DNA Vaccines against Murine Human Papillomavirus Type 16 E7-Expressing Tumors," Human Gene Therapy 10:2727-2740 (1999).
Jinno et al., "Domain II Mutants of Pseudomonas Exotoxin Deficient in Translocation," J. Biol. Chem., 264(7):15953-15959 (1989).
Kadkol, S. et al., Chapter 5: In Situ Hybridization in Cancer and Normal Tissue. Methods in Molecular Biology, vol. 223: Tumor Suppressor Genes, vol. II, Edited by W. El-Deiry, Humana Press Inc., Totowa, NJ. (2003).

Kang, T. et al., "Enhancing dendritic cell vaccine potency by combining a BAK/BAX siRNA-mediated antiapoptotic strategy to prolong dendritic cell life with an intracellular strategy to target antigen to lysosomal compartments." Int. J. Cancer, 120:1696-1703 (2007).
Kerbel, Robert S., "Tumor angiogenesis: past, present and the near future," Carcinogenesis 21(3):505-515 (2000).
Kim, T. et al., "A DNA Vaccine Co-Expressing Antigen and an Anti-Apoptotic Molecule Further Enhances the Antigen-Specific CD8+ T-Cell Immune Response." J. Biomed. Sci. 11:493-499 (2004).
Kim et al., "Co-transfection with cDNA encoding the Bcl family of anti-apoptotic proteins improves the efficiency of transfection in primary fetal neural stem cells," J. Neuroscience Methods, 117(2):153-158 (2002).
Kim et al., "Cytokine Molecular Adjuvants Modulate Immune Responses Induced by DNA Vaccine Constructs for HIV-1 and SIV," Journal of Interferon and Cytokine Research, 19(1):77-84 (1999).
Kim, J. et al., "Comparison of HPV DNA vaccines employing intracellular targeting strategies." Gene Therapy, 11:1011-1018 (2004).
Kim, T. et al., "DNA Vaccines Employing Intracellular Targeting Strategies and a Strategy to Prolong Dendritic Cell Life Generate a Higher Number of $CD8^+$ Memory T Cells and Better Long-Term Antitumor Effects Compared with a DNA Prime-Vaccinia Boost Regimin." Human Gene Therapy 16:26-34 (2005).
Kim, T. et al., "Enhancement of suicidal DNA vaccine potency by delaying suicidal DNA-induced cell death." Gene Therapy. 11:336-342. (2004).
Kim, T. et al., "Enhancement of DNA Vaccine Potency by Coadministration of a Tumor Antigen Gene and DNA Encoding Serine Protease Inhibitor-6." Cancer Research. 64:400-405 (2004).
Kim, T. et al., Enhancing DNA vaccine potency by coadministration of DNA encoding antiapoptotic proteins. J. Clin. Invest. 112:109-117 (2003).
Kim, T. et al., "Enhancing DNA Vaccine Potency by Combining a Strategy to Prolong Dendritic Cell Life with Intracellular Targeting Strategies." The Journal of Immunology, 171:2970-2976, (2003).
Kim, T. et al., "Generation and Characterization of DNA Vaccines Targeting the Nucleocapsid Protein of Severe Acute Respiratory Syndrome Caronavirus." Journal of Virology, 78(9):4638-4645. (2004).
Kim, T. et al. "Modification of Professional Antigen-Presenting Cells with Small Interfering RNA In vivo to Enhance Cancer Vaccine Potency." Cancer Res. 65(1):309-316 (2005).
Kim, D. et al., "Monitoring the Trafficking of Adoptively Transferred Antigen-Specific CD8-Positive T Cells In Vivo, Using Noninvasive Luminescence Imaging." Human Gene Therapy. 18: 1-14 (2007).
Kim, T. et al., "Vaccination with a DNA Vaccine Encoding Herpes Simplex Type 1 VP22 Linked to Antigen Generates Long-Term Antigen-Specific CD8-Positive memory T Cells and Protective Immunity." Human Gene Therapy. 15:167-177. (2004).
King et al., "DNA vaccines with single-chain Fv fused to fragment C of tetanus toxin induce protective immunity against lymphoma and myeloma," Nature Medicine, 4(11):1281-1286 (1998).
Kita et al., "Frequent Gene Expression of Granulocyte Colony-Stimulating Factor (G-CSF) Receptor in CD7+ Surface CD3— Acute Lymphoblastic Leukaemia," Leukemia, 7(8):1184-1190 (1993).
Klinman et al., "Contribution of CpG Motifs to the Immunogenicity of DNA vaccines," The Journal of Immunology, 158(8):3635-3639 (1997).
Koch et al., "Hijacking a chaperone: manipulation of the MHC class II presentation pathway," Immunology Today, 21(11):546-550 (2000).
Konen-Waisman et al., "Self and Foreign 60-Kilodalton Heat Shock Protein T Cell Epitope Peptides Serve As Immunogenic Carriers for a T Cell-Independent Sugar Antigen," J. Immunology, 154:5977-5985 (1995).

(56) References Cited

OTHER PUBLICATIONS

Konishi et al., "Japanese encephalitis DNA vaccine candidates expressing premembrane and envelope genes induce virus-specific memory B cells and long-lasting antibodies in swine," Virology, 268(1):49-55 (2000).
Koo et al., "The NK-1.1(−) Mouse: A Model to Study Differentiation of Murine NK Cells," J. Immunol. 125:2665-2672 (1986).
Lafond-Walker, A. et al., "Inducible Nitric Oxide Synthase Expression in Coronary Arteries of Transplanted Human Hearts with Accelerated Graft Arteriosclerosis." American Journal of Pathology, 151(4): 919-925 (1997).
Larregina et al., "Pattern of cytokine receptors expressed by human dendritic cells migrated from dermal explants," Immunology, 91:303-313 (1997).
Lazar et al., "Transforming Growth Factor α: Mutation of Aspartic Acid 47 and Leucine 48 Results in Different Biological Activities," Mol. Cell Biol., 8(3):1247-1252 (1988).
Lee et al., "DNA inoculations with HIV-1 recombinant genomes that express cytokine genes enbance HIV-1 specific immune responses," Vaccine, 17:473-479 (1999).
Lee et al., "Optimal Induction of Hepatitis C Virus Envelope-Specific Immunity by BiCistronic Plasmid DNA Inoculation with the Granulocyte-Macrophage Colony-Stimulating Factor Gene," Journal of Virology, 72(10):8430-8436 (1998).
Leitner et al., "DNA and RNA-Based Vaccines: Principles, Progress and Prospects," Vaccine 18(9-10):765-777 (1999).
Lemon et al., "Subcutaneous administration of inactivated hepatitis B vaccine by automatic jet injection," J. Med. Virol., 12(2):129-136 (1983).
Li et al., "Roles of heat-shock proteins in antigen presentation and cross-presentation," Curr. Opin. Immunol., 14(1):45-51 (2002).
Liaw, K. et al., "Human papillomavirus and cervical neoplasia: a case-control study in Taiwan." Int. J. Cancer. 62(5):565-71 (1995).
Lim et al., "Vaccination with an ovalbumin/interleukin-4 fusion DNA efficiently induces Th2 cell-mediated immune responses in an ovalbumin-specific manner," Arch. Pharm. Res., 21(5):537-542 (Abstract) (1998).
Lin, C-T. et al., "Boosting with Recombinant Vaccinia Increases HPV-16 E7-Specific T Cell Precursor Frequencies and Antitumor Effects of HPV-16 E7-Expressing Sindbis Virus Replicon Particles." Molecular Therapy. 8(4):559-566 (2003).
Lin, K.Y. et al., "Coinfection of HPV-11 and HPV-16 in a case of Laryngeal Squamous Papillomas With severe Dysplasia." Laryngoscope. 107(7):942-947 (1997).
Lin, K-Y. et al., "Ectopic Expression of Vascular Cell Adhesion Molecule-1 as a New Mechanism for Tumor Immune Evasion." Cancer. Res. 67(4):1832-1841 (2007).
Lin, K-Y. et al., "Treatment of Established Tumors with a Novel Vaccine That Enhances Major Histocompatibility Class II Presentation of Tumor Antigen." Cancer Research 56:21-26 (1996).
Lin, Y-Y. et al., "Vaccines against human papillomavirus." Frontiers in Bioscience. 12:246-264 (2007).
Ling, M. et al., "Preventive and Therapeutic Vaccines for Human Papillomavirus-Associated Cervical Cancers." J Biomed Sci 7:341-356 (2000).
Liu et al., "The emerging role of IL-15 in NK-cell development," Immunology Today, 21(3):113-116 (2000).
Liu et al., "Recombinant Adeno-Associated Virus Expressing Human Papillomavirus Type 16 E7 Peptide DNA Fused with Heat Shock Protein DNA as a Potential Vaccine for Cervical Cancer," Journal of Virology, 2888-2894 (2000).
Luke et al., "An OspA-based DNA vaccine protects mice against infection with Borrelia burgdorferi," J. Infect. Dis., 175(1):91-97 (1997).
Lyras and Rood, "Genetic Organization and Distribution of Tetracycline Resistance Determinants in Clostridium perfringens," Antimicrobial Agents and Chemotherapy 40:2500-2504 (1996).
Maecker et al., "DNA vaccination with cytokine fusion constructs biases the immune response to ovalbumin," Vaccine, 15(15):1687-1696 (Abstract) (1997).
Maki et al., "Human homologue of murine tumor rejection antigen p.96: 5'-Regulatory and coding regions and relationship to stress-induced proteins," Proc. Natl. Acad. Sci. USA, 87:5658-5662 (1990).
Mao, C-P. et al., "Immunological research using RNA interference technology." Immunology, 121:295-307 (2007).
Mao, C-P. et al. "Immunotherapeutic strategies employing RNA interference technology for the control of cancers." Journal of Biomedical Science 14:15-29 (2007).
Maraskovsky et al., "Dramatic Increase in the Numbers of Funtionally Mature Dendritic Cells in Flt-3 Ligand-treated Mice: Multiple Dendritic Cell Subpopulations Identified," J. Exp. Med., 184:1953-1962 (1996).
Massa et al., "Enhanced Efficacy of Tumor Cell Vaccines Transfected with Secretable hsp70," Cancer Research, 64:1502-1508 (2004).
McCluskie, et al., "Route and Method of Delivery of DNA Vaccine Influence Immune Responses in Mice and Non-Human Primates," Mol. Med. 5:287-300 (1999).
McKenzie et al., "Sequence and Immunogenicity of the 70-kDa Heat Shock Protein of Mycobacterium leprae," J. Immunol., 147(1):312-319 (1991).
Meinkoth et al., "Hybridization of nucleic acids immobilized on solid supports," Anal. Biochem., 138(2):267-284 (1984).
Meneguzzi et al., "Immunization against Human Papillomavirus Type 16 Tumor Cells with Recombinant Vaccinia Viruses Expressing E6 and E7," Virology, 181:62-69 (1991).
MHC Class-I Binding Peptide Prediction Results for the Maltose Binding Protein of Vector pMAL used in D8, using ProPred-I (http://www.imtech.res.in/raghava/propred1/) (2007).
Michel, N., et al., "Enhanced Immunogenicity of HPV 16 E7 Fusion Proteins in DNA Vaccination," Virology, 294:47-59 (2002) XP002201708.
Michel, N. et al., "Improved Immunogenicity of Human Papillomavirus Type 16 E7 DNA After Fusion to the Herpes Simplex Virus 1 VP22 Gene"; Barcelona, Spain, Jul. 23-28, 2000, Abstract, 458, XP002201712.
Mikayama et al., "Molecular cloning and functional expression of a cDNA encoding glycosylation-inhibiting factor," PNAS, 90:10056-10060 (1993).
Mold, D. et al., "Four Classes of HERV-K Long Terminal Repeats and Their Relative Promoter Strengths for Transcription." J Biomed Sci 4:78-82 (1997).
Molinari and Helenius, "Chaperone Selection During Glycoprotein Translocation into the Endoplasmic Reticulum," Science, 288(5464):331 (2000).
Moniz, M. et al., "HPV DNA Vaccines," Frontiers in Bioscience 8, d55-68, (2003).
More et al., "Activation of cytotoxic T cells in vitro by recombinant gp96 fusion proteins irrespective of the 'fused' antigenic peptide sequence," Immunol. Lett., 69(2):275-282 (1999).
Mrsny et al., "Mucosal administration of a chimera composed of Pseudomonas exotoxin and the gp120 loop sequence of HIV-1 induces both salivary and serum antibody responses," Vaccine, 17:1425-1433 (1999).
Nair et al., "Calreticulin Displays in Vivo Peptide-Binding Activity and Can Elicit CTL Responses Against Bound Peptides," Journal of Immunology 162(11):6426-5432 (1999).
Nakano et al., "Immunization with Plasmid DNA Encoding Hepatitis C Virus Envelope E2 Antigenic Domains Induces Antibodies Whose Immune Reactivity Is Linked to the Injection Mode," Journal of Virology 71:7101-7109 (1997).
Nawrocki, S. and Mackiewicz, A., "Genetically modified tumour vaccines—where we are today," Cancer Treatment Reviews 25:29-46 (1999).
Nguyen et al., "A Mutant of Human Papillomavirus Type 16 E6 Deficient in Bindong α-Helix Partners Displays Reduced Oncogenic Potential In Vivo," Journal of Virology, 76(24):13039-13048 (2002).
Nicchitta, C.V. and Reed, R.C., "The immunological properties of endoplasmic reticulum chaperones: a conflict of interest?," Essays in Biochemistry 36:15-25 (2000).

(56) References Cited

OTHER PUBLICATIONS

Noessner et al., "Tumor-Derived Heat Shock Protein 70 Peptide Complexes Are Cross-Presented by Human Dendritic Cells," The Journal of Immunology, 169:5424-5432 (2002).
Ockert et al., "Advances in Cancer Immunotherapy Symposium, Dresden, Germany," Immunology Today 20(2):63-65 (1999). Abstract.
Ohtsuka, K., "Cloning of a cDNA for heat-shock protein hsp40, a human homologue of bacterial DnaJ," Biochem. Biophys. Res. Commun., 197(1):235-240 (1993).
Okada et al., "Intranasal Immunization of a DNA Vaccine with IL-12-and Granulocyte-Macrophage Colony-Stimulating Factor (GM-CSF)-Expressing Plasmids in Lipsomes Induces Strong Mucosal and Cell Mediated Immune Responses Against HIV-1 Antigens," The Journal of Immunology, 159(7):3638-3647 (1997).
Operschall et al., "Enhanced protection against viral infection by co-administration of plasmid DNA coding for viral antigen and cytokines in mice," Journal of Clinical Virology, 13:17-27 (1999).
Ozols, RF., "Systemic therapy for ovarian cancer: current status and new treatments," Semin. Oncol., 33:53-11 (2006).
Pai, S I et al., "Prospects of RNA interference therapy for cancer." Gene Therapy. 13:464-477 (2006).
Pan et al., "A recombinant Listeria Monocytogenes Vaccine Expressing a Model Tumour Antigen Protects Mice Against Lethal Tumour Cell Challenge and Causes Regression of Established Tumours," Nature Medicine, 1(5):471-7 (1995).
Pan et al., "Regression of Established Tumors in Mice Mediated by the Oral Administration of a Recombinant Listeria monocytogenes Vaccine," Cancer Research, 55(21):4776-4779 (1995).
Pardoll et al., "Exposing the Immunology of Naked DNA Vaccines," Immunity, 3:165-169 (1995).
Pejawar-Gaddy et al., "Cancer vaccines: accomplishments and challenges," Crit. Rev. Oncol. Hematol., 67(2):93-102 (2008).
Peng et al., "A combination of DNA vaccines targeting human papillomavirus type 16 E6 and E7 generates potent antitumor effects." Gene Therapy. 13:257-265 (2006).
Peng, S. et al., "Characterization of HLA-A2-restricted HPV-16 E7-specific CD8+ T-cell immune responses induced by DNA vaccines in HLA-A2 transgenic mice." Gene Therapy. 13:67-77 (2006).
Peng, S., et al.; "Characterization of HPV16-E6 DNA vaccines employing intracellular targeting and intercellular spreading strategies;" Journal of Biomedical Science, 12:689-700 (2005).
Peng, S. et al., "Development of a DNA Vaccine targeting Human Papillomavirus Type 16 Oncoprotein E6." Journal of Virology. 78(16):8468-8476. (2004).
Peng et al., "Efficient delivery of DNA vaccines using human papillomavirus pseudovirions," Gene Therapy, 17(12):1453-1464 (2010).
Peng, S. et al., "HLA-DQB1*02- restricted HPV-16 E7 Peptide-Specific CD4+ T-Cell Immune Responses Correlate with Regression of HPV-16-Associated High-Grade Squamous Intraepithelial Lesions." Clin. Cancer Res. 13(8):2479-2487 (2007).
Peng, S. et al., "Vaccination with Dendritic Cells Transgected with BAK and BAX siRNA Enhances Antigen-Specific Immune Responses by Prolonging Dendritic Cell Life." Human Gene Therapy 16:584-593 (2005).
Peoples et al., "Vaccine Implications of Folate Binding Protein, a Novel Cytotoxic T Lymphocyte-recognized Antigen System in Epithelial Cancers," Clinical Cancer Research, 5:4214-4223 (1999).
Pfisterer et al., "Management of platinum-sensitive recurrent ovarian cancer," Semin. Oncol., 33:512-516 (2006).
Przepiorka et al., "Heat shock protein peptide complexes as Immunotherapy for human cancer," Molecular Medicine Today (Reviews), 4(11):478-484 (1998).
Ramos-Soriano, A. et al., "Enteric pathogens associated with gastrointestinal dysfunction in children with HIV infection." Molecular and Cellular Probes 10: 67-73 (1996).
Rashid, A. et al., "Mitochondrial Proteins That Regulate Apoptosis and Necrosis Are Induced in Mouse Fatty Liver." Hepatology 29:1131-1138 (1999).
Ray et al., "Apoptosis Induction in Prostate Cancer Cells and Xenografts by Combined Treatment with APO2 Ligand/Tumor Necrosis Factor-related apoptosis-inducing Ligand and CPT-11," Cancer Research, 63:4713-4723 (2003).
Robinson et al., "DNA Vaccines," Seminars in Immunology, 9(5):271-283 (1997).
Roby et al., "Development of a syngeneic mouse model for events related to ovarian cancer," Carcinogenesis, 21(4):585-591 (2000).
Roden, R. et al. "The impact of preventative HPV Vaccination." Discovery Medicine. vol. 6, No. 35, pp. 175-181 (2006).
Roden, R. et al., "Vaccination to Prevent and Treat Cervical Cancer." Human Pathology. 35(8): 971-982. (2004).
Roden and Wu. "How will HPV vaccines affect cervical cancer?" Nature Reviews. vol. 6, pp. 753-763. (2006).
Rodriguez et al., "DNA Immunization with Minigenes: Low Frequency of Memory Cytotoxic T Lymphocytes and Inefficient Antiviral Protection Are Rectified by Ubiquitination," Journal of Virology, 72(6):5174-5181 (1998).
Rogers et al., "Multistage Multiantigen Heterologous Prime Boost Vaccine for *Plasmodium knowlesi* Malaria Provides Partial Protection in Rhesus Macaques," Infection and Immunity, 69(9):5565-5572 (2001).
Rouse et al., "Induction In Vitro of Primary Cytotoxic T-Lymphocyte Responses with DNA Encoding Herpes Simplex Virus Proteins," Journal of Virology, 68(9):5685-5689 (1994).
Sanchez-Perez et al., "Killing of Normal Melanocytes, Combined with Heat Shock Protein 70 and CD40L Expression, Cures Large Established Melanomas," The Journal of Immunology, 177:4168-4177 (2006).
Sarmiento et al., "IgCx or IgM Monoclonal Antibodies Reactive with Different Determinants of the Molecular Complex Bearing LYT 2 Antigen Block T Cell Mediated Cytolysis in the Absence of Complement," J. Immunol., 125(6):2665-2672 (1980).
Sasaki et al., "Adjuvant formulations and delivery systems for DNA vaccines," Methods, 31(3):243-254 (2003).
Schultes et al., "Monitoring of immune responses to CA125 with IFN-gamma ELISPOT assay," J. Immunol. Methods, 279:1-15 (2003).
Schutze-Redelmeier et al., "Introduction of Exogenous Antigens into the MHC Class I Processing and Presentation Pathway by *Drosophila* Antennapedia Homeodomain Primes Cytotoxic T Cells in Vivo," Journal of Immunology 157:650-655 (1996).
Serody et al., "T Cell Activity After Dendritic Cell Vaccination Is Dependent on Both the Type of Antigen and the Mode of Delivery," J. Immunology, 164(9):4961-4967 (2000).
Shalinsky et al., "Marked Antiangiogenic and Antitumor Efficacy of AG3340 in Chemoresistant Human Non-Small Cell Lung Cancer Tumors: Single Agent and Combination Chemotherapy Studies," Clincal Cancer Research 5:1905-1917 (1999).
Sheikh et al., "Guns, genes, and spleen: a coming of age for rational vaccine design," Methods, 31(3):183-192 (2003).
Sin et al., "Enhancement of protective humoral (Th2) and cell mediated (Th1) immune responses against herpes simplex virus-2 co-delivery of granulocyte-macrophage colony-stimulating factor expression cassettes," Eur. J. Immunol., 28:3530-3540 (1998).
Sin, J.I., "Human papillomavirus vaccines for the treatment of cervical cancer," Expert Review Vaccines, 5(6):783-792 (2006).
Smahel et al., "DNA vaccine against oncogenic hamster cells transformed by HPV16 E6/E7 oncogenes and the activated *ras* oncogene," Oncology Reports, 6:211-215 (1999).
Smahel et al., "Immunisation with modified HPV16 E7 genes against mouse oncogenic TC-1 cell sublines with downregulated expression of MHC class I molecules," Vaccine, 21:1125-1136 (2003).
Srivastava et al., "Evidence for Peptide-Chaperoning by the Endoplasmic Reticular Heat Shock Protein GP96: Implications for Vaccination Against Cancer and Infectious Diseases," J. Cell. Biochem. Suppl. 17D:94 (Abstract NZ 014) (1993).
Srivastava et al., "Heat Shock Proteins Come of Age: Primitive Functions Acquire New Roles in an Adaptive World," Immunity, 8:657-665 (1998).

(56) References Cited

OTHER PUBLICATIONS

Srivastava, P., "Interaction of heat shock proteins with peptides and antigen presenting cells: chaperoning of the innate and adaptive immune responses," Annu. Rev. Immunol., 20:395-425 (2002).
Srivastava et al., "5'-Structural analysis of genes encoding polymorphic antigens of chemically induced tumors," Proc. Natl. Acad. Sci. USA, 84:3807-3811 (1987).
Srivastava et al., "The Serologically Unique Cell Surface Antigen of Zajdela Ascitic Heptoma is also its Tumor-Associated Transplantation Antigen," Int. J. Cancer, 33:417-422 (1984).
Srivastava et al., "Tumor rejection antigens of chemically induced sarcomas of inbred mice," Proc. Natl.-Acad. Sci. USA, 83:3407-3411 (1986).
Steinman et al., "The Sensitization Phase of T-Cell-mediated Immunity," Annals of The New York Academy of Sciences, 546:80-90 (1988).
Stevenson et al., "Idiotypic DNA Vaccines Against B-cell Lymphoma," Immunological Reviews, 145:211-228 (1995).
Suto et al., "A Mechanism for the Specific Immunagenicity of Heat Shcck Protein-Chaperoned Peptides," Science, 269:1585-1588 (1995).
Suzue et al., "Adjuvant-Free HSP70 Fusion Protein System Elicits Humoral and Cellular Immune Responses to HIV-1," Journal of Immunology 156:873-879 (1996).
Suzue et al., "Heat shock fusion proteins as vehicles for antigen delivery into the major histocompatibility complex class I presentation pathway," Proc. Natl. Acad. Sci. USA 94:13146-13151 (1997).
Syrengelas et al., "DNA immunization induces protective immunity against B-cell lymphoma," Nature Medicine, 2( 9):1038-1041 (1996).
Szymczak et al., "Correction of multi-gene deficiency in vivo using a single 'self-cleaving' 2A peptide-based retroviral vector," Nat. Biotechnol., 22(5):589-594 (2004).
Tamura et al., "Immunotherapy of Tumors with Autologous Tumor-Derived Heat Shock Protein Preparations," Science, 278:117-120 (1997).
Theriault et al., "Extracellular HSP70 binding to surface receptors present on antigen presenting cells and endothelial/epithelial cells," FEBS Lett., 579(9):1951-1960 (2005).
Thomas et al., "Mesothelin-specific CD8+ T Cell Responses Provide Evidence of In Vivo Cross-Priming by Antigen-Presenting Cells in Vaccinated Pancreatic Cancer Patients," J. Exp. Med., 200(3):297-306 (2004).
Thornburg et al., "Induction of Cytotoxic T Lymphocytes With Dendritic Cells Transfected With Human Papillomavirus E6 and E7 RNA: Implications for Cervical Cancer Immunotherapy," Journal of Immunotherapy, 23(4):412-418 (2000).
Ting et al., "Human gene encoding the 78,000-dalton glucose-regulated protein and its pseudogene: structure, conservation, and regulation," DNA, 7(4):275-286 (1988).
Tobery et al., "Targeting of HIV-1 antigen for rapid intracellular degradation enhances cytotoxic T lymphocyte (CTL) recognition and the induction of De Novo CTL responses in Vivo after immunization," J. Exp. Med., 185(5):909-920 (1997).
Tomson, T. et al. "Human papillomavirus vaccines for the prevention and treatment of cervical cancer." Current Opinion in Investigational Drugs, 5(12):1247-1261. (2004).
Torres et al., "Differential Dependence on Target Site Tissue for Gene Gun and Intramuscular DNA Immunizations," The Journal of Immunology 158:4529-4532 (1997).
Trimble, C. et al., "Comparison of the CD8+ T cell responses and antitumor effects generated by DNA vaccine administered through gen gun, biojector and syringe." Vaccine. 21:4036-4042, (2003).
Trimble C, et al., "Spontaneous Regression of High-Grade Cervical Dysplasia: Effects of Human Papillomavirus Type and HLA Phenotype." Clin. Cancer Res. 11(13):4717-4723 (2005).
Trompeter, Hans-Ingo et al., "Variable Nuclear Cytoplasmic Distribution of the 11.5-kDa Zinc-binding Protein (Parathymosin-α)
and Identification of a Bipartite Nuclear Localization Signal," The Journal of Biological Chemistry 271(2):1187-1193 (1996).
Trujillo, J. et al., "Characterization of human papillomavirus type 57b: transforming activity and comparative sequence analysis as probes for biological determinants associated with high-risk oncogenic viruses." Virus genes. 12(2):165-78 (1996).
Tsen, S-W. et al., "Enhancing DNA Vaccine Potency by Modifying the Properties of Antigen-Presenting Cells," Expert Review of Vaccines, 6(2):227-239 (2007).
Tseng et al., "Systemic tumor targeting and killing by Sindbis viral vectors," Nature Biotechnology, 22(1):70-77 (2004).
Tseng et al., "Using Sindbis Viral Vectors for Specific Detection and Suppressin of Advanced Ovarian Cancer in Animal Models," Cancer Research, 64:6684-6692 (2004).
Tuting et al., "Autologous Human Monocyte-Derived Dendritic Cells Genetically Modified to Express Melanoma Antigens Elicit Primary Cytotoxic T Cell Responses In Vitro: Enhancement by Cotransfection of Genes Encoding the Th1-Biasing Cytokines IL-12 and IFN-$\alpha^1$," Journal of Immunology 160:1139-1147 (1998).
Udono et al., "Cellular requirements for tumor-specific immunity elicited by hear shock proteins: Tumor rejection antigen gp96 primes CD8+ T cells in vivo," Proc. Natl. Acad. Sci. USA, 91:3077-3081 (1994).
Udono et al., "Comparison of Tumor specific immunogenicities of stress-induced proteins gp96, hsp90, and hsp70'," The Journal of Immunology, 152(11):5398-5403 (1994).
Udono et al., "Heat Shock Protein 70-associated Peptides Elicit Specific Cancer Immunity," J. Exp. Med., 178:1391-1396 (1993).
Ulmer et al., "Presentation of an exogenous antigen by major histocompatibility complex class I molecules," Eur. J. Immunol., 24:1590-1596 (1994).
van Bergen et al., "Superior Tumor Protection Induced by a Cellular Vaccine Carrying a Tumor-specific T Helper Epitope by Genetic Exchange of the Class II-associated Invariant Chain Peptide," Cancer Research, 60(22):6427-6433 (2000).
van der Burg et al., "Pre-clinical safety and efficacy of TA-CIN, a recombinant HPV16 L2E6E7 fusion protein vaccine, in homologous and heterologus prime-boost regimens," Vaccine, 19:3652-3660 (2001).
van Tienhoven et al., "Induction of antigen specific CD4 + T cell responses by invariant chain based DNA vaccines," Vaccine, 19:1515-1519 (2001).
Vu, K. et al., "Cellular Proliferation, Estrogen Receptor, Progesterone Receptor, and bcl-2 Expression in GnRH Agonist-Treated Uterine Leiomyomas." Human Pathology 29:359-363 (1998).
Wang et al., "CD40 Is a Cellular Receptor Mediating Mycobacterial Heat Shock Protein 70 Stimulation of CC-Chemokines," Immunity, 15:971-983 (2001).
Wang et al., "A Single Amino Acid Determines Lysophospholipid Specificity of the $S1P_1$ (EDG1) and $LPA_1$ (EDG2) Phospholipid Growth Factor Receptors," The Journal of Biological Chemistry, 276(52):49213-49220 (2001).
Wang, T-L. et al., "Intramuscular administration of E7-transfected dendritic cells generates the most potent E7-specific anti-tumor immunity." Gene Therapy 7:726-733 (2000).
Weiss et al., "A plasmid encoding murine granulocyte-macrophage colony-stimulating factor increases protection conferred by a malaria DNA vaccine," The Journal of Immunology, 161(5):2325-2332 (1998).
Whisstock et al., "Prediction of protein function from protein sequence and structure," Quarterly Reviews of Biophysics, 3:307-340 (2003).
Whittall et al., "Interaction between the CCR5 chemokine receptors and microbial HSP70," Eur. J. Immunol., 36(9):2304-2314 (2006).
Wu, T-C. et al., "A Reassessment of The Role of B7-1 Expression in Tumor Rejection." J. Exp. Med. 182:1415-1421 (1995).
Wu, T-C. et al., "Demonstration of human papillomavirus (HPV) genomic amplification and viral-like particles from CaSki cell line in SCID mice." Journal of Virological Methods 65:287-298 (1997).
Wu, T-C. et al., "Detection of the Human Cytomegalovirus 2.0-kb Immediate Early Gene I Transcripts in Permissive and Nonpermissive Infections by RNA in situ Hybridization." J Biomed Sci 4:19-27 (1997).

(56) References Cited

OTHER PUBLICATIONS

Wu, T-C, et al., "Engineering an intracellular pathway for major histocompatibility complex class II presentation of antigens." Proc. Natl. Acad. Sci. 92:11671-11675 (1995).
Wu, T-C. "Therapeutic human papillomavirus DNA vaccination strategies to control cervical cancer." European Journal of immunology. 37:310-314 (2007).
Yen, M. et al., "Diffuse Mesothelin Expression Correlates with Prolonged Patient Survival in Ovarian Serous Carcinoma." Clin. Cancer. Res. 12(3):827-831 (2006).
Yokokawa et al., "Identification of Novel Human CTL Epitopes and Their Agonist Epitopes of Mesotheliin," Clin. Cancer Res., 11(17):6342-6351 (2005).
International Search Report dated Oct. 15, 2001 from PCT/US2000/41422.
International Search Report dated Nov. 13, 2007 from PCT/US2003/10235.
International Search Report dated Dec. 3, 2002 from PCT/US2001/24134.
International Search Report dated Sep. 20, 2002 from PCT/US2002/02598.
International Search Report dated Jun. 28, 2002 from PCT/US2001/23966.
International Search Report dated Mar. 25, 2005 from PCT/US2004/05292.
International Search Report dated Apr. 1, 2005 from PCT/US2004/13756.
International Search Report dated Jul. 7, 2008 from PCT/US2005/47200.
International Search Report dated Mar. 22, 2007 from PCT/US2006/02707.
International Search Report dated Aug. 13, 2008 from PCT/US2007/76525.
Supplementary EP Search Report dated Mar. 6, 2006 from EP 02 70 7618.
Supplementary EP Search Report dated Sep. 28, 2006 from EP 04 75 1244.
Supplementary EP Search Report dated May 30, 2008 from EP 06 73 3904.
International Search Report dated Jan. 3, 2011 from PCT/US2010/032779.
Chuang et al., "Combination of Viral Oncolysis and Tumor-Specific Immunity to Control Established Tumors," Clinical Cancer Research, 15(14):4581-4588 (2009).
Oltersdorf et al., "Identification of Human Papillomavirus Type 16 E7 Protein by Monoclonal Antibodies," J. Gen. Virol., 68:2933-2938 (1987).
Ye et al., "Cytokine Transgene Expression and Promoter Usage in Primary CD34+ Cells Using Particle-Mediated Gene Delivery," Human Gene Therapy, 9:2197-2205 (1998).
Mandavi et al., "Vaccines Against Human Papillomavirus and Cervical Cancer: Promises and Challenges," The Oncologist, 10:528-538 (2005).
Andrei et al., "Induction of Apoptosis by Cidofovir in Human Papillomavirus (HPV)-Positive Cells," Oncology Research, 12:397-408 (2000).
Ballard et al., "Anthrax toxin-mediated delivery of a cytotoxic T-cell epitope in vivo," Proc. Natl. Acad. Sci., 93:12531-12534 (1996).
Beasley, R.P. et al., "Hepatocellular carcinoma and hepatitis B virus. A prospective study of 22 707 men in Taiwan." Lancet 2:1129-1133 (1981).
Beaudenon, S., et al. "A novel type of human papillomavirus associated with genital neoplasias." Nature 321:246-9, 1986.
Bennett et al., "Induction of CD8+ Cytotoxic T Lymphocyte Response by Cross-priming Requires Cognate CD4+ T Cell Help," J. Exp. Med, 186(1):65-70 (1997).
Bowie et al., "Deciphering the Message in Protein Sequences: Tolerance to Amino Acid Substitutions," Science, 247:1306-1310 (1990).

Boyle, J.S.; "Influence of cellular location of expressed antigen on the efficacy of DNA vaccination: cytotoxic T lymphocyte and antibody responses are suboptimal when antigen is cytoplasmic after intramuscular DNA immunization." Int Immunol 1997 9:1897-1906.
Bramson, et al., "Direct Intratumoral Injection of an Adenovirus Expressing Interleukin-12 Induces Regression and Long-Lasting Immunity That Is Associated with Highly Localized Expression of Interleukin-12," Human Gene Therapy, 7(16): 1995-2002 (1996).
Buller, et al., "Decreased virulence of recombinant vaccinia virus expression vectors is associated with a thymidine kinase-negative phenotype," Nature, 317(6040): 813-815 (1985).
CA098252-06; A phase I trial to assess the immunogenicity, safety, tolerability and efficacy; Sep. 1, 2009.
CA098252-07; A phase I trial to assess the immunogenicity, safety, tolerability and efficacy; Sep. 1, 2010.
CA105696; A phase III trial of a therapeutic HPV vaccine; CA105696; Sep. 15, 2003.
CA123876; Therapeutic DNA-MVA prime boost vaccination for HPV disease; Sep. 1, 2006.
CA128232; Therapeutic HPV vaccination for Stage IB1 cervical cancer; Sep. 1, 2008.
Cassetti et al., "Antitumor efficacy of Venezuelan equine encephalitis virus replicon particles encoding mutated HPV16 E6 and E7 genes," Vaccine, 22:520-527 (2004).
Celluzzi, et al., "Cutting Edge: Physical Interaction Between Dendritic Cells and Tumor Cells Results in an Immunogen that Induces Protective and Therapeutic Tumor Rejection," J Immunol, 160(7): 3081-3085 (1998).
Chang, M.H. et al.; "Universal hepatitis B vaccination in Taiwan and the incidence of hepatocellular carcinoma in children." Taiwan Childhood Hepatoma Study Group. New Engl. J. Med. 336, 1855-1859 (1997).
Chen, C.H. et al., "Experimental vaccine strategies for cancer immunotherapy." J Biomed Sci. 5: 231-52, 1998.
Christensen et al., "Combination Treatment with Intralesional Cidofovir and Viral-DNA Vaccination Cures Large Cottontail Rabbit Papillomavirus-Induced Papillomas and Reduces Recurrences," Antimicrobial Agents and Chemotherapy, 45(4):1201-1209 (2001).
Christensen et al., "In vivo anti-papillomavirus activity of nucleoside analogues including cidofovir on CRPV-induced rabbit papillomas," Antiviral Research, 48:131-142 (2000).
Clinicaltrials.gov; Summary NCT00788164; Vaccine Therapy With or Without Imiquimod in Treating Patients With Grade 3 Cervical Intraepithelial Neoplasia; Nov. 7, 2008.
Clinicaltrials.gov; Summary NCT00988559; Therapeutic Vaccination for Patients With HPV16+ Cervical Intraepithelial Neoplasia (CIN2/3); Oct. 1, 2009.
Condon, C., et al., "DNA-based immunization by in vivo transfection of dendritic cells." Nat Med 1996 2:1122-1128.
Demierre et al., "Chemoprevention of Melanoma," Current Oncology Reports, 6:406-413 (2004).
Diaz, Rosa Maria, et al. "Oncolytic Immunovirotherapy for Melanoma Using Vesicular Stomatitis Virus," Cancer Research, 67(6): 2840-2848 (2007).
Extended European Search Report dated Apr. 15, 2013, from EP 10772568.1.
Fayolle et al., "In Vivo Induction of CTL Responses by Recombinant Adenylate Cyclase of Bordetella pertussis Carrying Viral CD8+ T Cell Epitopes[1]," J. Immunol., 156:4697-4706 (1996).
Fu, T.M., et al., "Priming of cytotoxic T lymphocytes by DNA vaccines: requirement for professional antigen presenting cells and evidence for antigen transfer from myocytes." Mol Med 1997, 3(6) 362:37119.
Galbraith et al., "Effects of 5,6-Dimethylxanthenone-4-Acetic Acid on Human Tumor Microcirculation Assessed by Dynamic Contrast-Enhanced Magnetic Resonance Imaging," Journal of Clinical Oncology, 20(18):3826-3840 (2002).
Gambhira et al., "Vaccination of Healthy Volunteers with Human Papillomavirus Type 16 L2E7E6 Fusion Protein Induces Serum Antibody that Neutralizes across Papillomavirus Species," Cancer Reseach, 66:11120-11124 (2006).

(56) References Cited

OTHER PUBLICATIONS

Gissmann, L. et al., "Persistence and expression of human papillomavirus DNA in genital cancer." *Ciba Found Symp. 120*:190-207, 1986.
Gurunathan, S., et al., "DNA vaccines generated long-term cell-mediated immunity." *Annu Rev Immunol 18*: 927-974, 2000.
IPRP and Written Opinion for PCT/US2010/032779 dated Nov. 1, 2011.
Johnston, S.A. et al., *In Vitro Cell Dev Biol 27*:11, 1991.
Kaiser, C.A. "Many random sequences functionally replace the secretion signal sequence of yeast invertase." Science 1987 235:312-317.
Kaufmann, et al., "Safety and Immunogenicity of TA-HPV, a Recombinant Vaccinia Virus Expressing Modified Human Papillomavirus (HPV)-16 and HPV-18 E6 and E7 Genes, in Women with Progressive Cervical Cancer," Clin Cancer Res, 8(12): 3676-3685 (2002).
Kent, S. J. et al., "Enhanced T-Cell Immunogenicity and Protective Efficacy of a Human Immunodeficiency Virus Type 1 Vaccine Regimen Consisting of Consecutive Priming with DNA and Boosting with Recombinant Fowlpox Virus," J. of Virology, 72(12):10180-10188 (1998).
Kinoshita et al., "Spreading of the immune response from 52 kDaRo and 60 kDaRo to calreticulin in experimental autoimmunity," Lupus, 7:7-11 (1998).
Lee, et al., "A method for preparing beta-hCG COOH peptide-carrier conjugates of predictable composition," Molecular Immunology, 17(6): 749-756 (1980).
Lee, et al., "Major histocompatibility complex class I presentation of exogenous soluble tumor antigen fused to the B-fragment of Shiga toxin," Eur J Immunol, 28: 2726-2737 (1998).
Li, et al., "Novel Vaccination Protocol with Two Live Mucosal Vectors Elicits Strong Cell-Mediated Immunity in the Vagina and Protects against Vaginal Virus Challenge," J Immunol, 180: 2504-2513 (2008).
Lukas, J. "DNA tumor virus oncoproteins and retinoblastoma gene mutations share the ability to relieve the cell's requirement for cyclin D1 function in G1." J Cell Biol 1994 125:625-638.
Mahdavi et al., "Vaccines Against Human Papillomavirus and Cervical Cancer: Promises and Challenges," The Oncologist, 10:528-538 (2005).
McDermott, et al., "A Phase II Trial of Concurrent Biochemotherapy with Cisplatin, Vinblastine, Dacarbazine, Interleukin 2, and Interferon alpha-2B in Patients with Metastatic Melanoma," Clin Cancer Res, 6(6): 2201-2208 (2000).
Mullen, et al., "Viral Oncolysis," The Oncologist, 7: 106-119 (2002).
Munger, K. et al., "Complex formation of human papillomavirus E7 proteins with the retinoblastoma tumor suppressor gene product." *EMBO J 8*:4099-4105, 1989.
Murray, P.J. et al. "Stress and immunological recognition in host-pathogen interactions." J. Bacteriology 174:4193-6 1992.
Nichols, W.W. "Potential DNA vaccine integration into host cell genome." Ann N Y Acad Sci 1995 772:30-39.
Nicolau, C. et al., "In vivo expression of rat insulin after intravenous administration of the liposome-entrapped gene for rat insulin I." *Proc Natl Acad Sci USA 80*:1068, 1983.
O'Brien, R. et al. Cell 1989 57:664-674 1989.
Office Action for Canadian Application No. 2,760,310 dated May 9, 2013.
Pardoll, D.M. Cancer vaccines. *Nature Med 4*:525-31, 1998.
Pike et al., "Calreticulin and Calreticulin Fragments Are Endothelial Cell Inhibitors That Suppress Tumor Growth," Blood, 94:2461-2468 (1999).
Porgador, A. et al.; "Predominant role for directly transfected dendritic cells in antigen presentation to CD8+ T cells after gene gun immunization." J. Exp Med 1998 188:1075-1082.
Reimann and Schirmbeck, "Alternative pathways for processing exogenous and endogenous antigens that can generate peptides for MHC class I-restricted presentation," Immunological Reviews, 172(1): 131-152 (1999).
Ribas, et al., "Characterization of antitumor immunization to a defined melanoma antigen using genetically engineered murine dendritic cells," Cancer Gene Therapy, 6(6): 523-536 (1999).
Robinson, H.L., "Nucleic acid vaccines: an overview." *Vaccine 15*:785-787, 1997.
Roitt et al., Immunology (textbook), 5th Edition, p. 128 (1998).
Saade, et al., "Technologies for enhanced efficacy of DNA vaccines," Exp Rev Vaccines, 11(2): 189-209 (2012).
Shata et al., "Optimization of recombinant vaccinia-based ELISPOT assay," Journal of Immunological Methods, 283:281-289 (2003).
Soriano, P. et al., "Targeted and nontargeted liposomes for in vivo transfer to rat liver cells of a plasmid containing the preproinsulin I gene." *Proc Nat. Acad Sci USA 80*:7128, 1983.
Sun, et al., "Local HPV Recombinant Vaccinia Boost Following Priming with an HPV DNA Vaccine Enhances Local HPV-Specific CD8+ T-cell-Mediated Tumor Control in the Genital Tract," Clin Cancer Res, 22(3): 657-669 (2016).
Tagawa et al., "Phase I Study of Intranodal Delivery of a Plasmid DNA Vaccine for Patients with Stage IV Melanoma," Cancer, 98:144-154 (2003).
Titomirov, A.V. et al., "In vivo electroporation and stable transformation of skin cells of newborn mice by plasmid DNA." *Biochim Biophys Acta 1088*:131, 1991.
Wang, et al., "pH-sensitive immunoliposomes mediate target-cell-specific delivery and controlled expression of a foreign gene in mouse," PNAS, 84(22): 7851-7855 (1987).
Wang, R.F. et al., "Human tumor antigens for cancer vaccine development." *Immunol Rev. 170*:85-100, 1999.
Williams, R.S. et al., "Introduction of foreign genes into tissues of living mice by DNA-coated microprojectiles." *Proc Natl Acad Sci USA 88*:2726, 1991.
Wilson, J.M. et al., "Hepatocyte-directed gene transfer in vivo leads to transient improvement of hypercholesterolemia in low density lipoprotein receptor-deficient rabbits." *J Biol Chem 267*:963, 1992.
Wu (1994) "Immunology of the human papilloma virus in relation to cancer." *Curr. Opin. Immunol.* 6:746-754.
Wu, C.H. et al., "Targeting genes: delivery and persistent expression of a foreign gene driven by mammalian regulatory elements in vivo." *J Biol Chem 264*:16985, 1989.
Wu, G.Y. et al., "Receptor-mediated gene delivery and expression in vivo." *J Biol Chem 263*:14621, 1988.
Xiang et al., "A New Dynamic Model of CD8+ T Effector Cell Responses via CD4+ T Helper-Antigen-Presenting Cells[1]," J. Immunol., 174:7497-7505 (2005).
Yang, et al., "Intratumoral Vaccination with Vaccinia-Expressed Tumor Antigen and Granulocyte Macrophage Colony-Stimulating Factor Overcomes Immunological Ignorance to Tumor Antigen," Cancer Res, 63(20): 6956-6961 (2003).
Yang, N-S, et al., "In vivo and in vitro gene transfer to mammalian somatic cells by particle bombardment." *Proc Natl Acad Sci USA 87*:9568, 1990.
Zelenin, A.V. et al., "Genetic transformation of mouse cultured cells with the help of high-velocity mechanical DNA injection." *FEBS Lett 244*:65, 1989.
Zelenin, A.V. et al., "High-velocity mechanical DNA transfer of the chloramphenicolacetyl transferase gene into rodent liver, kidney and mammary gland cells in organ explants and in vivo." *FEBS Lett 280*:94, 1991.

* cited by examiner

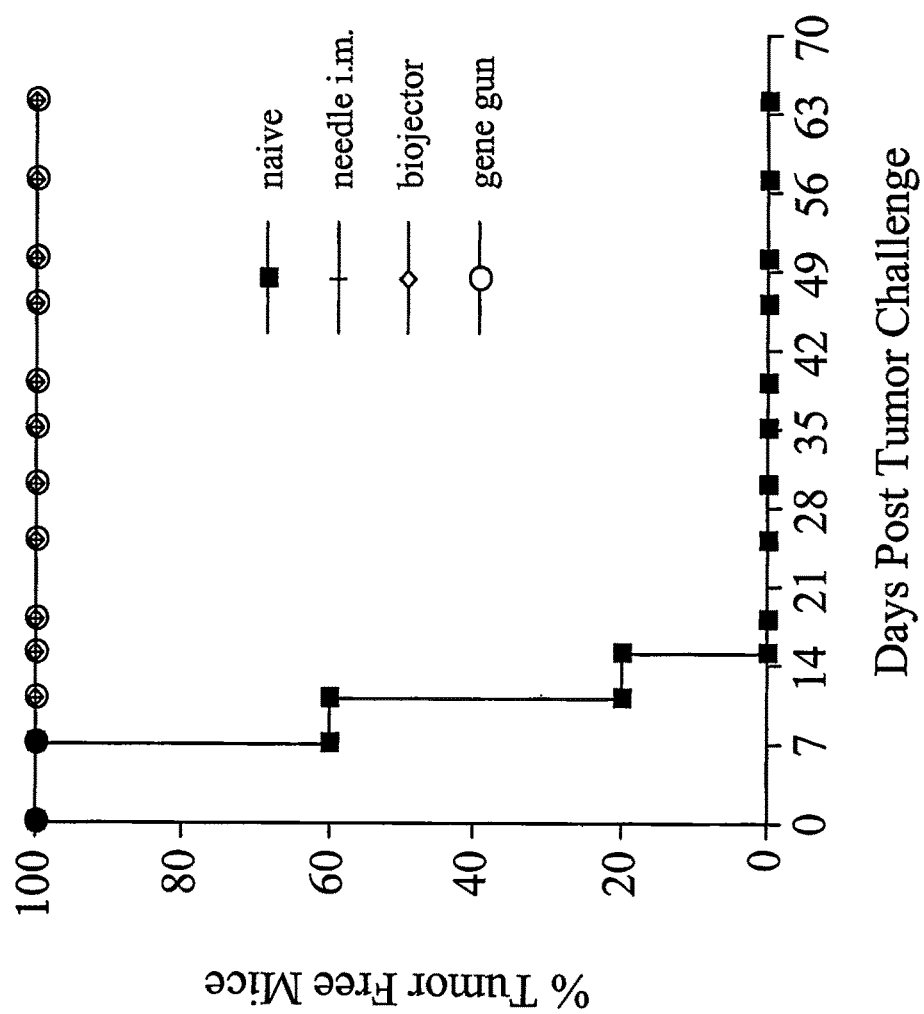

Fig. 5A
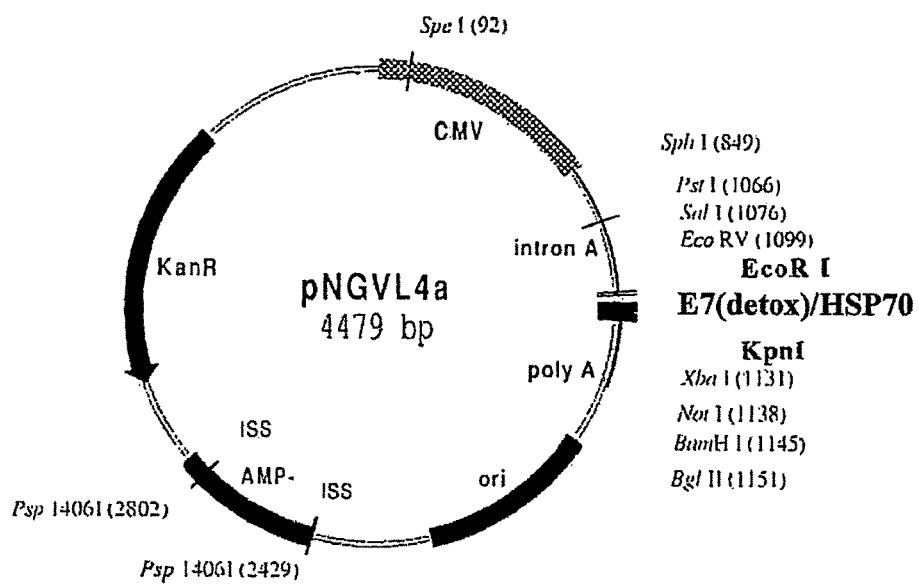
Point mutations introduced to generate detoxified E7/hsp70
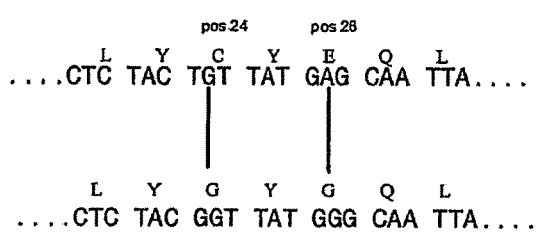
Fig. 5B

ANTI-CANCER DNA VACCINE EMPLOYING PLASMIDS ENCODING SIGNAL SEQUENCE, MUTANT ONCOPROTEIN ANTIGEN, AND HEAT SHOCK PROTEIN

BACKGROUND OF THE INVENTION

Field of the Invention

The present invention in the fields of molecular biology, immunology and medicine relates to chimeric nucleic acid molecules that encode an antigen, a signal peptide, and an immunogenicity-potentiating polypeptide ("IPP") such as the heat shock protein HSP70, and their uses a immunogenic compositions to induce and enhance immune responses, primarily cytotoxic T lymphocyte responses to specific antigens such as tumor or viral antigens.

Description of the Background Art

Cytotoxic T lymphocytes (CTL) are critical effectors of anti-viral and antitumor responses (reviewed in Chen, C H et al., J Biomed Sci. 5: 231-252, 1998; Pardoll, D M. Nat Med. 4: 525-531, 1998; Wang, R F et al., Immunol Rev. 170: 85-100, 1999). Activated CTL are effector cells that mediate antitumor immunity by direct lysis of their target tumor cells or virus-infected cells and by releasing of cytokines that orchestrate immune and inflammatory responses that interfere with tumor growth or metastasis, or viral spread. Depletion of CD8$^+$ CTL leads to the loss of antitumor effects of several cancer vaccines (Lin, K-Y et al., Canc Res. 56: 21-26, 1996; Chen, C-H et al., Canc Res. 60: 1035-42, 2000). Therefore, the enhancement of antigen presentation through the MHC class I pathway to CD8$^+$ T cells has been a primary focus of cancer immunotherapy.

DNA vaccines have emerged as an attractive approach for antigen-specific cancer immunotherapy. DNA vaccines offer many advantages over more conventional vaccines, such as peptide or attenuated live pathogens. One advantage is that DNA vaccines are reasonably stable and can be easily prepared and harvested in large quantities. Additionally, naked plasmid DNA is relatively safe and can be repeatedly administered without adverse effects. Furthermore, because DNA is able to be maintained in cells for long-term expression of the encoded antigen, maintenance of immunologic memory is possible (for reviews, see Donnelly, J J et al., *Annu Rev Immunol* 1997, 15:617-648; Pardoll, D. M., *Nat Med* 1998, 4(5 Suppl):525-531; Robinson, H L, *Vaccine* 1997, 15:785-787; Gurunathan, S et al., *Annu Rev Immunol* 2000, 18:927-974).

However, one limitation of these vaccines is their lack of potency, since the DNA vaccine vectors generally do not have the intrinsic ability to be amplified and to spread in vivo as do some replicating viral vaccine vectors. Furthermore, some tumor antigens such as the E7 protein of human papillomavirus-16 ("HPV-16") are weak immunogens (Chen et al., 2000, supra). Therefore, there is a need in the art for strategies to enhance DNA vaccine potency, particularly for more effective cancer and viral immunotherapy.

Heat Shock Proteins

Cells respond to stressors (typically heat shock) by increasing the expression of a group of genes commonly referred to as stress, or heat shock, genes. As used herein, a "heat shock protein" (abbreviated either HSP or Hsp) or "stress protein," is encoded by a stress gene, and is therefore typically produced in significantly greater amounts upon the contact or exposure of the cell or organism to the stressor. A heat shock gene is a gene that is activated or otherwise detectably upregulated as a result of stressor exposure (which may include heat shock, hypoxia, glucose deprivation, a heavy metal salt, an inhibitor of energy metabolism and electron transport, and protein denaturant, or to certain benzoquinone ansamycins. See, for example, U.S. Pat. No. 6,524,825 and Nover, L., *Heat Shock Response*, CRC Press, Inc., Boca Raton, Fla. (1991), both of which are hereby incorporated by reference. Stress genes includes native homologues within known stress gene families, such as certain genes within the Hsp70 and Hsp90 stress gene families, even though not every homologue is induced by a stressor.

These proteins appear to participate in important cellular processes such as protein synthesis, intracellular trafficking, and assembly and disassembly of protein complexes. The increased amounts of stress proteins synthesized during stress serve primarily to minimize the consequences of induced protein unfolding. Indeed, the preexposure of cells to mildly stressful conditions that induce stress proteins protects the cells from the deleterious effects of more extreme forms of stress. The major stress proteins appear to be expressed in every organism and tissue type) examined so far. Moreover, they represent the most highly conserved group of proteins identified to date. For example, when stress proteins in widely diverse organisms are compared. Hsp90 and Hsp70 exhibit 50% or higher identity at the amino acid level and share many similarities at non-identical positions. Similar or greater homology exists between different members of a particular stress protein family within a species.

The predominant stress proteins in bacteria have molecular masses around 70 and 60 kDa, that are commonly referred to as Hsp70 and Hsp60, respectively. These represent about 1-3% of the total cell protein but accumulate to levels as high as 25% under stressful conditions.

Genes encoding stress proteins may be present in single or multiple, non-identical copies in a genome. For example, the human genome has at least one copy of an hsp100 gene, at least two different hsp90 genes, up to ten hsp70 genes of which at least several are non-identical copies, several T complex genes (Tcp genes) and at least one gene encoding the related mitochondrial protein Hsp60, as well as at least three copies of small hsp genes encoding Hsps of 20-30 kDa. Most families of stress genes include at least one member whose expression is relatively high and is either entirely constitutive or only mildly inducible. Furthermore, several families of stress genes include members that are not up-regulated by heat but are by other signals, e.g. increased calcium levels.

The stress proteins, particularly Hsp70, Hsp60, Hsp20-30 and Hsp10, are among the major determinants recognized by the immune system in response to infection by *M. tuberculosis* and *M. leprae* (Young, R A et al., Cell, 1989, 50:5-8. Even healthy individuals with no history of mycobacterial infection or autoimmune disease carry T cells that recognize both bacterial and human Hsp60 epitopes; a considerable fraction of T cells expressing the γδ T cell receptor recognize both self and foreign stress proteins (O'Brien, R et al. Cell, 1989 57:664-674 (1989). The "system" recognizing Hsp epitopes is considered to be an "early defense system" against invading microorganisms (Murray, P J et al., J. Bacteriol. 174:4193-6 (1992)) and may be maintained by frequent stimulation by bacteria and viruses. The safety of stress proteins is demonstrated by the success and relative safety of BCG (Bacille Calmette Guerin, a strain of *M. bovis*) vaccination, which induce an immune response against stress proteins that is cross-protective against *M. tuberculosis*.

Immunogenic Constructs with HPV E7 as a Model Antigen

The present inventors and their colleagues previously developed several intracellular targeting and intercellular spreading strategies to enhance DNA vaccine potency using various IPP's (Hung, C F et al., *J Virol* 2002, 76:2676-2682; Cheng, W F et al., *J Clin Invest* 2001, 108:669-678; Hung, C F et al., *J Immunol* 2001, 166:5733-5740; Chen, C H et al., *Gene Ther* 1999, 6:1972-1981; Ji, H et al., *Hum Gene Ther* 1999, 10:2727-2740; Chen, C H et al., *Cancer Res* 2000, 60:1035-1042; U.S. Pat. No. 6,734,173, WO 01/29233; WO03/085085; WO 02/012281; WO 02/061113, etc.). Among these strategies, the linkage of *Mycobacterium tuberculosis* heat shock protein 70 (HSP70) to human papillomavirus type 16 (HPV-16) E7 has been demonstrated to dramatically increase E7-specific $CD8^+$ T cell precursors and enhance anti-tumor effects against an E7-expressing tumor (TC-1) in vaccinated mice. These discoveries followed the earlier finding that immunization with HSP complexes isolated from tumor or virus-infected cells potentiated anti-tumor immunity (Janetzki, S et al., 1998. *J Immunother* 21:269-76) or antiviral immunity (Heikema, A E et al., *Immunol Lett* 57:69-74) Immunogenic HSP-peptide complexes could be reconstituted in vitro by mixing the peptides with HSPs (Ciupitu, A M et al., 1998. *J Exp Med* 187:685-91). Furthermore, HSP-based protein vaccines have been created by fusing antigens to HSPs (Suzue, K et al., 1996. *J Immunol* 156:873-879). The results of these investigations point to HSPs one attractive candidate for use in immunotherapy. However, prior to the present inventors' work, HSP vaccines were peptide/protein-based vaccines.

Moreover, the present inventors and their colleagues were the first to provide naked DNA and self-replicating RNA vaccines that incorporated HSP70 and other immunogenicity-potentiating polypeptides. The present inventors and their colleagues also demonstrated that linking antigen to intracellular targeting moieties calreticulin (CRT), domain II of *Pseudomonas aeruginosa* exotoxin A (ETA(dII)), or the sorting signal of the lysosome-associated membrane protein type 1 (Sig/LAMP-1) enhanced DNA vaccine potency compared to compositions comprising only DNA encoding the antigen of interest. To enhance MHC class II antigen processing, one of the present inventors and colleagues (Lin, K Y et al., 1996, *Canc Res* 56: 21-26) linked the sorting signals of the lysosome-associated membrane protein (LAMP-1) to the cytoplasmic/nuclear human papilloma virus (HPV-16) E7 antigen, creating a chimera (Sig/E7/LAMP-1). Expression of this chimera in vitro and in vivo with a recombinant vaccinia vector had targeted E7 to endosomal and lysosomal compartments and enhanced MHC class II presentation to CD4+ T cells. This vector was found to induce in vivo protection against an E7+ tumor, TC-1 so that 80% of mice vaccinated with the chimeric Sig/E7/LAMP1 vaccinia remained tumor free 3 months after tumor injection. Treatment with the Sig/E7/LAMP-1 vaccinia vaccine cured mice with small established TC-1 tumors, whereas the wild-type E7-vaccinia showed no effect on this established tumor burden. These findings point to the importance of adding an "element" to an antigenic composition to enhance in vivo potency of a recombinant vaccine: in this case, a polypeptide that rerouted a cytosolic tumor antigen to the endosomal/lysosomal compartment Intradermal administration of DNA vaccines via gene gun in vivo have proven to be an effective means to deliver such vaccines into professional antigen-presenting cells (APCs), primarily dendritic cells (DCs), which function in the uptake, processing, and presentation of antigen to T cells. The interaction between APCs and T cells is crucial for developing a potent specific immune response.

However, the various DNA or RNA constructs described by the present inventors or others in the prior art, have resulted in certain combinations that induced a heightened immune response in experimental animals. However, none of these vaccines have been ideally designed use in humans where administration may be limited for practical or other reasons to intramuscular injection. Because direct transduction of professional APCs in muscle tissue is not likely to occur due to paucity of such cells in muscle. That leaves cross-priming as the most likely mechanism for the induction of heightened immunity in humans. Optimizing vaccine constructs for cross priming requires that an element be added that promotes the secretion of the expressed polypeptide antigenic moiety, preferably as a fusion polypeptide with a molecule that promotes antigen processing via the MHC class I pathway. Moreover, it best to used plasmid constructs that are know to be safe and effective in humans. Finally, in the case of HPV oncoprotein antigens, it is also important to "detoxify" the protein that is to be expressed so that it will not act as an oncogenic transforming agent. It is to such constructs with the aforementioned advantageous properties that the present invention is directed.

SUMMARY OF THE INVENTION

The present inventors have designed and disclose herein an immunotherapeutic strategy that combines antigen-encoding DNA vaccine compositions which includes a signal peptide for secretion after initial uptake and expression, and a second protein, exemplified by HSP70, that promotes processing of the antigen via the MHC class I pathway and enhanced immunogenicity.

The growing understanding of the antigen presentation pathway creates the potential for designing novel strategies to enhance vaccine potency. One strategy taken by the present inventors in the present invention to enhance the presentation of antigen through the MHC class I pathway to $CD8^+$ T cells is the exploitation of the features of certain polypeptides to target antigenic polypeptide to which they are fused. Such polypeptide are referred to collectively herein as "immunogenicity-potentiating (or -promoting) polypeptide" or "IPP" to reflect this general property, even though these IPP's may act by any of a number of cellular and molecular mechanisms that may or may not share common steps. This designation is intended to be interchangeable with the term "targeting polypeptide." Inclusion of nucleic acid sequences that encode polypeptides that modify the way the antigen encoded by molecular vaccine is "received" or "handled" by the immune system serve as a basis for enhancing vaccine potency.

The present invention is directed to a nucleic acid molecule encoding a fusion polypeptide useful as a vaccine composition, which molecule comprises:
(a) a first nucleic acid sequence encoding a first polypeptide or peptide that promotes processing via the MHC class I pathway;
(b) fused in frame with the first nucleic acid sequence, a second nucleic acid sequence encoding a signal peptide; and
(c) a third nucleic acid sequence that is linked in frame to the first nucleic acid sequence and that encodes an antigenic polypeptide or peptide.

The antigenic peptide preferably comprises an epitope that binds to a MHC class I protein.

A preferred first polypeptide is Hsp70, an active C-terminal domain thereof, or a functional derivative of Hsp70 or of the C-terminal domain. Preferably this polypeptide is the *Mycobacterium tuberculosis* HSP70 and has the sequence SEQ ID NO:10 or is encoded by a nucleic acid SEQ ID NO:9.

The preferred antigenic polypeptide or peptide is one which is present on, or/cross-reactive with an epitope of, a pathogenic organism, cell, or virus, preferably human papilloma virus. Preferred antigens are the E7 polypeptide of HPV-16 having the sequence SEQ ID NO:2, or an antigenic fragment thereof, or the E6 HPV polypeptide having the sequence SEQ ID NO:4. The third nucleic acid sequence of the above construct preferably encodes a non-oncogenic mutant or variant of the E7 or E6 protein, or both in tandem.

The preferred nucleic acid molecule above is pNGVL4a-Sig/E7(detox)/HSP70, and has the sequence SEQ ID NO:13.

Above the nucleic acid molecules may be linked to a promoter. of claim 1 operatively linked to a promoter.

The invention also includes an expression vector comprising any nucleic acid molecule as above, operatively linked to (a) a promoter; and (b) optionally, additional regulatory sequences that regulate expression of the nucleic acid in a eukaryotic cell, preferably a human cell.

Also provided is a pharmaceutical composition capable of inducing or enhancing an antigen-specific immune response, comprising the above nucleic acid molecule or expression vector and pharmaceutically and immunologically acceptable excipient.

Also included is a method of inducing or enhancing an antigen specific immune response in a subject, preferably a human, comprising administering to the subject an effective amount of the above pharmaceutical composition, thereby inducing or enhancing the response. The response is preferably one mediated at least in part by $CD8^+$ CTL.

The above method preferably comprises administering the pharmaceutical composition by intramuscular injection, by gene gun administration or by needle-free jet injection.

The invention is also directed to a method of inhibiting growth or preventing re-growth of a tumor expressing HPV E7 or E6 protein in a subject, comprising administering to the subject an effective amount of the above pharmaceutical composition wherein the third nucleic acid sequence encodes one or more epitopes of E7 or E6, thereby inhibiting the growth or preventing the re-growth.

BRIEF DESCRIPTION OF THE DRAWINGS

FIG. 1A shows representative results of intracellular cytokine staining. The number of $CD8^+$ IFN-γ double-positive T cells in $3\times10^5$ splenocytes are indicated in the upper right corner. FIG. 1B shows composite result of flow cytometric analysis of IFN-γ-secreting E7-specific $CD8^+$ T cell precursors in naïve mice and mice vaccinated with pNGVL4a-Sig/E7(detox)/HSP70 DNA vaccine via needle i.m., biojector, and gene gun. Results are expressed as the mean number of number of E7-specific IFN-γ $CD8^+$ T lymphocytes per $3\times10^5$ splenocytes; bars, ±SE.

FIG. 2 is a graph showing in vivo tumor protection experiments that compare the antitumor effects of the vaccine delivered by different routes. Mice were immunized and challenged with $5\times10^4$ TC-1 tumor cells. Results are expressed as the percentage of tumor free mice at various days after tumor challenge.

FIG. 3 shows the number of pulmonary nodules present in naïve mice and in the groups of treated mice Results are expressed as the mean number of lung nodules; bars, ±SE. FIG. 4 shows weights of pulmonary nodules present in naïve mice and in groups of treated mice Results are expressed as the mean weight of lung nodules; bars, ±SE FIG. 5A is a schematic diagram of the pNGVL4a-Sig/E7 (detox)/HSP70 plasmid vector used for anti-tumor vaccination. FIG. 5B discloses SEQ ID NOs: 17-20, respectively, in order of appearance.

DESCRIPTION OF THE PREFERRED EMBODIMENTS

Partial List of Abbreviations Used

Figure 1A:
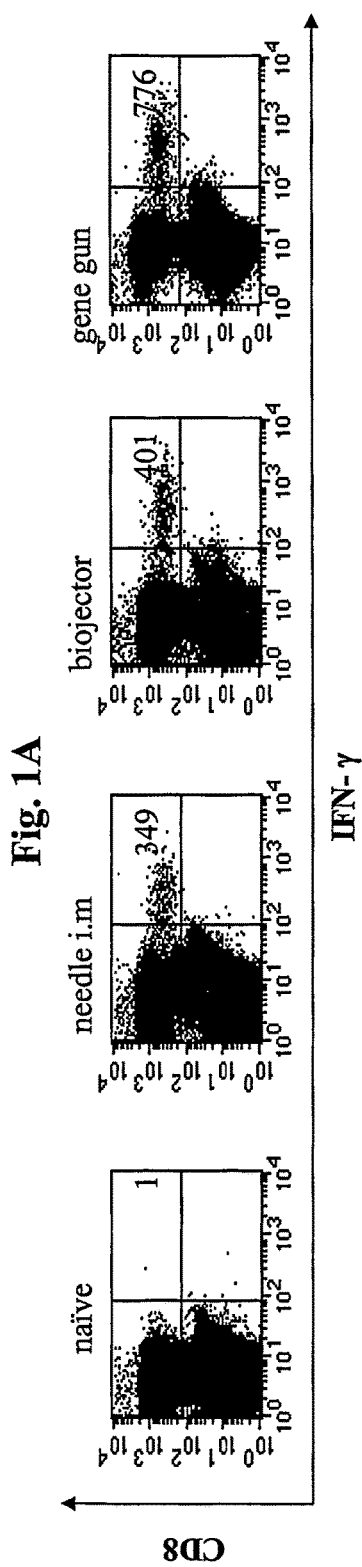
FIGS. 1A and 1B show intracellular cytokine staining and flow cytometric analysis characterizing IFN-γ-secreting E7-specific $CD8^+$ T cell precursors in mice vaccinated with pNGVL4a-Sig/E7(detox)/HSP70 DNA vaccine via needle i.m., biojector, and gene gun. Flow cytometric analysis was of splenocytes collected from vaccinated mice one week after vaccination. and cultured in vitro with or without the E7 peptide (amino acids 49-57) overnight. Cells were stained for both CD8 and intracellular IFN-γ. The number of IFN-γ secreting $CD8^+$ T cell precursors in naïve and immunized mice was analyzed.

APC, antigen presenting cell; CTL, cytotoxic T lymphocyte; DC, dendritic cell; ECD, extracellular domain; E6, HPV oncoprotein E6; E7, HPV oncoproteinE7; ELISA, enzyme-linked immunosorbent assay; HPV, human papillomavirus; HSP, heat shock protein; Hsp70, mycobacterial heat shock protein 70; IFNγ, interferon-γ; i.m., intramuscular(ly); i.v., intravenous(ly); MHC, major histocompatibility complex; PBS, phosphate-buffered saline; PCR, polymerase chain reaction; β-gal, β-galactosidase The present inventors and their colleagues have shown that the linkage of *Mycobacterium tuberculosis* heat shock protein 70 (HSP70) to human papillomavirus type 16 (HPV-16) oncoprotein E7 dramatically increased E7-specific $CD8^+$ T cell precursors and enhance anti-tumor effects against an E7-expressing tumor in vaccinated mice (Chen et al., 2000, supra; U.S. Pat. No. 6,734,173).

They have now adopted this strategy for Phase I/II clinical trials in patients with HPV-16 associated high-grade squamous intraepithelial lesion (HSIL) of the cervix and in patients with advanced HPV-associated head and neck squamous cell carcinoma (HNSCC). To do so, a GMP grade E7/HSP70 DNA vaccine was produced in the form of a naked DNA preparation based on the pNGVL4a plasmid (which plasmid was developed by the National Gene Vector Lab and has been approved for use in humans) The DNA molecule of the present invention has been termed "pNGVL4a-Sig/E7(detox)/HSP70)". A similar DNA vaccine for the E6 protein is also described below.

The pNGVL4a-Sig/E7(detox)/HSP70 DNA vaccine was generated using the pNGVL4a vector as a backbone. This vector was originally derived from the pNGVL3 vector, which has been approved for human vaccine trials. The pNGVL4a vector includes two immunostimulatory sequences (tandem repeats of CpG dinucleotides) in the noncoding region. Whereas any other plasmid DNA that can transform either APCs or other cells which, via cross-priming, transfer the antigenic moiety to APCs, is useful in the present invention, PNGFVLA4 is preferred because of the fact that it has already been approved for human therapeutic use.

The pNGVL4a-Sig/E7(detox)/HSP70 DNA vaccine also comprises a signal peptide (Sig) the purpose of which is to enhance the immune response to DNA immunizations via the intramuscular (i.m.) route. The Sig acts by facilitating release of a chimeric E7/HSP70 polypeptide from cells which have taken up and expressed the chimeric polypeptide encoded by the DNA construct. In the case of i.m. immunization, due to the absence in muscle of a high density of professional antigen presenting cells (APC) and the fact that injection of the DNA would not directly target APCs, it is desired to induce immunity via cross-priming. If the immunogenic protein, such as the E7/HSP70 chimeric polypeptide, cannot leave the cell in which it is made, primarily myocytes after i.m. injection, cross-priming will not occur. The Sig sequence is exploited to permit and promote secretion of the E7/HSP70 from the muscle cells in which it is first expressed. Any signal sequence known to promote the sorting of an attached peptide into the rough endoplasmic reticulum, resulting in processing for secretion, may be used in place of the "Sig" sequence [residues encoded by nucleotides 4056-4127?? of SEQ ID NO:13. In the process of protein secretion, amino-terminal signal sequences are key recognition elements (see below). The limits of variation permitted for functional signal sequences can readily be determined by replacement of the normal signal sequence of a protein that is naturally targeted for secretion, or a reporter protein (e.g., green fluorescent protein), with essentially random peptide sequences and testing for secretion. This has been done, for example, with yeast invertase by Kaiser C A et al., *Science* 1987, 235:312-317.

As a protein begins to be assembled, the very first amino acids in the polypeptide chain indicate whether the protein is to be secreted or used in the cytosol. If a protein is destined for secretion, the first amino acids are a special sequence called the signal sequence. The synthesis halts until the ribosome docks at the rough endoplasmic reticulum (RER). Once docked, the synthesis continues, with the new protein threading into the RER. The signal sequence is then cleaved from the polypeptide chain. Often, too, further enzymes cut the protein in other places. Most secreted proteins are modified before secretion. Next vesicles containing the protein bud from the RER and move to nearby the nearby Golgi apparatus. This is comprised of a stack of large, flattened vesicles. The vesicles from the RER fuse with one end, adding their proteins to the first flattened vesicle. In turn, small vesicles bud from this structure and transfer the protein to the next layer of the stack. This continues until the protein winds up at the opposite end of the Golgi apparatus. Further modification of the protein typically occurs here, for example, glycosylation (if the secreted protein is to be a glycoprotein). This renders the secreted protein more polar. Once the protein has moved through the entire Golgi apparatus, secretion vesicles containing the protein bud off, and move to and attach to the plasma membrane and release their contents into the extracellular fluid through the process of exocytosis.

The term "signal sequence" refers to a "signal peptide," which is a peptide sequence that directs post translational uptake by organelles. Signal peptides are about 16-32 amino acids long are cleaved while proteins are still being processed. Signal peptides consist of one or more positively charged amino acids followed by 6-12 hydrophobic amino acids. Examples of such signal sequence may be found in any textbook of biochemistry or cell biology, for example, Albers, B. et al., *Molecular Biology of the Cell*, 4th Ed., Garland Science, New York, N.Y. (2002). One of ordinary skill in the art will readily appreciate how to select a signal sequence for use in accordance with this invention (as a substitute for the preferred "Sig" sequence noted herein).

I.M. immunization with a secreted form of an antigen, i.e., that includes a signal peptide, will generate stronger CTL responses than i.m. immunization with a "cytoplasmic" form of antigen, suggesting that the priming of CTL responses after i.m. DNA immunization is facilitated by the cross-presentation of antigen by non-transfected professional APCs that have acquired the immunogen/antigen indirectly. See, for example, Boyle, J S et al., *Int Immunol* 1997, 9:1897-1906.

In addition, when an oncoprotein or an epitope thereof is the immunizing moiety, it is necessary to reduce the tumorigenic risk of the vaccine itself. In the preferred embodiments, the HPV E7 or E6 antigens are oncogenic. Thus the E7 protein was doubly mutated to a form known as "E7 (detox)" by substituting two amino acids at positions $C^{24}G$ (Cys→Gly) and $E^{26}G$ (Glu→Gly). See SEQ ID NO:2. These substitutions completely eliminate the capacity of the E7 to binding capacity to Rb, as well as transforming activity.

Another embodiment of the present invention comprises an antigenic epitope of the HPV E6 protein, preferably from HPV-16. The E6 proteins from cervical cancer-associated HPV types such as HPV-16 induce proteolysis of the p53 tumor suppressor protein through interaction with E6-AP. Human mammary epithelial cells (MECs) immortalized by E6 display low levels of p53. HPV-16 E6 as well as other cancer-related papillomavirus E6 proteins also binds the cellular protein E6BP (ERC-55). Several different E6 mutations are discussed below after the "wild type" sequence of E6 is presented. The studies describing these mutants (which are incorporated by reference in their entirety) are also discussed in that section.

The present invention also includes the use of a tandem E6-E7 vaccine, using one or more of the mutations described herein to render the oncoproteins inactive with respect to their oncogenic potential in vivo. Cassetti M C et al., Vaccine. 2004, 22:520-527, described Venezuelan equine encephalitis virus replicon particle (VRP) vaccines encoding the HPV16 E6 and E7 genes in which the E6 and E7 genes were fused to create one open reading frame and mutated at four or at five amino acid positions (see below). Thus, the present constructs may include one or more epitopes of E6 and E7, which may be arranged in their native order, resulting in either a E6-E7 or E7-E6 sequence, or shuffled in any way that permits the expressed protein to bear the E6 and E7 antigenic epitope(in an immunogenic form and result in immunization of the vaccinated recipient. DNA encoding amino acid spacers between E6 and E7 or between individual epitopes of these proteins may be introduced into the vector, provided again, that the spacers permit the expression or presentation of the epitopes in an immunogenic manner after they have been expressed by transduced host cells.

The order in which the two (or more) component polypeptides of the fusion protein are arranged, and therefore, the order of the encoding nucleic acid fragments in the nucleic acid vector, can be altered without affecting immunogenicity of the fusion polypeptides proteins and the utility of the composition. For example, the Hsp70-encoding DNA sequences may be located 5' or 3' to the target antigen-encoding sequences. In one embodiment, these polypeptide-encoding nucleic acid domains are in-frame so that the DNA construct encodes a recombinant fusion polypeptide in which the antigen is located N-terminal to the Hsp70 polypeptide. Of course, the signal peptide must be at the N-terminus of a nascent protein. Preferably, the DNA construct encodes a recombinant polypeptide in which the MHC class I restricted antigen, exemplified by mutant (detox) E7 (or E6) is located N-terminal to the HSP-derived residues.

Heat Shock Proteins and Homologues

Although the preferred DNA construct of the present invention encodes HSP70 from *M. tuberculosis*, any suitable heat shock protein (or stress protein) can be used in its place. Hsp60 and/or Hsp70 are preferred.

Families of stress genes and proteins that can be used in the present invention are those well known in the art and include, for example, Hsp100-200, Hsp100, Hsp90, Lon, Hsp70, Hsp60, TF55, Hsp40, FKBPs, cyclophilins, Hsp20-30, ClpP, GrpE, Hsp10, ubiquitin, calnexin, and protein disulfide isomerases (Macario, A J Cold Spring Harbor Laboratory Res. 25:59-70, 1995; Parsell, D A et al., *Ann. Rev. Genet.* 27:437-496 (1993); U.S. Pat. No. 5,232,833. A preferred group of stress proteins includes Hsp90, Hsp70, Hsp60, Hsp20-30; most preferred are Hsp70 and Hsp60.

Examples of Hsp100-200 include Grp170 (for glucose-regulated protein) which is found in the lumen of the ER, in the pre-Golgi compartment, and may play a role in immunoglobulin folding and assembly. Hsp100 members include mammalian Hsp110, yeast Hsp104, ClpA, ClpB, ClpC, ClpX and ClpY.

Examples of Hsp90 proteins include HtpG in *E. coli*, Hsp83 and Hsc83 yeast, and Hsp90α, Hsp90β and Grp94 in humans. Hsp90 binds cellular regulatory proteins such as steroid hormone receptors, transcription factors and protein kinases that play a role in signal transduction mechanisms. Hsp90 proteins also participate in the formation of large, abundant protein complexes that include other stress proteins.

Hsp70 examples include Hsp72 and Hsc73 from mammalian cells, products of the DnaK gene from bacteria, particularly mycobacteria such as *M. leprae, M. tuberculosis*, and *M. bovis* (such as BCG referred to herein as Hsp71), *E. coli*, other prokaryotes and yeast, and BiP and Grp78. Hsp70 can specifically binding ATP as well as unfolded polypeptides and peptides, thereby participating in protein folding and unfolding as well as in the assembly and disassembly of protein complexes.

Examples of Hsp60 proteins include Hsp65 from mycobacteria. Bacterial Hsp60 is also commonly known as GroEL, such as the GroEL from *E. coli*. Hsp60 forms large homo-oligomeric complexes, and appears to play a key role in protein folding. Hsp60 homologues are present in eukaryotic mitochondria and chloroplasts.

Examples of TF55 examples include Tcpl, TRiC and thermosome. The proteins typically occur in the cytoplasm of eukaryotes and some archaebacteria, and form multi-membered rings, promoting protein folding. They are also weakly homologous to Hsp60.

Examples of Hsp40 include DnaJ gene products from prokaryotes such as *E. coli* and mycobacteria and HSJ1, HDJ1 and Hsp40. Hsp40 plays a role as a molecular chaperone in protein folding, thermotolerance and DNA replication, among other cellular activities.

FKBPs examples include FKBP12, FKBP13, FKBP25, and FKBP59, Fprl and Nepl. The proteins typically have peptidyl-prolyl isomerase activity and interact with immunosuppressants such as FK506 and rapamycin. The proteins are typically found in the cytoplasm and the endoplasmic reticululum.

Cyclophilin examples include cyclophilins A, B and C. The proteins have peptidyl-prolyl isomerase activity and interact with the immunosuppressant cyclosporin A. The protein cyclosporin A binds calcineurin (a protein phosphatase).

Hsp20-30. also referred to as small Hsp, is typically found in large homo-oligomeric complexes or hetero-oligomeric complexes where an organism or cell expresses several different types of small Hsps. Hsp20-30 interacts with cytoskeletal structures, and may play a regulatory role in actin polymerization/depolymerization. Hsp20-30 is rapidly phosphorylated upon stressor exposure or exposure of resting cells to growth factors. Hsp20-30 homologues include α-crystallin.

ClpP is an *E. coli* protease involved in degradation of abnormal proteins. Homologues of ClpP are found in chloroplasts. ClpP forms a hetero-oligomeric complex with ClpA.

GrpE is an *E. coli* protein of about 20 kDa that is involved in both the rescue of stress-damaged proteins as well as the degradation of damaged proteins GrpE plays a role in the regulation of stress gene expression in *E. coli*.

Hsp10 examples include GroES and Cpn10. Hsp10 is typically found in *E. coli* and in mitochondria and chloroplasts of eukaryotic cells. Hsp10 forms a seven-membered ring that associates with Hsp60 oligomers. Hsp10 is also involved in protein folding.

Ubiquitin binds proteins in conjunction with proteolytic removal of the proteins by ATP-dependent cytosolic proteases.

In particular embodiments, the Hsp's of the present invention are derived from enterobacteria, mycobacteria (particularly *M. leprae, M. tuberculosis, M. vaccae, M. smegmatis* and *M. bovis*), *E. coli*, yeast, Drosophila, vertebrates, avians or mammals, including rats, mice and primates, including humans.

Homologues or variants of Hsp's as described herein, may also be used, provided that they have the requisite biological activity. These include various substitutions, deletions, or additions of the amino acid or nucleic acid sequences. Due to code degeneracy, for example, there may be considerable variation in nucleotide sequences encoding the same amino acid sequence.

The present invention may employ fragments of Hsp's provided such fragments can enhance the immune response to an antigen with which they are paired.

A preferred fragment is a C-terminal domain ("CD") of Hsp70, which is designated "Hsp70$_{CD}$". One Hsp70$_{CD}$ spans from about residue 312 to the C terminus of Hsp70 (SEQ ID NO:10). A preferred shorter polypeptide spans from about residue 517 to the C-terminus of SEQ ID NO:10. Shorter peptides from that sequence that have the ability to promote protein processing via the MHC-1 class I pathway are also included, and may be defined by routine experimentation.

A functional derivative of Hsp70 retains measurable Hsp70-like activity, preferably that of promoting immunogenicity of one or more antigenic epitopes fused thereto by promoting presentation by class I pathways. "Functional derivatives" encompass "variants" and "fragments" regardless of whether the terms are used in the conjunctive or the alternative herein.

A functional homologue must possess the above biochemical and biological activity. In view of this functional characterization, use of homologous Hsp70 proteins including proteins not yet discovered, fall within the scope of the invention if these proteins have sequence similarity and the recited biochemical and biological activity.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred method of alignment, Cys residues are aligned.

In a preferred embodiment, the length of a sequence being compared is at least 30%, preferably at least 40%, more preferably at least 50%, even more preferably at least 60%, and even more preferably at least 70%, 80%, or 90% of the length of the reference sequence (e.g., Hsp70, SEQ ID NO:10). The amino acid residues (or nucleotides) at corresponding amino acid (or nucleotide) positions are then compared. When a position in the first sequence is occupied by the same amino acid residue (or nucleotide) as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* 48:444-453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN prograth (version 2.0), using a PAM120 weight residue table, a gap length penalty of 12 and a gap penalty of 4.

The nucleic acid and protein sequences of the present invention can further be used as a "query sequence" to perform a search against public databases, for example, to identify other family members or related sequences. Such searches can be performed using the NBLAST and) XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to Hsp70 or FL nucleic acid molecules. BLAST protein searches can be performed with the XBLAST program, score=50, wordlength=3 to obtain amino acid sequences homologous to HVP22 protein molecules. To obtain gapped alignments for comparison purposes, Gapped BLAST can be utilized as described in Altschul et al. (1997) *Nucleic Acids Res.* 25:3389-3402. When utilizing BLAST and Gapped BLAST programs, the default parameters of the respective programs (e.g., XBLAST and NBLAST) can be used. See http://www.ncbi.nlm.nih.gov.

Thus, a homologue of Hsp70 described above is characterized as having (a) functional activity of native Hsp70 and (b) sequence similarity to a native Hsp70 protein (such as SEQ ID NO:10) when determined as above, of at least about 20% (at the amino acid level), preferably at least about 40%, more preferably at least about 70%, even more preferably at least about 90%.

It is within the skill in the art to obtain and express such a protein using DNA probes based on the disclosed sequences of Hsp70. Then, the fusion protein's biochemical and biological activity can be tested readily using art-recognized methods such as those described herein, for example, a T cell proliferation, cytokine secretion or a cytolytic assay, or an in vivo assay of tumor protection or tumor therapy. A biological assay of the stimulation of antigen-specific T cell reactivity will indicate whether the homologue has the requisite activity to qualify as a "functional" homologue.

A "variant" refers to a molecule substantially identical to either the full protein or to a fragment thereof in which one or more amino acid residues have been replaced (substitution variant) or which has one or several residues deleted (deletion variant) or added (addition variant). A "fragment" of Hsp70 refers to any subset of the molecule, that is, a shorter polypeptide of the full-length protein.

A number of processes can be used to generate fragments, mutants and variants of the isolated DNA sequence. Small subregions or fragments of the nucleic acid encoding the spreading protein, for example 1-30 bases in length, can be prepared by standard, chemical synthesis. Antisense oligonucleotides and primers for use in the generation of larger synthetic fragment.

A preferred group of variants are those in which at least one amino acid residue and preferably, only one, has been substituted by different residue. For a detailed description of protein chemistry and structure, see Schulz, G E et al., *Principles of Protein Structure*, Springer-Verlag, New York, 1978, and Creighton, T. E., *Proteins: Structure and Molecular Properties*, W.H. Freeman & Co., San Francisco, 1983, which are hereby incorporated by reference. The types of substitutions that may be made in the protein molecule may be based on analysis of the frequencies of amino acid changes between a homologous protein of different species, such as those presented in Table 1-2 of Schulz et al. (supra) and FIG. 3-9 of Creighton (supra). Based on such an analysis, conservative substitutions are defined herein as exchanges within one of the following five groups:

| | | |
|---|---|---|
| 1 | Small aliphatic, nonpolar or slightly polar residues | Ala, Ser, Thr (Pro, Gly); |
| 2 | Polar, negatively charged residues and their amides | Asp, Asn, Glu, Gln; |
| 3 | Polar, positively charged residues | His, Arg, Lys; |
| 4 | Large aliphatic, nonpolar residues | Met, Leu, Ile, Val (Cys) |
| 5 | Large aromatic residues | Phe, Tyr, Trp. |

The three amino acid residues in parentheses above have special roles in protein architecture. Gly is the only residue lacking a side chain and thus imparts flexibility to the chain. Pro, because of its unusual geometry, tightly constrains the chain. Cys can participate in disulfide bond formation, which is important in protein folding.

More substantial changes in biochemical, functional (or immunological) properties are made by selecting substitutions that are less conservative, such as between, rather than within, the above five groups. Such changes will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (i) substitution of Gly and/or Pro by another amino acid or deletion or insertion of Gly or Pro; (ii) substitution of a hydrophilic residue, e.g., Ser or Thr, for (or by) a hydrophobic residue, e.g., Leu, Ile, Phe, Val or Ala; (iii) substitution of a Cys residue for (or by) any other residue; (iv) substitution of a residue having an electropositive side chain, e.g., Lys, Arg or His, for (or by) a residue having an electronegative charge, e.g., Glu or Asp; or (v) substitution of a residue having a bulky side chain, e.g., Phe, for (or by) a residue not having such a side chain, e.g., Gly.

Most acceptable deletions, insertions and substitutions according to the present invention are those that do not produce radical changes in the characteristics of the wild-type or native protein in terms of its intercellular spreading activity and its ability to stimulate antigen specific T cell reactivity to an antigenic epitope or epitopes that are fused to the spreading protein. However, when it is difficult to predict the exact effect of the substitution, deletion or insertion in advance of doing so, one skilled in the art will appreciate that the effect can be evaluated by routine screening assays such as those described here, without requiring undue experimentation.

Whereas shorter chain variants can be made by chemical synthesis, for the present invention, the preferred longer chain variants are typically made by site-specific mutagenesis of the nucleic acid encoding the polypeptide, expression of the variant nucleic acid in cell culture, and, optionally, purification of the polypeptide from the cell culture, for example, by immunoaffinity chromatography using specific antibody immobilized to a column (to absorb the variant by binding to at least one epitope).

In the above composition the HSP70 or other stress protein preferably acts in potentiating an immune response by promoting: processing of the linked antigenic polypeptide via the MHC class I pathway or targeting of a cellular compartment that increases the processing. This basic strategy may be combined with an additional strategy pioneered by the present inventors and colleagues, that involve linking DNA encoding another protein, generically termed a "targeting polypeptide, to the antigen-encoding DNA. Again, for the sake of simplicity, the DNA encoding such a targeting polypeptide will be referred to herein as a "targeting DNA." That strategy has been shown to be effective in enhancing the potency of the vectors carrying only antigen-encoding DNA. See for example: Wu et al., WO 01/29233; Wu et al., WO 02/009645; Wu et al., WO 02/061113; Wu et al., WO 02/074920; Wu et al., WO 02/12281, all of which are incorporated by reference in their entirety. The other strategies include the use of DNA encoding polypeptides that promote or enhance:

(a) development, accumulation or activity of antigen presenting cells or targeting of antigen to compartments of the antigen presenting cells leading to enhanced antigen presentation;
(b) intercellular transport and spreading of the antigen; or
(c) any combination of (a) and (b).
(d) sorting of the lysosome-associated membrane protein type 1 (Sig/LAMP-1)
(e) a viral intercellular spreading protein selected from the group of herpes simplex virus-1 VP22 protein, Marek's disease virus VP22 protein or a functional homologue or derivative thereof;
(f) an endoplasmic reticulum chaperone polypeptide selected from the group of calreticulin, ER60, GRP94, gp96, or a functional homologue or derivative thereof.
(g) a cytoplasmic translocation polypeptide domains of a pathogen toxin selected from the group of domain II of *Pseudomonas* exotoxin ETA or a functional homologue or derivative thereof;
(h) a polypeptide that targets the centrosome compartment of a cell selected from γ-tubulin or a functional homologue or derivative thereof; or
(i) a polypeptide that stimulates dendritic cell precursors or activates dendritic cell activity selected from the group of GM-CSF; Flt3-ligand extracellular domain, or a functional homologue or derivative thereof; or
(j) a costimulatory signal, such as a B7 family protein, including B7-DC (see U.S. Ser. No. 09/794,210), B7.1, B7.2, soluble CD40, etc.).
(k) an anti-apoptotic polypeptide preferably selected from the group consisting of (1) BCL-xL, (2) BCL2, (3) XIAP, (4) FLICEc-s, (5) dominant-negative caspase-8, (6) dominant negative caspase-9, (7) SPI-6, and (8) a functional homologue or derivative of any of (1)-(7).

The details of the various targeting polypeptide strategies will not be discussed in detail herein, although such vectors are used in the present examples, and their sequences are provided below. The preferred "targeting polypeptide" include the sorting signal of the lysosome-associated membrane protein type 1 (Sig/LAMP-1), which is the "Sig" in the preferred construct, the translocation domain (domain II or dII) of *Pseudomonas aeruginosa* exotoxin A (ETA(dII) (or from similar toxins from *Diphtheria, Clostridium, Botulinum, Bacillus, Yersinia, Vibrio cholerae*, or *Bordetella*), an endoplasmic reticulum chaperone polypeptide exemplified by calreticulin (CRT) but also including ER60, GRP94 or gp96, well-characterized ER chaperone polypeptide that representatives of the HSP90 family of stress-induced proteins (see WO 02/012281), VP22 protein from herpes simplex virus and related herpes viruses such as Marek's disease virus (see WO 02/09645), and γ-tubulin. DNA encoding each of these polypeptides, or fragments or variants thereof with substantially the same biological activity, when linked to an antigen-encoding or epitope-encoding DNA molecule, and an HSP70 sequence result in more potent T cell mediate responses to the antigen compared to immunization with the antigen-encoding DNA alone or the antigen-HSP-70 chimeric construct. These polypeptide can be considered as "molecular adjuvants." These effects are manifest primarily with CD8+ T cells, although some of these approaches induce potent CD4+ T cell mediated effects as well.

The experiments described herein demonstrate that the methods of the invention can enhance a cellular immune response, particularly, tumor-destructive CTL reactivity, induced by a DNA vaccine encoding an epitope of a human pathogen. Human HPV-16 E7 was used as a model antigen for vaccine development because human papillomaviruses (HPVs), particularly HPV-16, are associated with most human cervical cancers. The oncogenic HPV proteins E7 and E6 are important in the induction and maintenance of cellular transformation and co-expressed in most HPV-containing cervical cancers and their precursor lesions. Therefore, cancer vaccines, such as the compositions of the invention, that target E7 or E6 can be used to control of HPV-associated neoplasms (Wu (1994) *Curr. Opin. Immunol.* 6:746-754).

However, the present invention is not limited to the exemplified antigen(s). Rather, one of skill in the art will appreciate that the same results are expected for any antigen (and epitopes thereof) for which a T cell-mediated response is desired. The response so generated will be effective in providing protective or therapeutic immunity, or both, directed to an organism or disease in which the epitope or antigenic determinant is involved—for example as a cell surface antigen of a pathogenic cell or an envelope or other antigen of a pathogenic virus, or a bacterial antigen, or an antigen expressed as or as part of a pathogenic molecule.

Thus, in one embodiment, the antigen (e.g., the MHC class I-binding peptide epitope) is derived from a pathogen, e.g., it comprises a peptide expressed by a pathogen. The pathogen can be a virus, such as, e.g., a papilloma virus, a herpesvirus, a retrovirus (e.g., an immunodeficiency virus, such as HIV-1), an adenovirus, and the like. The papilloma virus can be a human papilloma virus; for example, the antigen (e.g., the Class I-binding peptide) can be derived from an HPV-16 E6 or E7 polypeptide. In a preferred embodiment, the HPV-16 E6 or E7 polypeptide used as an immunogen is substantially non-oncogenic, i.e., it does not bind retinoblastoma polypeptide (pRB) or binds pRB with such low affinity that the HPV-16 E7 polypeptide is effectively non-oncogenic when expressed or delivered in vivo, which is accomplished as described herein.

In alternative embodiments, the pathogen is a bacteria, such as *Bordetella pertussis*; *Ehrlichia chaffeensis*; *Staphylococcus aureus*; *Toxoplasma gondii*; *Legionella pneumophila*; *Brucella suis*; *Salmonella enterica*; *Mycobacterium avium*; *Mycobacterium tuberculosis*; *Listeria monocytogenes*; *Chlamydia trachomatis*; *Chlamydia pneumoniae*; *Rickettsia rickettsii*; or, a fungus, such as, e.g., *Paracoccidioides brasiliensis*; or other pathogen, e.g., *Plasmodium falciparum*.

In another embodiment, the WIC class I-binding antigenic peptide epitope is derived from a tumor cell. The tumor cell-derived peptide epitope can comprise a tumor associated antigen, e.g., a tumor specific antigen, such as, e.g., a HER-2/neu antigen, or one of a number of known melanoma antigens, etc.

In one embodiment, the isolated or recombinant nucleic acid molecule is operatively linked to a promoter, such as, e.g., a constitutive, an inducible or a tissue-specific promoter. The promoter can be expressed in any cell, including cells of the immune system, including, e.g., antigen presenting cells (APCs), e.g., in a constitutive, an inducible or a tissue-specific manner.

Unless defined otherwise, all technical and scientific terms used herein have the meaning commonly understood by a person skilled in the art of this invention. As used herein, the following terms have the meanings ascribed to them unless specified otherwise.

The term "antigen" or "immunogen" as used herein refers to a compound or composition comprising a peptide, polypeptide or protein which is "antigenic" or "immunogenic" when administered (or expressed in vivo by an administered nucleic acid, e.g., a DNA vaccine) in an appropriate amount (an "immunogenically effective amount"), i.e., capable of inducing, eliciting, augmenting or boosting a cellular and/or humoral immune response either alone or in combination or linked or fused to another substance (which can be administered at once or over several intervals). An immunogenic composition can comprise an antigenic peptide of at least about 5 amino acids, a peptide of 10 amino acids in length, a polypeptide fragment of 15 amino acids in length, 20 amino acids in length or longer. Smaller immunogens may require presence of a "carrier" polypeptide e.g., as a fusion protein, aggregate, conjugate or mixture, preferably linked (chemically or otherwise) to the immunogen. The immunogen can be recombinantly expressed from a vaccine vector, which can be naked DNA comprising the immunogen's coding sequence operably linked to a promoter, e.g., an expression cassette as described herein. The immunogen includes one or more antigenic determinants or epitopes which may vary in size from about 3 to about 15 amino acids.

The term "vaccine" is used interchangeably with "immunogen" when referring to the DNA compositions of the present invention. Similarly, the terms "vaccinate" and "immunize" are used interchangeably here.

The term "epitope" as used herein refers to an antigenic determinant or antigenic site that interacts with an antibody or a T cell receptor (TCR), e.g., the MHC class I-binding peptide compositions (or expressed products of the nucleic acid compositions of the invention) used in the methods of the invention. An "antigen" is a molecule or chemical structure that either induces an immune response or is specifically recognized or bound by the product or mediator of an immune response, such as an antibody or a CTL. The specific conformational or stereochemical "domain" to which an antibody or a TCR bind is an "antigenic determinant" or "epitope." TCRs bind to peptide epitopes which are physically associated with a third molecule, a major histocompatibility complex (MHC) class I or class II protein.

The term "recombinant" refers to (1) a nucleic acid or polynucleotide synthesized or otherwise manipulated in vitro, (2) methods of using recombinant DNA technology to produce gene products in cells or other biological systems, or (3) a polypeptide encoded by a recombinant nucleic acid. For example, the HSP70-encoding nucleic acid or polypeptide, the nucleic acid encoding an MHC class I-binding peptide epitope (antigen) or the peptide itself can be recombinant. "Recombinant means" includes ligation of nucleic acids having various coding regions or domains or promoter sequences from different sources into a single unit in the form of an expression cassette or vector for expression of the coding sequences in the vectors resulting in production of the encoded polypeptide.

The term "self-replicating RNA replicon" refers to a construct based on an RNA viruses, such as alphavirus genome RNAs (e.g., Sindbis virus, Semliki Forest virus, etc.), that have been engineered to allow expression of heterologous RNAs and proteins. These recombinant vectors are self-replicating ("replicons") which can be introduced into cells as naked RNA or DNA, as described in detail in co-pending, commonly assigned U.S. and PCT patent applications by several of the present inventors (U.S. Ser. No. 10/060,274, and WO 02/061113).

Sequences of Polypeptides and Nucleic Acids

Plasmid and Vector Sequences

The wild-type HPV E7 sequence (nucleotide sequence is SEQ ID NO:1 used in the present invention, albeit with several mutations, and the wild-type amino acid sequence is SEQ ID NO:2) is shown below. Underlined codons and amino acids are those which are preferably mutated in the present constructs.

```
1/1                                     31/11
atg cat gga gat aca cct aca ttg cat gaa tat atg tta gat ttg caa cca gag aca act
Met His Gly Asp Thr Pro Thr Leu His Glu Tyr Met Leu Asp Leu Gln Pro Glu Thr Thr 61/21                                   91/31
gat ctc tac tgt tat gag caa tta aat gac agc tca gag gag gag gat gaa ata gat ggt
Asp Leu Tyr Cys Tyr Glu Gln Leu Asn Asp ser Ser Glu Glu Glu Asp Glu Ile Asp Gly 121/41                                  151/51
cca gct gga caa gca gaa ccg gac aga gcc cat tac aat att gta acc ttt tgt tgc aag
Pro Ala Gly Gln Ala Glu Pro Asp Arg Ala His Tyr Asn Ile Val Thr Phe Cys Cys Lys 181/61                                  211/71
tgt gac tct acg ctt cgg ttg tgc gta caa agc aca cac gta gac att cgt act ttg gaa
Cys Asp Ser Thr Leu Arg Leu Cys Val Gln Ser Thr His Val Asp Ile Arg Thr Leu Glu 241/81                                  271/91
gac ctg tta atg ggc aca cta gga att gtg tgc ccc atc tgt tct cag gat aag ctt
Asp Leu Leu Met Gly Thr Leu Gly Ile Val Cys Pro Ile Cys Ser Gln Asp Lys Leu
```

The above sequence differs from the GENEBANK Accession Number NC_001526 for the E7 protein which is:

(SEQ ID NO: 3)
MHGDTPTLHE YMLDLQPETT DLYCYEQLND SSEEEDEIDG

PAGQAEPDRA HYNIVTFCCK CDSTLRLCVQ STHVDIRTLE

DLLMGTLGIV CPICSQKP 97

The HPV16 E7 protein binds Rb through an L-X-C-X-E motif. Mutations at positions Cys24 and Glu26 of this motif destroy Rb binding and degradation. In addition to these two point mutations in E7, a mutation at a third amino acid, Cys91, destroys the single zinc finger in E7. In a preferred embodiment, all wild type amino acids are mutated to Gly. In another embodiment, these residues are mutated to Ala. In fact, they can be mutated to any residue that will permit the protein to be expressed in transduced cells, secreted in immunogenic form, taken up by professional APCs, and presented to T cells in a way that will preserve antigenic specificity, while at the same time preventing or lowering the probability that the protein will have oncogenic transforming capacity. The above statement is true with respect to the HPV E6 protein described below.

To reduce oncogenic potential of E7 in a construct of this invention, one or more of the following positions of E7 is mutated:

| Original residue | Mutant residue | Preferred codon mutation | Position in SEQ ID NO: 2 |
|---|---|---|---|
| Cys | Gly (or Ala) | TGT→GGT | 24 |
| Glu | Gly (or Ala) | GAG→GGG (or GCG) | 26 |
| Cys | Gly (or Ala) | TGC→GGC | 91 |

The E7 (detox) mutant sequence included in the preferred vaccine vector (SEQ ID NO:13) has the mutations shown in FIG. 5B—namely—a tgt→ggt mutation resulting in a Cys→Gly substitution at position 24 of SEQ ID NO:2 and a gag→ggg mutation resulting in a Glu→Gly substitution at position 26 or SEQ ID NO:2.

E6 Protein

The wild type HPV E6 amino acid sequence (GENEBANK Accession Number NC_001526) (SEQ ID NO:4) is shown below. This sequence has 158 amino acids.

MHQKRTAMFQ DPQERPRKLP QLCTELQTTI HDIILECVYC

KQQLLRREVY DFAFRDLCIV YRDGNPYAVC DKCLKFYSKI

SEYRHYCYSL YGTTLEQQYN KPLCDLLIRC INCQKPLCPE

EKQRHLDKKQ RFHNIRGRWT GRCMSCCRSS RTRRETQL

The preferred amino acid residues to be mutated (as discussed below) are underscored above. The studies of E6 mutants discussed below are based upon a different E6 sequence, of 151 nucleic acids, wherein the N-terminal residue was considered to be the Met at position 8 in SEQ ID NO:4. That shorter version of E6 is shown below as SEQ ID NO:5.

MFQDPQERPR KLPQLCTELQ TTIHDIILEC VYCKQQLLRR

EVYDFAFRDL CIVYRDGNPY AVCDKCLKFY SKISEYRHYC

YSLYGTTLEQ QYNKPLCDLL IRCINCQKPL CPEEKQRHLD

KKQRFHNIRG RWTGRCMSCC RSSRTRRETQ L

The preferred amino acid residues to be mutated (as discussed below) are underscored above.

Any nucleotide sequence that encodes encoding this E6 polypeptide, or preferably, one of the mutants thereof discussed below, or an antigenic fragment or epitope thereof, can be used in the present vectors. Other mutations can be tested and used in accordance with the methods described herein, or those described by Cassatti et al., supra.

To reduce oncogenic potential of E6 in a construct of this invention, one or more of the following positions of E6 is mutated:

| Original residue | Mutant residue | Position in SEQ ID NO: 4 | Position in SEQ ID NO: 5 |
|---|---|---|---|
| Ile | Thr | 135 | 128 |
| Cys | Gly (or Ala) | 70 | 63 |
| Cys | Gly (or Ala) | 113 | 106 |

These mutations can be achieved using any appropriate coding sequences by mutation of the coding DNA.

The studies describing these mutants (which are incorporated by reference in their entirety) are discussed below. Nguyen M et al., *J Virol.* 2002, 6:13039-13048, described a mutant of HPV-16 E6 deficient in binding α-helix partners which displays reduced oncogenic potential in vivo. This mutant, that involves a replacement of Ile with Thr as position 128 (of SEQ ID NO:5), may be used in accordance with the present invention to make an E6 DNA vaccine that has a lower risk of being oncogenic. This E6($I^{128}T$) mutant is defective for binding at least a subset of the α-helix partners, including E6AP, the ubiquitin ligase that mediates E6-dependent degradation of the p53 protein, Cassetti et al., supra, examined the effects of mutations four or five amino acid positions in E6 and E7 to inactivate their oncogenic potential. The following mutations were examined (positions based on SEQ ID NO:5): E6-$C^{63}G$; E6 $C^{106}G$; E7-$C^{24}G$, E7-$E^{26}G$, and E7 $C^{91}G$. Vaccines encoding mutant or wild type E6 and E7 proteins elicited comparable CTL responses and generated comparable antitumor responses in several HPV16 E6(+)E7(+) tumor challenge models: protection from either C3 or TC-1 tumor challenge was observed in 100% of vaccinated mice. Eradication of C3 tumors was observed in approximately 90%. The predicted inactivation of E6 and E7 oncogenic potential was confirmed by demonstrating normal levels of both p53 and Rb proteins in human mammary epithelial cells infected with VRP expressing mutant E6 and E7 genes.

Approaches for Mutagenesis of E6 and E7

The HPV16 E6 protein contains two zinc fingers important for structure and function; one cysteine (C) amino acid position in each pair of C—X—X—C (where X is any amino acid) zinc finger motifs are preferably was mutated at E6 positions 63 and 106 (based on SEQ ID NO:5). Mutants are created, for example, using the Quick Change Site-Directed Mutagenesis Kit (Stratagene, La Jolla, Calif.). HPV16 E6 containing a single point mutation at Cys106 (of Cys 113 per SEQ ID NO:4). Cys neither binds nor facilitates degradation of p53 and is incapable of immortalizing human mammary epithelial cells (MEC), a phenotype dependent upon p53 degradation. A single amino acid substitution at position Cys63 of SEQ ID NO:3 (=Cys70 in SEQ ID NO:4) destroys several HPV16 E6 functions: p53 degradation, E6TP-1 degradation, activation of telomerase, and, consequently, immortalization of primary epithelial cells.

Sequences of DNA Encoding Immunogenicity-Potentiating Polypeptides and their Vectors The preferred nucleotide [SEQ ID NO:6] and amino acid sequence [SEQ ID NO:7] of Sig/E7 are as follows: the Sig sequence is underscored:

MAAPGARRPL LLLLLAGLAH GASALFEDLI MHGDTPTLHE

YMLDLQPETT DLYCYEQLND SSEEEDEIDG PAGQAEPDRA

HYNIVTFCCK CDSTLRLCVQ STHVDIRTLE DLLMGTLGIV CPICSQP

A preferred nucleic acid sequence encoding a 30 residue Sig sequence is shown below (SEQ ID NO:8).

atg gcg gcc ccc ggc gcc cgg cgg ccg ctg ctc ctg ctg ctg ctg gca ggc ctt gca cat ggc gcc tca gca ctc ttt gag gat cta atc In another embodiment, the sequence is a C-terminally truncated version of SEQ ID NO:8, encoding from about 15-25 of the N-terminal residues of SEQ ID NO:8. As noted elsewhere, any known signal sequence may be substituted for this one in the present construct.

HSP70 from *M. tuberculosis*

The nucleotide sequence encoding HSP70 (SEQ ID NO:9) is shown below and is deposited in GENBANK; nucleotides 10633-12510 of the *M. tuberculosis* genome.

```
atggctcg tgcggtcggg atcgacctcg ggaccaccaa ctccgtcgtc tcggttctgg aaggtggcga cccggtcgtc tcggccaact ccgagggctc caggaccacc ccgtcaattg tcgcgttcgc ccgcaacggt gaggtgctgg tcggccagcc cgccaagaac caggcagtga ccaacgtcga tcgcaccgtg cgctcggtca agcgacacat gggcagcgac tggtccatag agattgacgg caagaaatac accgcgccgg agatcagcgc accgcattctg tgaagctga agcgcgacgc cgaggcctac ctcggtgagg acattaccga cgcggttatc acgacgcccg cctacttcaa tgacgcccag cgtcaggcca ccaaggacgc cggccagatc gccggcctca acgtgctgcg gatcgtcaac gagccgaccg cggccgcgct ggcctacggc ctcgacaagg gcgagaagga gcagcgaatc ctggtcttcg acttgggtgg tggcactttc gacgtttccc tgctggagat cggcgagggt gtggttgagg tccgtgccac ttcgggtgac aaccacctcg gcggcgacga ctgggaccag cgggtcgtcg attggctggt ggacaagttc aagggcacca gcggcatcga tctgaccaag gacaagatgg cgatgcagcg gctgcgggaa gccgccgaga aggcaaagat cgagctgagt tcgagtcagt ccacctcgat caacctgccc tacatcaccg tcgacgccga caagaacccg ttgttcttag acgagcagct gacccgcgcg gagttccaac ggatcactca ggacctgctg gaccgcactc gcaagccgtt ccagtcggtg atcgctgaca ccggcatttc ggtgtcggag atcgatcacg ttgtgctcgt gggtggttcg acccggatgc ccgcggtgac cgatctggtc aaggaactca ccggcggcaa ggaacccaac aagggcgtca accccgatga ggttgtcgcg gtgggagccg ctctgcaggc cggcgtcctc aagggcgagg tgaaagacgt tctgctgctt gatgttaccc cgctgagcct gggtatcgag accaaggggc gggtgatgac caggctcatc gagcgcaaca ccacgatccc caccaagcgg tcggagactt tcaccaccgc cgacgacaac caaccgtcgg tgcagatcca ggtctatcag ggggagcgtg agatcgccgc gcacaacaag ttgctcgggt ccttcgagct gaccggcatc ccgccggcgc cgcgggggat tccgcagatc gaggtcactt tcgacatcga cgccaacggc attgtgcacg tcaccgccaa ggacaagggc accggcaagg agaacacgat ccgaatccag gaaggctcgg gcctgtccaa ggaagacatt gaccgcatga tcaaggacgc cgaagcgcac gccgaggagg atcgcaagcg tcgcgaggag
```

```
gccgatgttc gtaatcaagc cgagacattg gtctaccaga cggagaagtt cgtcaaagaa cagcgtgagg ccgagggtgg ttcgaaggta cctgaagaca cgctgaacaa ggttgatgcc gcggtggcgg aagcgaaggc ggcacttggc ggatcggata tttcggccat caagtcggcg atggagaagc tgggccagga gtcgcaggct ctggggcaag cgatctacga agcagctcag gctgcgtcac aggccactgg cgctgcccac cccggcggcg agccgggcgg tgcccacccc ggctcggctg atgacgttgt ggacgcggag gtggtcgacg acggccggga ggccaagtga
```

The amino acid sequence of HSP70 [SEQ ID NO:10] is:

```
MARAVGIDLG TTNSVVSVLE GGDPVVVANS EGSRTTPSIV
AFARNGEVLV GQPAKNQAVT NVDRTVRSVK RHMGSDWSIE
IDGKKYTAPE ISARILMKLK RDAEAYLGED ITDAVITTPA
YFNDAQRQAT KDAGQIAGLN VLRIVNEPTA AALAYGLDKG
EKEQRILVFD LGGGTFDVSL LEIGEGVVEV RATSGDNHLG
GDDWDQRVVD WLVDKFKGTS GIDLTKDKMA MQRLREAAEK
AKIELSSSQS TSINLPYITV DADKNPLFLD EQLTRAEFQR
ITQDLLDRTR KPFQSVIADT GISVSEIDHV VLVGGSTRMP
AVTDLVKELT GGKEPNKGVN PDEVVAVGAA LQAGVLKGEV
KDVLLLDVTP LSLGIETKGG VMTRLIERNT TIPTKRSETF
TTADDNQPSV QIQVYQGERE IAAHNKLLGS FELTGIPPAP
RGIPQIEVTF DIDANGIVHV TAKDKGTGKE NTIRIQEGSG
LSKEDIDRMI KDAEAHAEED RKRREEADVR NQAETLVYQT
EKFVKEQREA EGGSKVPEDT KNKVDAAVAE AKAALGGSDI
SAIKSAMEKL GQESQALGQA IYEAAQAASQ ATGAAHPGGE
PGGAHPGSAD DVVDAEVVDD GREAK 625
```

A preferred E7-Hsp70 chimera or fusion (nucleic acid is SEQ ID NO:11; amino acids are SEQ ID NO:12) is shown below (using the wild-type E7 coding sequence which is capitalized, is shown below. For the present construct, the relevant codons/residues discussed above are mutated as described.

```
1/1                      31/11
ATGCATGGAGATACACCTACATTGCATGAATATATGTTAGATTTGCAACCAGAGACAACT
Met his gly asp thr pro thr leu his glu tyr met leu asp leu gln pro glu thr thr 61/21                    91/31
GATCTCTACTGTTATGAGCAATTAAATGACAGCTCAGAGGAGGAGGATGAAATAGATGGT
asp ley tyr cys tyr glu gln leu asp asp ser ser glu glu glu asp glu ile asp gly 121/41                   151/51
CCAGCTGGACAAGCAGAACCGGACAGAGCCCATTACAATATTGTAACCTTTTGTTGCAAG
pro ala gly gln ala glu pro asp arg ala his tyr asn ile val thr phe cys cys lys 181/61                   211/71
TGTGACTCTACGCTTCGGTTGTGCGTACAAAGCACACACGTAGACATTCGTACTTTGGAA
cys asp ler thr leu arg leu cys val gln ser thr his val asp ile arg thr leu glu 241/81                   271/91
GACCTGTTAATGGGCACACTAGGAATTGTGTGCCCCATCTGTTCTCAAGGATCC atg gct
asp leu leu met gly thr leu gly ile val cys pro ile cys ser gln gly ser met ala 301/101                  331/111
cgt gcg gtc ggg atc gac ctc ggg acc acc aac tcc gtc gtc tcg gtt ctg gaa ggt ggc
arg ala val gly ile asp leu gly thr thr asn ser val val ser val leu glu gly gly 361/121                  391/131
gac ccg gtc gtc gtc gcc aac tcc gag ggc tcc agg acc acc ccg tca att gtc gcg ttc
asp pro val val val ala asn ser glu gly ser arg thr thr pro ser ile val ala phe 421/141                  451/151
gcc cgc aac ggt gag gtg ctg gtc ggc cag ccc gcc aag aac cag gca gtg acc aac gtc
ala arg asn gly glu val leu val gly gln pro ala lys asn gln ala val thr asn val 481/161                  511/171
gat cgc acc gtg cgc tcg gtc aag cga cac atg ggc agc gac tgg tcc ata gag att gac
asp arg thr val arg ser val lys arg his met gly ser asp trp ser ile glu ile asp 541/181                  571/191
ggc aag aaa tac acc gcg ccg gag atc agc gcc cgc att ctg atg aag ctg aag cgc gac
gly lys lys tyr thr ala pro glu ile ser ala arg ile leu met lys leu lys arg asp 601/201                  631/211
gcc gag gcc tac ctc ggt gag gac att acc gac gcg gtt atc acg acg ccc gcc tac ttc
ala glu ala tyr leu gly glu asp ile thr asp ala val ile thr thr pro ala tyr phe 661/221                  691/231
aat gac gcc cag cgt cag gcc acc aag gac gcc ggc cag atc gcc ggc ctc aac gtg ctg
asn asp ala gln arg gln ala thr lys asp ala gly gln ile ala gly leu asn val leu
```

```
721/241                            751/251
cgg atc gtc aac gag ccg acc gcg gcc gcg ctg gcc tac ggc ctc gac aag ggc gag aag
arg ile val asn glu pro thr ala ala ala leu ala tyr gly leu asp lys gly glu lys 781/261                            811/271
gag cag cga atc ctg gtc ttc gac ttg ggt ggt ggc act ttc gac gtt tcc ctg ctg gag
glu gln arg ile leu val phe asp leu gly gly gly thr phe asp val ser leu leu glu 841/281                            871/291
atc ggc gag ggt gtg gtt gag gtc cgt gcc act tcg ggt gac aac cac ctc ggc ggc gac
ile gly glu gly val val glu val arg ala thr ser gly asp asn his leu gly gly asp 901/301                            931/311
gac tgg gac cag cgg gtc gtc gat tgg ctg gtg gac aag ttc aag ggc acc agc ggc atc
asp trp asp gln arg val val asp trp leu val asp lys phe lys gly thr ser gly ile 961/321                            991/331
gat ctg acc aag gac aag atg gcg atg cag cgg ctg cgg gaa gcc gcc gag aag gca aag
asp leu thr lys asp lys met ala met gln arg leu arg glu ala ala glu lys ala lys 1021/341                           1051/351
atc gag ctg agt tcg agt cag tcc acc tcg atc aac ctg ccc tac atc acc gtc gac gcc
ile glu leu ser ser ser gln ser thr ser ile asn leu pro tyr ile thr val asp ala 1081/361                           1111/371
gac aag aac ccg ttg ttc tta gac gag cag ctg acc cgc gcg gag ttc caa cgg atc act
asp ley asn pro leu phe leu asp glu gln leu thr arg ala glu phe gln arg ile tyr 1141/381                           1171/391
cag gac ctg ctg gac cgc act cgc aag ccg ttc cag tcg gtg atc gct gac acc ggc att
gln asp leu leu asp arg thr arg lys pro phe gln ser val ile ala asp thr gly ile 1201/401                                       1231/411
tcg gtg tcg gag atc gat cac gtt gtg ctc gtg ggt ggt tcg acc cgg atg ccc gcg gtg
ser val ser glu ile asp his val val leu val gly gly ser thr arg met pro ala val 1261/421                                       1291/431
acc gat ctg gtc aag gaa ctc acc ggc ggc aag gag ccc aac aag ggc gtc aac ccc gat
thr asp leu val lys glu leu thr gly gly lys glu pro asn lys gly val asn pro asp 1321/441                           1351/451
gag gtt gtc gcg gtg gga gcc gct ctg cag gcc ggc gtc ctc aag ggc gag gtg aaa gac
glu val val ala val gly ala ala leu gln ala gly val leu lys gly glu val lys asp 1381/461                           1411/471
gtt ctg ctg ctt gat gtt acc ccg ctg agc ctg ggt atc gag acc aag ggc ggg gtg atg
val leu leu leu asp val thr pro leu ser leu gly ile glu thr lys gly gly val met 1441/481                           1471/491
acc agg ctc atc gag cgc aac acc acg atc ccc acc aag cgg tcg gag act ttc acc acc
thr arg leu ile glu arg asn thr thr ile pro thr lys arg ser glu thr phe thr thr 1501/501                                       1531/511
gcc gac gac aac caa ccg tcg gtg cag atc cag gtc tat cag ggg gag cgt gag atc gcc
ala asp asp asn gln pro ser val gln ile gln val tyr gln gly glu arg glu ile ala 1561/521                                       1591/531
gcg cac aac aag ttg ctc ggg tcc ttc gag ctg acc ggc atc ccg ccg gcg ccg cgg ggg
ala his asn lys leu leu gly ser phe glu leu thr gly ile pro pro ala pro arg gly 1621/541                                       1651/551
att ccg cag atc gag gtc act ttc gac atc gac gcc aac ggc att gtg cac gtc acc gcc
ile pro gln ile glu val thr phe asp ile asp ala asn gly ile val his val thr ala 1681/561                                       1711/571
aag gac aag ggc acc ggc aag gag aac acg atc cga atc cag gaa ggc tcg ggc ctg tcc
lys asp lys gly thr gly lys glu asn thr ile arg ile gln glu gly ser gly leu ser 1741/581                                       1771/591
aag gaa gac att gac cgc atg atc aag gac gcc gaa gcg cac gcc gag gag gat cgc aag
lysglu asp ile asp arg met ile lys asp ala glu ala his ala glu glu asp arg lys 1801/601                                       1831/611
cgt cgc gag gag gcc gat gtt cgt aat caa gcc gag aca ttg gtc tac cag acg gag aag
arg arg glu glu ala asp val arg asn gln ala glu thr leu val tyr gln thr glu lys 1861/621                           1891/631
ttc gtc aaa gaa cag cgt gag gcc gag ggt ggt tcg aag gta cct gaa gac acg ctg aac
phe val lys glu gln arg glu ala glu gly gly ser lys val pro glu asp thr leu asn
```

```
1921/641                        1951/651
aag gtt gat gcc gcg gtg gcg gaa gcg aag gcg gca ctt ggc gga tcg gat att tcg gcc
lys val asp ala ala val ala glu ala lys ala ala leu gly gly ser asp ile ser ala 1981/661                        2011/671
atc aag tcg gcg atg gag aag ctg ggc cag gag tcg cag gct ctg ggg caa gcg atc tac
ile lys ser ala met glu lys leu gly gln glu ser gln ala leu gly gln ala ile tyr 2041/681                        2071/691
gaa gca gct cag gct gcg tca cag gcc act ggc gct gcc cac ccc ggc tcg gct gat gaA
glu ala ala gln ala ala ser gln ala thr gly ala ala his pro gly ser ala asp glu 2101/701
AGC a
ser
```

A preferred nucleotide sequence for the entire DNA vaccine vector is shown below (SEQ ID NO:13

```
   1 GCTCCGCCCC CCTGACGAGC ATCACAAAAA TCGACGCTCA AGTCAGAGGT

51 GGCGAAACCC GACAGGACTA TAAAGATACC AGGCGTTTCC CCCTGGAAGC

101 TCCCTCGTGC GCTCTCCTGT TCCGACCCTG CCGCTTACCG GATACCTGTC

151 CGCCTTTCTC CCTTCGGGAA GCGTGGCGCT TTCTCATAGC TCACGCTGTA

201 GGTATCTCAG TTCGGTGTAG GTCGTTCGCT CCAAGCTGGG CTGTGTGCAC

251 GAACCCCCCG TTCAGCCCGA CCGCTGCGCC TTATCCGGTA ACTATCGTCT

301 TGAGTCCAAC CCGGTAAGAC ACGACTTATC GCCACTGGCA GCAGCCACTG

351 GTAACAGGAT TAGCAGAGCG AGGTATGTAG GCGGTGCTAC AGAGTTCTTG

401 AAGTGGTGGC CTAACTACGG CTACACTAGA AGAACAGTAT TTGGTATCTG

451 CGCTCTGCTG AAGCCAGTTA CCTTCGGAAA AAGAGTTGGT AGCTCTTGAT

501 CCGGCAAACA AACCACCGCT GGTAGCGGTG GTTTTTTTGT TTGCAAGCAG

551 CAGATTACGC GCAGAAAAAA AGGATCTCAA GAAGATCCTT TGATCTTTTC

601 TACGGGGTCT GACGCTCAGT GGAACGAAAA CTCACGTTAA GGGATTTTGG

651 TCATGAGATT ATCAAAAAGG ATCTTCACCT AGATCCTTTT AAATTAAAAA

701 TGAAGTTTTA AATCAATCTA AGTATATAT GAGTAAACTT GGTCTGACAG

751 TTACCAATGC TTAATCAGTG AGGCACGTAT CTCAGCGATC TGTCTATTTC

801 GTTCATCCAT AGTTGCCTGA CTCGGGGGGG GGGGGCGCTG AGGTCTGCCT

851 CGTGAAGAAG GTGTTGCTGA CTCATACCAG GGCAACGTTG TTGCCATTGC

901 TACAGGCATC GTGGTGTCAC GCTCGTCGTT TGGTATGGCT TCATTCAGCT

951 CCGGTTCCCA ACGATCAAGG CGAGTTACAT GATCCCCCAT GTTGTGCAAA

1001 AAAGCGGTTA GCTCCTTCGG TCCTCCGATC GTTGTCAGAA GTAAGTTGGC

1051 CGCAGTGTTA TCACTCATGG TTATGGCAGC ACTGCATAAT TCTCTTACTG

1101 TCATGCCATC CGTAAGATGC TTTTCTGTGA CTGGTGAGTA CTCAACCAAG

1151 TCATTCTGAG AATAGTGTAT GCGGCGACCG AGTTGCTCTT GCCCGGCGTC

1201 AATACGGGAT AATACCGCGC CACATAGCAG AACTTTAAAA GTGCTCATCA

1251 TTGGAAAACG TTCTTCGGGG CGAAAACTCT CAAGGATCTT ACCGCTGTTG

1301 AGATCCAGTT CGATGTAACC CACTCGTGCA CCTGAATCGC CCCATCATCC

1351 AGCCAGAAAG TGAGGGAGCC ACGGTTGATG AGAGCTTTGT TGTAGGTGGA

1401 CCAGTTGGTG ATTTTGAACT TTTGCTTTGC CACGGAACGG TCTGCGTTGT

1451 CGGGAAGATG CGTGATCTGA TCCTTCAACT CAGCAAAAGT TCGATTTATT
```

```
1501  CAACAAAGCC GCCGTCCCGT CAAGTCAGCG TAATGCTCTG CCAGTGTTAC
1551  AACCAATTAA CCAATTCTGA TTAGAAAAAC TCATCGAGCA TCAAATGAAA
1601  CTGCAATTTA TTCATATCAG GATTATCAAT ACCATATTTT TGAAAAAGCC
1651  GTTTCTGTAA TGAAGGAGAA AACTCACCGA GGCAGTTCCA TAGGATGGCA
1701  AGATCCTGGT ATCGGTCTGC GATTCCGACT CGTCCAACAT CAATACAACC
1751  TATTAATTTC CCCTCGTCAA AAATAAGGTT ATCAAGTGAG AAATCACCAT
1801  GAGTGACGAC TGAATCCGGT GAGAATGGCA AAAGCTTATG CATTTCTTTC
1851  CAGACTTGTT CAACAGGCCA GCCATTACGC TCGTCATCAA AATCACTCGC
1901  ATCAACCAAA CCGTTATTGA TTCGTGATTG CGCCTGAGCG AGACGAAATA
1951  CGCGATCGCT GTTAAAAGGA CAATTACAAA CAGGAATGGA ATGCAACCGG
2001  CGCAGGAACA CTGCCAGCGC ATCAACAATA TTTTCACCTG AATCAGGATA
2051  TTCTTCTAAT ACCTGGAATG CTGTTTTCCC GGGGATCGCA GTGGTGAGTA
2101  ACCATGCATC ATCAGGAGTA CGGATAAAAT GCTTGATGGT CGGAAGAGGC
2151  ATAAATTCCG TCAGCCAGTT TAGTCTGACC ATCTCATCTG TAACATCATT
2201  GGCAACGCTA CCTTTGCCAT GTTTCAGAAA CAACTCTGGC GCATCGGGCT
2251  TCCCATACAA TCGATAGATT GTCGCACCTG ATTGCCCGAC ATTATCGCGA
2301  GCCCATTTAT ACCCATATAA ATCAGCATCC ATGTTGGAAT TAATCGGGG
2351  CCTCGAGCAA GACGTTTCCC GTTGAATATG GCTCATAACA CCCCTTGTAT
2401  TACTGTTTAT GTAAGCAGAC AGTTTTATTG TTCATGATGA TATATTTTA
2451  TCTTGTGCAA TGTAACATCA GAGATTTTGA GACACAACGT GGCTTTCCCC
2501  CCCCCCCCAT TATTGAAGCA TTTATCAGGG TTATTGTCTC ATGAGCGGAT
2551  ACATATTTGA ATGTATTTAG AAAAATAAAC AAATAGGGGT TCCGGGCACA
2601  TTTCCCCGAA AAGTGCCACC TGACGTCTAA GAAACCATTA TTATCATGAC
2651  ATTAACCTAT AAAAATAGGC GTATCACGAG GCCCTTTCGT CTCGCGCGTT
2701  TCGGTGATGA CGGTGAAAAC CTCTGACACA TGCAGCTCCC GGAGACGGTC
2751  ACAGCTTGTC TGTAAGCGGA TGCCGGGAGC AGACAAGCCC GTCAGGGCGC
2801  GTCAGCGGGT GTTGGCGGGT GTCGGGGCTG GCTTAACTAT GCGGCATCAG
2851  AGCAGATTGT ACTGAGAGTG CACCATATGC GGTGTGAAAT ACCGCACAGA
2901  TGCGTAAGGA GAAAATACCG CATCAGATTG GCTATTGGCC ATTGCATACG
2951  TTGTATCCAT ATCATAATAT GTACATTTAT ATTGGCTCAT GTCCAACATT
3001  ACCGCCATGT TGACATTGAT TATTGACTAG TTATTAATAG TAATCAATTA
3051  CGGGGTCATT AGTTCATAGC CCATATATGG AGTTCCGCGT TACATAACTT
3101  ACGGTAAATG GCCCGCCTGG CTGACCGCCC AACGACCCCC GCCCATTGAC
3151  GTCAATAATG ACGTATGTTC CCATAGTAAC GCCAATAGGG ACTTTCCATT
3201  GACGTCAATG GGTGGAGTAT TTACGGTAAA CTGCCCACTT GGCAGTACAT
3251  CAAGTGTATC ATATGCCAAG TACGCCCCCT ATTGACGTCA ATGACGGTAA
3301  ATGGCCCGCC TGGCATTATG CCCAGTACAT GACCTTATGG GACTTTCCTA
3351  CTTGGCAGTA CATCTACGTA TTAGTCATCG CTATTACCAT GGTGATGCGG
3401  TTTTGGCAGT ACATCAATGG GCGTGGATAG CGGTTTGACT CACGGGGATT
```

```
3451 TCCAAGTCTC CACCCCATTG ACGTCAATGG GAGTTTGTTT TGGCACCAAA
3501 ATCAACGGGA CTTTCCAAAA TGTCGTAACA ACTCCGCCCC ATTGACGGAA
3551 ATGGGCGGTA GGCGTGTACG GTGGGAGGTC TATATAAGCA GAGCTCGTTT
3601 AGTGAACCGT CAGATCGCCT GGAGACGCCA TCCACGCTGT TTTGACCTCC
3651 ATAGAAGACA CCGGGACCGA TCCAGCCTCC GCGGCCGGGA ACGGTGCATT
3701 GGAACGCGGA TTCCCCGTGC AAGAGTGAC GTAAGTTCCG CCTATAGACT
3751 CTATAGGCAC ACCCCTTTGG CTCTTATGCA TGCTATACTG TTTTTGGCTT
3801 GGGGCCTATA CACCCCCGCT TCCTTATGCT ATAGGTGATG GTATAGCTTA
3851 GCCTATAGGT GTGGGTTATT GACCATTATT GACCACTCCA ACGGTGGAGG
3901 GCAGTGTAGT CTGAGCAGTA CTCGTTGCTG CCGCGCGCGC CACCAGACAT
3951 AATAGCTGAC AGACTAACAG ACTGTTCCTT TCCATGGGTC TTTTCTGCAG
4001 TCACCGTCGT CGACGGTATC GATAAGCTTG ATATGGAATT CCTCGACGGA
4051 TCTTATGGCG GCCCCCGGCG CCCGGCGGCC GCTGCTCCTG CTGCTGCTGG
4101 CAGGCCTTGC ACATGGCGCC TCAGCACTCT TTGAGGATCT AATCATGCAT
4151 GGAGATACAC CTACATTGCA TGAATATATG TTAGATTTGC AACCAGAGAC
4201 AACTGATCTC TACGGTTATG GGCAATTAAA TGACAGCTCA GAGGAGGAGG
4251 ATGAAATAGA TGGTCCAGCT GGACAAGCAG AACCGGACAG AGCCCATTAC
4301 AATATTGTAA CCTTTTGTTG CAAGTGTGAC TCTACGCTTC GGTTGTGCGT
4351 ACAAAGCACA CACGTAGACA TTCGTACTTT GGAAGACCTG TTAATGGGCA
4401 CACTAGGAAT TGTGTGCCCC ATCTGTTCTC AAGGATCCAT GGCTCGTGCG
4451 GTCGGGATCG ACCTCGGGAC CACCAACTCC GTCGTCTCGG TTCTGGAAGG
4501 TGGCGACCCG GTCGTCGTCG CCAACTCCGA GGGCTCCAGG ACCACCCCGT
4551 CAATTGTCGC GTTCGCCCGC AACGGTGAGG TGCTGGTCGG CCAGCCCGCC
4601 AAGAACCAGG CGGTGACCAA CGTCGATCGC ACCGTGCGCT CGGTCAAGCG
4651 ACACATGGGC AGCGACTGGT CCATAGAGAT TGACGGCAAG AAATACACCG
4701 CGCCGGAGAT CAGCGCCCGC ATTCTGATGA AGCTGAAGCG CGACGCCGAG
4751 GCCTACCTCG GTGAGGACAT TACCGACGCG GTTATCACGA CGCCCGCCTA
4801 CTTCAATGAC GCCCAGCGTC AGGCCACCAA GGACGCCGGC CAGATCGCCG
4851 GCCTCAACGT GCTGCGGATC GTCAACGAGC CGACCGCGGC CGCGCTGGCC
4901 TACGGCCTCG ACAAGGGCGA GAAGGAGCAG CGAATCCTGG TCTTCGACTT
4951 GGGTGGTGGC ACTTTCGACG TTTCCCTGCT GGAGATCGGC GAGGGTGTGG
5001 TTGAGGTCCG TGCCACTTCG GGTGACAACC ACCTCGGCGG CGACGACTGG
5051 CATCGATCTG ACCAAGGACA AGATGGCGAT GCAGCGGCTG CGGGAAGCCG
5151 CCGAGAAGGC AAAGATCGAG CTGAGTTCGA GTCAGTCCAC CTCGATCAAC
5201 CTGCCCTACA TCACCGTCGA CGCCGACAAG AACCCGTTGT TCTTAGACGA
5251 GCAGCTGACC CGCGCGGAGT TCAACGGAT CACTCAGGAC CTGCTGGACC
5301 GCACTCGCAA GCCGTTCCAG TCGGTGATGG CTGACACCGG CATTTCGGTG
5351 TCGGAGATCG ATCACGTTGT GCTCGTGGGT GGTTCGACCC GGATGCCCGC
```

```
5401 GGTGACCGAT CTGGTCAAGG AACTCACCGG CGGCAAGGAA CCCAACAAGG

5451 GCGTCAACCC CGATGAGGTT GTCGCGGTGG GAGCCGCTCT GCAGGCCGGC

5501 GTCCTCAAGG GCGAGGTGAA AGACGTTCTG CTGCTTGATG TTACCCCGCT

5551 GAGCCTGGGT ATCGAGACCA AGGGCGGGGT GATGACCAGG CTCATCGAGC

5601 GCAACACCAC GATCCCCACC AAGCGGTCGG AGACTTTCAC CACCGCCGAC

5651 GACAACCAAC CGTCGGTGCA GATCCAGGTC TATCAGGGGG AGCGTGAGAT

5701 CGCCGCGCAC AACAAGTTGC TCGGGTCCTT CGAGCTGACC GGCATCCCGC

5751 CGGCGCCGCG GGGGATTCCG CAGATCGAGG TCACTTTCGA CATCGACGCC

5801 AACGGCATTG TGCACGTCAC CGCCAAGGAC AAGGGCACCG GCAAGGAGAA

5851 CACGATCCGA ATCCAGGAAG CTCGGGCCT GTCCAAGGAA GACATTGACC

5901 GCATGATCAA GGACGCCGAA GCGCACGCCG AGGAGGATCG CAAGCGTCGC

5951 GAGGAGGCCG ATGTTCGTAA TCAAGCCGAG ACATTGGTCT ACCAGACGGA

6001 GAAGTTCGTC AAAGAACAGC GTGAGGCCGA GGGTGGTTCG AAGGTACCTG

6051 AAGACACGCT GAACAAGGTT GATGCCGCGG TGGCGGAAGC GAAGGCGGCA

6101 CTTGGCGGAT CGGATATTTC GGCCATCAAG TCGGCGATGG AGAAGCTGGG

6151 CCAGGAGTCG CAGGCTCTGG GGCAAGCGAT CTACGAAGCA GCTCAGGCTG

6201 CGTCACAGGC CACTGGCGCT GCCCACCCCG GCTCGGCTGA TGAAAGCTTA

6251 AGTTTAAACC GCTAGCCTAG AGCGGCCGCG GATCCAGATC TTTTTCCCTC

6301 TGCCAAAAAT TATGGGGACA TCATGAAGCC CCTTGAGCAT CTGACTTCTG

6351 GCTAATAAAG GAAATTTATT TTCATTGCAA TAGTGTGTTG GAATTTTTTG

6401 TGTCTCTCAC TCGGAAGGAC ATATGGGAGG GCAAATCATT TAAAACATCA

6451 GAATGAGTAT TTGGTTTAGA GTTTGGCAAC ATATGCCCAT TCTTCCGCTT

6501 CCTCGCTCAC TGACTCGCTG CGCTCGGTCG TTCGGCTGCG GCGAGCGGTA

6551 TCAGCTCACT CAAAGGCGGT AATACGGTTA TCCACAGAAT CAGGGGATAA

6601 CGCAGGAAAG AACATGTGAG CAAAAGGCCA GCAAAAGGCC AGGAACCGTA

6651 AAAAGGCCGC GTTGCTGGCG TTTTTCCATA G
```

The plasmid pNGVL4a-SigE7(detox) HSP70-3 is schematically illustrated in FIG. 5a. A summary of this plasmid's components is shown below in Table I, as well as their position and origin.

TABLE I

| Plasmid Position | Genetic Construct | Source of Construct |
|---|---|---|
| 6491-0823 | E. coli ORI (ColEI) | pBR/E. coli-derived |
| 0837-0881 | portion of transposase (tpnA) | Common plasmid seq, Tn5/Tn903 |
| 0882-1332 | β-Lactamase (AmpR) | pBRpUC derived plasmid |
| 1331-2496 | AphA (KanR) | Tn903 |
| 2509-2691 | P3 Promoter DNA binding site | Tn3/pBR322 |
| 2692-2926 | pUC backbone | Common plasmid seq. pBR322-derived |
| 2931-4009 | NF1 binding and promoter | HHV-5(HCMV UL-10 IE1 gene) |
| 4010-4044 | Poly-cloning site | Common plasmid seq, pBlueScript (?) |
| 4055-4144 | Signal Peptide (Sig) | Mammalian lysosomal membrane glycoprotein A |

TABLE I-continued

| Plasmid Position | Genetic Construct | Source of Construct |
|---|---|---|
| 4145-4432 | dE7 gene (detoxified partial) | HPV-16 (E7 gene) |
| 4437-6243 | DNA K gene | M. tuberculosis HSP70 |
| 6243-6289 | Poly-cloning site | Common plasmid sequence |
| 6289-6493 | Poly-Adenylation site | Mammalian signal, pHCMV-derived |

A portion of SEQ ID NO: 13 annotated with the Sig, E7 (detox) and HSP-70 regions is shown below (nucleotides 3951-6350 of SEQ ID NO: 13). The vector sequence is in lower case; the signal peptide (Sig) is bold italic and annotated over the lines. The E7 (detox) sequence is upper case underscored (and annotated over the lines). The HSP70 sequence is italicized and underscored (not bolded) and is also annotated over the lines.

```
     . . .
3951 aatagctgac agactaacag actgttcctt tccatgggtc ttttctgcag 4001 tcaccgtcgt cgacggtatc gataagcttg atatcgaatt cctcgacgga <-----------------Signal Peptide--------------------
4051 tcttATGGCG GCCCCCGGCG CCCGGCGGCC GCTGCTCCTC CTGCTGCTGG --------------------------------------->< -----
4101 CAGGCCTTGC ACATGGCGCC TCAGCACTCT TGAGGATCT AATCATGCAT ------------E7(detox)-------------------------------
4151 GGAGATACAC CTACATTGCA TGAATATATG TTAGATTTGC AACCAGAGAC

4201 AACTGATCTC TACGGTTATG GCAATTAAA TGACAGCTCA GAGGAGGAGG

4251 ATGAAATAGA TGGTCCAGCT GGACAAGCAG AACCGGACAG AGCCCATTAC

4301 AATATTGTAA CCTTTTGTTG CAAGTGTGAC TCTACGCTTC GGTTGTGCGT

4351 ACAAAGCACA CACGTAGACA TTCGTACTTT GGAAGACCTG TTAATGGGCA
     --------------------------------->    <-------------
4401 ACACTAGGAAT TGTGTGCCCC ATCTGTTCTC AAggatccAT GGCTCGTGCG -----------HSP70
         (E. coli DNA K)--------------------- . . .
4451 GTCGGGATCG ACCTCGGGAC CACCAACTCC GTCGTCTCGG TTCTGGAAGG

4501 TGGCGACCCG CTCGTCGTCG CCAACTCCGA GGGCTCCAGG ACCACCCCGT

4551 CAATTGTCGC GTTCGCCCGC AACGGTCAGG TGCTCGTCGG CCAGCCCGCC

4601 AAGAACCAGG CGGTGACCAA CGTCGATCGC ACCGTGCGCT CGGTCAAGCG

4651 ACACATGGGC AGCGACTGGT CCATAGAGAT TGACGGCAAG AAATACACCG

4701 CGCCGGAGAT CAGCGCCCGC ATTCTGATGA AGCTGAAGCG CGACGCCGAG

4751 GCCTACCTCG GTGACGACAT TACCGACGCG GTTATCACGA CGCCCGCCTA

4801 CTTCAATGXC GCCCAGCGTC AGGCCACCAA GGACGCCGGC CAGATCGCCG

4851 GCCTCAACGT GCTGCGGATC GTCAACGAGC CGACCGCGGC CGCGCTGGCC

4901 TACGGCCTCG ACAAGCGCGA GAAGGAGCAG CCAATCCTGG TCTTCGACTT

4951 GGGTGCTGGC ACTTTCGACG TTTCCCTGCT GGAGATCGGC GAGGGTGTGG

5001 TTCAGGTCCG TGCCACTTCG GGTGACAACC ACCTCGGCGG CGACGACTGG

5051 CACCAGCGGG TCGTCGATTG GCTGGTGGAC AAGTTCAAGG GCACCAGCGG

5101 CATCGATCTG ACCAAGGACA AGATGGCGAT GCAGCGGCTG CGGGAAGCCG

5151 CCGAGAAGGC AAAGATCGAG CTGAGTTCGA GTCAGTCCAC CTCGATCAAC

5201 CTGCCC7ACA TCACCGTCGA CGCCGACAAG AACCCGTTGT TCTTAGACGA

5251 GCAGCTGACC CGCGCGGAGT TCCAACGGAT CACTCAGGAG CTGCTGGACC

5301 GCACTCGCAA GCCGTTCCAG TCGGTGATCG CTGACACCGG CATTTCGGTG

5351 TCGGAGATCG ATCACGTTGT GCTCGTGGGT GG7TCGACCC GGATGCCCGC

5401 GGTGACCGAT CTGGTCAAGG AACTCACCCG CGGCAAGCAA CCCAACAAGG

5451 GCGTCAACCC CGATGACGTT GTCGCGGTGG AGCCGCTCT GCAGGCCGGC

5501 GTCCTCAAGG GCGAGGTGAA AGACGTTCTG CTGCTTGATG TTACCCCGCT

5551 GAGCCTGGGT ATCGAGACCA AGGGCGGGGT GATGACCAGG CTCATCGAGC

5601 GCAACACCAC GATCCCCACC AAGCGGTCGG AGACTTTCAC CACCGCCGAC

5651 GACAACCAAC CGTCGGTGCA GATCCAGGTC TATCAGGGGG AGCGTGAGAT
```

```
5701 CGCCGCGCAC AACAAGTTGC TCGGGTCCTT CGAGCTGACC GGCATCCCGC

5751 CGGCGCCGCG GGGGATTCCG CAGATCGAGG TCACTTTCGA CATCGACGCC

5801 AACGGCATTG TGCACGTCAC CGCCAAGGAC AAGGGCACCG GCAAGGAGAA

5851 CACGATCCGA ATCCAGGAAG CCTCGGGCCT GTCCAAGGAA GACATTGACC

5901 GCATGATCAA GGACGCCGAA GCGCACGCCG AGGACGATCG CAAGCGTCGC

5951 GAGGAGGCCG ATGTTCGTAA TCAAGCCGAG ACATTGGTCT ACCAGACGGA

6001 GAAGTTCGTC AAAGAACAGC GTGAGGCCGA GGGTGGTTCG AAGGTACCTG

6051 AAGACACGCT GAACAAGGTT GATGCCGCGG TGGCGGAAGC GAAGGCGGCA

6101 CTTGGCGGAT CGGATATTTC GCCCATCAAG TCGGCGATGG AGAAGCTGGG

6151 CCAGGAGTCG CAGGCTCTGG GGCAAGCGAT CTACGAAGCA GCTCAGGCTG
          -------------------------------------------->

6201 CGTCACAGGC CACTGGCGCT GCCCACCCCG GCTCGGCTGA TGAaagctta 6251 agtttaaacc gctagcctag agcggccgcg gatccagatc tttttccctc 6301 tgccaaaaat tatggggaca tcatgaaccc ccttgagcat ctgacttctg
 . . .
```

General Recombinant DNA Methods

Basic texts disclosing general methods of molecular biology, all of which are incorporated by reference, include: Sambrook, J et al., *Molecular Cloning: A Laboratory Manual*, 2$^{nd}$ Edition, Cold Spring Harbor Press, Cold Spring Harbor, N.Y., 1989; Ausubel, F M et al. *Current Protocols in Molecular Biology*, Vol. 2, Wiley-Interscience, New York, (current edition); Kriegler, *Gene Transfer and Expression: A Laboratory Manual* (1990); Glover, D M, ed, *DNA Cloning: A Practical Approach*, vol. I & II, IRL Press, 1985; Albers, B. et al., *Molecular Biology of the Cell*, 2$^{nd}$ Ed., Garland Publishing, Inc., New York, N.Y. (1989); Watson, J D et al., *Recombinant DNA*, 2$^{nd}$ Ed., Scientific American Books, New York, 1992; and Old, R W et al., *Principles of Gene Manipulation: An Introduction to Genetic Engineering*, 2$^{nd}$ Ed., University of California Press, Berkeley, Calif. (1981).

Techniques for the manipulation of nucleic acids, such as, e.g., generating mutations in sequences, subcloning, labeling probes, sequencing, hybridization and the like are well described in the scientific and patent literature. See, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Tijssen, ed. Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyper diffusion chromatography, various immunological methods, e.g. fluid or gel precipitin reactions, immunodiffusion, immuno-electrophoresis, radioimmunoassays (Rios), enzyme-linked immunosorbent assays (ELISAs), immuno-fluorescence assays, Southern analysis, Northern analysis, dot-blot analysis, gel electrophoresis (e.g., SDS-PAGE), RTF-PCR, quantitative PCR, other nucleic acid or target or signal amplification methods, radiolabeling, scintillation counting, and affinity chromatography.

Amplification of Nucleic Acids

Oligonucleotide primers can be used to amplify nucleic acids to generate fusion protein coding sequences used to practice the invention, to monitor levels of vaccine after in vivo administration (e.g., levels of a plasmid or virus), to confirm the presence and phenotype of activated CTLs, and the like. The skilled artisan can select and design suitable oligonucleotide amplification primers using known sequences. Amplification methods are also well known in the art, and include, e.g., polymerase chain reaction, PCR (*PCR Protocols, A Guide to Methods and Applications*, Academic Press, N.Y. (1990) and *PCR Strategies* (1995), Academic Press, Inc., N.Y., ligase chain reaction (LCR) (Wu (1989) Genomics 4:560; Landegren (1988) Science 241: 1077; Barringer (1990) Gene 89:117); transcription amplification. (Kwoh (1989) Proc. Natl. Acad. Sci. USA 86:1173); and, self-sustained sequence replication (Guatelli (1990) Proc. Natl. Acad. Sci. USA 87:1874); Qβ replicase amplification (Smith (1997) J. Clin. Microbiol. 35:1477-1491; Burg (1996) Mol. Cell. Probes 10:257-271) and other RNA polymerase mediated techniques (NASBA, Cangene, Mississauga, Ontario; Berger (1987) Methods Enzymol. 152: 307-316; U.S. Pat. Nos. 4,683,195 and 4,683,202; Sooknanan (1995) Biotechnology 13:563-564).

Unless otherwise indicated, a particular nucleic acid sequence is intended to encompasses conservative substitution variants thereof (e.g., degenerate codon substitutions) and a complementary sequence. The term "nucleic acid" is synonymous with "polynucleotide" and is intended to include a gene, a cDNA molecule, an mRNA molecule, as well as a fragment of any of these such as an oligonucleotide, and further, equivalents thereof (explained more fully below). Sizes of nucleic acids are stated either as kilobases (kb) or base pairs (bp). These are estimates derived from agarose or polyacrylamide gel electrophoresis (PAGE), from nucleic acid sequences which are determined by the user or published. Protein size is stated as molecular mass in kilodaltons (kDa) or as length (number of amino acid residues). Protein size is estimated from PAGE, from sequencing, from presumptive amino acid sequences based on the coding nucleic acid sequence or from published amino acid sequences.

Specifically, cDNA molecules encoding the amino acid sequence corresponding to the fusion polypeptide of the present invention or fragments or derivatives thereof can be synthesized by the polymerase chain reaction (PCR) (see, for example, U.S. Pat. No. 4,683,202) using primers derived the sequence of the protein disclosed herein. These cDNA sequences can then be assembled into a eukaryotic or prokaryotic expression vector and the resulting vector can be used to direct the synthesis of the fusion polypeptide or its fragment or derivative by appropriate host cells, for example COS or CHO cells.

This invention includes isolated nucleic acids having a nucleotide sequence encoding the novel fusion polypeptides that comprise a translocation polypeptide and an antigen, fragments thereof or equivalents thereof. The term nucleic acid as used herein is intended to include such fragments or equivalents. The nucleic acid sequences of this invention can be DNA or RNA.

A cDNA nucleotide sequence the fusion polypeptide can be obtained by isolating total mRNA from an appropriate cell line. Double stranded cDNA is prepared from total mRNA. cDNA can be inserted into a suitable plasmid, bacteriophage or viral vector using any one of a number of known techniques.

In reference to a nucleotide sequence, the term "equivalent" is intended to include sequences encoding structurally homologous and/or a functionally equivalent proteins. For example, a natural polymorphism in a nucleotide sequence encoding an anti-apoptotic polypeptide according to the present invention (especially at the third base of a codon) may be manifest as "silent" mutations which do not change the amino acid sequence. Furthermore, there may be one or more naturally occurring isoforms or related, immunologically cross-reactive family members of these proteins. Such isoforms or family members are defined as proteins that share function amino acid sequence similarity to the reference polypeptide.

Fragment of Nucleic Acid

A fragment of the nucleic acid sequence is defined as a nucleotide sequence having fewer nucleotides than the nucleotide sequence encoding the full length translocation polypeptide, antigenic polypeptide or the fusion thereof. This invention includes such nucleic acid fragments that encode polypeptides which retain (1) the ability of the fusion polypeptide to induce increases in frequency or reactivity of T cells, preferably CD8+ T cells, that are specific for the antigen part of the fusion polypeptide.

For example, a nucleic acid fragment as intended herein encodes an anti-apoptotic polypeptide that retains the ability to improve the immunogenicity of an antigenic composition when administered as a chimeric DNA with antigen-encoding sequence, or when co-administered therewith.

Generally, the nucleic acid sequence encoding a fragment of an anti-apoptotic polypeptide comprises of nucleotides from the sequence encoding the mature protein (or an active fragment thereof).

Nucleic acid sequences of this invention may also include linker sequences, natural or modified restriction endonuclease sites and other sequences that are useful for manipulations related to cloning, expression or purification of encoded protein or fragments. These and other modifications of nucleic acid sequences are described herein or are well-known in the art.

The techniques for assembling and expressing DNA coding sequences for translocation types of proteins, and DNA coding sequences for antigenic polypeptides, include synthesis of oligonucleotides, PCR, transforming cells, constructing vectors, expression systems, and the like; these are well-established in the art such that those of ordinary skill are familiar with standard resource materials, specific conditions and procedures.

Expression Vectors and Host Cells

This invention includes an expression vector comprising a nucleic acid sequence encoding a anti-apoptotic polypeptide or a targeting polypeptide operably linked to at least one regulatory sequence. These vectors are also in the process of producing the final vaccine vector.

The term "expression vector" as used herein refers to a nucleotide sequence which is capable of affecting expression of a protein coding sequence in a host compatible with such sequences. Expression cassettes include at least a promoter operably linked with the polypeptide coding sequence; and, optionally, with other sequences, e.g., transcription termination signals. Additional factors necessary or helpful in effecting expression may also be included, e.g., enhancers.

"Operably linked" means that the coding sequence is linked to a regulatory sequence in a manner that allows expression of the coding sequence. Known regulatory sequences are selected to direct expression of the desired protein in an appropriate host cell. Accordingly, the term "regulatory sequence" includes promoters, enhancers and other expression control elements. Such regulatory sequences are described in, for example, Goeddel, *Gene Expression Technology. Methods in Enzymology*, vol. 185, Academic Press, San Diego, Calif. (1990)).

Thus, expression cassettes include plasmids, recombinant viruses, any form of a recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Where a vector is being maintained by a host cell, the vector may either be stably replicated by the cells during mitosis as an autonomous structure, or is incorporated within the host's genome.

Those skilled in the art appreciate that the particular design of an expression vector of this invention depends on considerations such as the host cell to be transfected and/or the type of protein to be expressed.

The present expression vectors comprise the full range of nucleic acid molecules encoding the various embodiments of the fusion polypeptide and its functional derivatives (defined herein) including polypeptide fragments, variants, etc.

Such expression vectors are used to transfect host cells (in vitro, ex vivo or in vivo) for expression of the DNA and production of the encoded proteins which include fusion proteins or peptides. It will be understood that a genetically modified cell expressing the fusion polypeptide may transiently express the exogenous DNA for a time sufficient for the cell to be useful for its stated purpose. Host cells may also be transfected with one or more expression vectors that singly or in combination comprise DNA encoding at least a portion of the fusion polypeptide and DNA encoding at least a portion of a second protein, so that the host cells produce yet further fusion polypeptides that include both the portions. A culture typically includes host cells, appropriate growth media and other byproducts. Suitable culture media are well known in the art. The fusion polypeptide can be isolated from medium or cell lysates using conventional techniques for purifying proteins and peptides, including ammonium sulfate precipitation, fractionation column chromatography (e.g. ion exchange, gel filtration, affinity chromatography, etc.) and/or electrophoresis (see generally, "Enzyme Purification and Related Techniques", *Methods in Enzymology*, 22:233-577 (1971)). Once purified, partially or to homogeneity, the recombinant polypeptides of the invention can be utilized in pharmaceutical compositions as described in more detail herein.

The term "isolated" as used herein, when referring to a molecule or composition, such as a nucleic acid, means that the molecule or composition is separated from at least one other compound (protein, other nucleic acid, etc.) or from other contaminants with which it is natively associated or becomes associated during processing. An isolated composition can also be substantially pure. An isolated composition can be in a homogeneous state and can be dry or in aqueous solution. Purity and homogeneity can be determined, for example, using analytical chemical techniques.

Prokaryotic or eukaryotic host cells transformed or transfected to express the fusion polypeptide or a homologue or functional derivative thereof are within the scope of the invention. For example, the fusion polypeptide may be expressed in bacterial cells such as *E. coli*, insect cells (baculovirus), yeast, or mammalian cells such as Chinese hamster ovary cells (CHO) or human cells. Other suitable host cells may be found in Goeddel, (1990) supra or are otherwise known to those skilled in the art.

Expression in eukaryotic cells leads to partial or complete glycosylation and/or formation of relevant inter- or intrachain disulfide bonds of the recombinant protein.

Often, in fusion expression vectors, a proteolytic cleavage site is introduced at the junction of the reporter group and the target protein to enable separation of the target protein from the reporter group subsequent to purification of the fusion protein. Proteolytic enzymes for such cleavage and their recognition sequences include Factor Xa, thrombin and enterokinase.

Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase, maltose E binding protein, or protein A, respectively, to the target recombinant protein.

Inducible non-fusion expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). While target gene expression relies on host RNA polymerase transcription from the hybrid trp-lac fusion promoter in pTrc, expression of target genes inserted into pET 11d relies on transcription from the T7 gn10-lacO fusion promoter mediated by coexpressed viral RNA polymerase (T7gn1). Th is viral polymerase is supplied by host strains BL21(DE3) or HMS174(DE3) from a resident λ prophage harboring a T7gn1 under the transcriptional control of the lacUV 5 promoter.

Vector Construction

Construction of suitable vectors comprising the desired coding and control sequences employs standard ligation and restriction techniques which are well understood in the art. Isolated plasmids, DNA sequences, or synthesized oligonucleotides are cleaved, tailored, and re-ligated in the form desired.

The DNA sequences which form the vectors are available from a number of sources. Backbone vectors and control systems are generally found on available "host" vectors which are used for the bulk of the sequences in construction. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleotide derivatives. The entire gene sequence for genes of sizeable length, e.g., 500-1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, M. D., *Nature* (1981) 292:756; Nambair, K. P., et al., *Science* (1984) 223:1299; and Jay, E., *J Biol Chem* (1984) 259:6311.

Vector DNA can be introduced into mammalian cells via conventional techniques such as calcium phosphate or calcium chloride co-precipitation, DEAE-dextran-mediated transfection, lipofection, or electroporation. Suitable methods for transforming host cells can be found in Sambrook et al. supra and other standard texts.

Often, in fusion expression vectors, a proteolytic cleavage site is introduced at the junction of the reporter group and the target protein to enable separation of the target protein from the reporter group subsequent to purification of the fusion protein. Proteolytic enzymes for such cleavage and their recognition sequences include Factor Xa, thrombin and enterokinase.

Promoters and Enhancers

The preferred promoter sequences of the present invention must be operable in mammalian cells and may be either eukaryotic or viral promoters. Although preferred promoters are described in the Examples, other useful promoters and regulatory elements are discussed below. Suitable promoters may be inducible, repressible or constitutive. A "constitutive" promoter is one which is active under most conditions encountered in the cell's environmental and throughout development. An "inducible" promoter is one which is under environmental or developmental regulation. A "tissue specific" promoter is active in certain tissue types of an organism. An example of a constitutive promoter is the viral promoter MSV-LTR, which is efficient and active in a variety of cell types, and, in contrast to most other promoters, has the same enhancing activity in arrested and growing cells. Other preferred viral promoters include that present in the CMV-LTR (from cytomegalovirus) (Bashart, M. et al., *Cell* 41:521 (1985)) or in the RSV-LTR (from Rous sarcoma virus) (Gorman, C. M., *Proc. Natl. Acad. Sci. USA* 79:6777 (1982). Also useful are the promoter of the mouse metallothionein I gene (Hamer, D., et al., *J. Mol. Appl. Gen.* 1:273-288 (1982)); the TK promoter of Herpes virus (McKnight, S., *Cell* 31:355-365 (1982)); the SV40 early promoter (Benoist, C., et al., *Nature* 290:304-310 (1981)); and the yeast gal4 gene promoter (Johnston, S. A., et al., *Proc. Natl. Acad. Sci.* (*USA*) 79:6971-6975 (1982); Silver, P. A., et al., *Proc. Natl. Acad. Sci.* (*USA*) 81:5951-5955 (1984)). Other illustrative descriptions of transcriptional factor association with promoter regions and the separate activation and DNA binding of transcription factors include: Keegan et al., *Nature* (1986) 231:699; Fields et al., *Nature* (1989) 340:245; Jones, *Cell* (1990) 61:9; Lewin, Cell (1990) 61:1161; Ptashne et al., *Nature* (1990) 346:329; Adams et al., *Cell*

(1993) 72:306. The relevant disclosure of all of these above-listed references is hereby incorporated by reference.

The promoter region may further include an octamer region which may also function as a tissue specific enhancer, by interacting with certain proteins found in the specific tissue. The enhancer domain of the DNA construct of the present invention is one which is specific for the target cells to be transfected, or is highly activated by cellular factors of such target cells. Examples of vectors (plasmid or retrovirus) are disclosed in (Roy-Burman et al., U.S. Pat. No. 5,112,767). For a general discussion of enhancers and their actions in transcription, see, Lewin, B. M., Genes IV, Oxford University Press, Oxford, (1990), pp. 552-576. Particularly useful are retroviral enhancers (e.g., viral LTR). The enhancer is preferably placed upstream from the promoter with which it interacts to stimulate gene expression. For use with retroviral vectors, the endogenous viral LTR may be rendered enhancer-less and substituted with other desired enhancer sequences which confer tissue specificity or other desirable properties such as transcriptional efficiency.

Nucleic acids of the invention can also be chemically synthesized using standard techniques. Various methods of chemically synthesizing polydeoxynucleotides are known, including solid-phase synthesis which, like peptide synthesis, has been fully automated with commercially available DNA synthesizers (See, e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

Proteins and Polypeptides

The terms "polypeptide," "protein," and "peptide" when referring to compositions of the invention are meant to include variants, analogues, and mimetics with structures and/or activity that substantially correspond to the polypeptide or peptide from which the variant, etc., was derived.

The present invention includes the expression in vivo of fusion polypeptides comprising a targeting polypeptide linked to an antigenic polypeptide.

The term "chimeric" or "fusion" polypeptide or protein refers to a composition comprising at least one polypeptide or peptide sequence or domain that is chemically bound in a linear fashion with a second polypeptide or peptide domain. One embodiment of this invention is an isolated or recombinant nucleic acid molecule encoding a fusion protein comprising at least two domains, wherein the first domain comprises an anti-apoptotic polypeptide and the second domain comprising an antigenic epitope, e.g., an MHC class I-binding peptide epitope. Additional domains can comprise a targeting polypeptide or the like. The "fusion" can be an association generated by a peptide bond, a chemical linking, a charge interaction (e.g., electrostatic attractions, such as salt bridges, H-bonding, etc.) or the like. If the polypeptides are recombinant, the "fusion protein" can be translated from a common mRNA. Alternatively, the compositions of the domains can be linked by any chemical or electrostatic means. The chimeric molecules of the invention (e.g., targeting polypeptide fusion proteins) can also include additional sequences, e.g., linkers, epitope tags, enzyme cleavage recognition sequences, signal sequences, secretion signals, and the like. Alternatively, a peptide can be linked to a carrier simply to facilitate manipulation or identification/location of the peptide.

Therapeutic Compositions and their Administration

A vaccine composition comprising the nucleic acid encoding the fusion polypeptide, or a cell expressing this nucleic acid is administered to a mammalian subject, preferably a human. The vaccine composition is administered in a pharmaceutically acceptable carrier in a biologically effective or a therapeutically effective amount, Certain preferred conditions are disclosed in the Examples. The composition may be given alone or in combination with another protein or peptide such as an immunostimulatory molecule. Treatment may include administration of an adjuvant, used in its broadest sense to include any nonspecific immune stimulating compound such as an interferon. Adjuvants contemplated herein include resorcinols, non-ionic surfactants such as polyoxyethylene oleyl ether and n-hexadecyl polyethylene ether.

A therapeutically effective amount is a dosage that, when given for an effective period of time, achieves the desired immunological or clinical effect.

A therapeutically active amount of a nucleic acid encoding the fusion polypeptide may vary according to factors such as the disease state, age, sex, and weight of the individual, and the ability of the peptide to elicit a desired response in the individual. Dosage regimes may be adjusted to provide the optimum therapeutic response. For example, several divided doses may be administered daily or the dose may be proportionally reduced as indicated by the exigencies of the therapeutic situation. A therapeutically effective amounts of the protein, in cell associated form may be stated in terms of the protein or cell equivalents.

Thus an effective amount is between about 1 nanogram and about 1 gram per kilogram of body weight of the recipient, more preferably between about 0.1 µg/kg and about 10 mg/kg, more preferably between about 1 µg/kg and about 1 mg/kg. Dosage forms suitable for internal administration preferably contain (for the latter dose range) from about 0.1 µg to 100 µg of active ingredient per unit. The active ingredient may vary from 0.5 to 95% by weight based on the total weight of the composition. Alternatively, an effective dose of cells expressing the nucleic acid is between about $10^4$ and $10^8$ cells. Those skilled in the art of immunotherapy will be able to adjust these doses without undue experimentation.

The active compound may be administered in a convenient manner, e.g., injection by a convenient and effective route. Preferred routes include intradermal "gene gun" delivery, and intramuscular routes. For the treatment of existing tumors which have not been completely resected or which have recurred, direct intratumoral injection may also be used.

Depending on the route of administration, the nucleic acid may be coated in a material to protect the compound from the action of enzymes, acids and other natural conditions which may inactivate the compound. Thus it may be necessary to coat the composition with, or co-administer the composition with, a material to prevent its inactivation. For example, an enzyme inhibitors of nucleases or proteases or in an appropriate carrier such as liposomes (including water-in-oil-in-water emulsions as well as conventional liposomes (Strejan et al., (1984) J. Neuroimmunol 7:27).

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

Preferred pharmaceutically acceptable diluents include saline and aqueous buffer solutions. Pharmaceutical compositions suitable for injection include sterile aqueous solutions (where water soluble) or dispersions and sterile powders for the extemporaneous preparation of sterile injectable solutions or dispersion. Isotonic agents, for example, sugars, polyalcohols such as mannitol, sorbitol, sodium chloride may be included in the pharmaceutical composition. In all cases, the composition should be sterile and should be fluid. It should be stable under the conditions of manufacture and storage and must include preservatives that prevent contamination with microorganisms such as bacteria and fungi. Dispersions can also be prepared in glycerol, liquid polyethylene glycols, and mixtures thereof and in oils. Under ordinary conditions of storage and use, these preparations may contain a preservative to prevent the growth of microorganisms.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal, and the like.

Compositions are preferably formulated in dosage unit form for ease of administration and uniformity of dosage. Dosage unit form refers to physically discrete units suited as unitary dosages for a mammalian subject; each unit contains a predetermined quantity of active material (e.g., the nucleic acid vaccine) calculated to produce the desired therapeutic effect, in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active compound for the treatment of, and sensitivity of, individual subjects Other pharmaceutically acceptable carriers for the nucleic acid vaccine compositions according to the present invention are liposomes, pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature. Those skilled in the art will appreciate other suitable embodiments of the present liposomal formulations.

Antigens Associated with Pathogens

A major use for the present invention is the use of the present nucleic acid compositions in therapeutic vaccine for cancer and for major chronic viral infections that cause morbidity and mortality worldwide. Such vaccines are designed to eliminate infected cells—this requires T cell responses as antibodies are often ineffective. The vaccines of the present invention are designed to meet these needs.

Preferred antigens are epitopes of pathogenic microorganisms against which the host is defended by effector T cells responses, including cytotoxic T lymphocyte (CTL) and delayed type hypersensitivity. These typically include viruses, intracellular parasites such as malaria, and bacteria that grow intracellularly such as Mycobacteria and *Listeria* species. Thus, the types of antigens included in the vaccine compositions of this invention are any of those associated with such pathogens (in addition, of course, to tumor-specific antigens). It is noteworthy that some viral antigens are also tumor antigens in the case where the virus is a causative factor in cancer.

In fact, the two most common cancers worldwide, hepatoma and cervical cancer, are associated with viral infection. Hepatitis B virus(HBV) (Beasley, R. P. et al., *Lancet* 2, 1129-1133 (1981) has been implicated as etiologic agent of hepatomas. 80-90% of cervical cancers express the E6 and E7 antigens (exemplified herein) from one of four "high risk" human papillomavirus types: HPV-16, HPV-18, HPV-31 and HPV-45 (Gissmann, L. et al., *Ciba Found Symp.* 120, 190-207 (1986); Beaudenon, S., et al. *Nature* 321, 246-249 (1986). The HPV E6 and E7 antigens are the most promising targets for virus associated cancers in immunocompetent individuals because of their ubiquitous expression in cervical cancer. In addition to their importance as targets for therapeutic cancer vaccines, virus associated tumor antigens are also ideal candidates for prophylactic vaccines. Indeed, introduction of prophylactic HBV vaccines in Asia have decreased the incidence of hepatoma (Chang, M. H., et al. *New Engl. J. Med.* 336, 1855-1859 (1997), representing a great impact on cancer prevention.

Among the most important viruses in chronic human viral infections are HPV, HBV, hepatitis C Virus (HCV), human immunodeficiency virus (HIV-1 and HIV-2), herpesviruses such as Epstein Barr Virus (EBV), cytomegalovirus (CMV) and HSV-1 and HSV-2 and influenza virus. Useful antigens include HBV surface antigen or HBV core antigen; ppUL83 or pp89 of CMV; antigens of gp120, gp41 or p24 proteins of HIV-1; ICP27, gD2, gB of HSV; or influenza nucleoprotein (Anthony, L S et al., *Vaccine* 1999; 17:373-83). Other antigens associated with pathogens that can be utilized as described herein are antigens of various parasites, includes malaria, preferably malaria peptide (NANP)40.

In addition to its applicability to human cancer and infectious diseases, the present invention is also intended for use in treating animal diseases in the veterinary medicine context. Thus, the approaches described herein may be readily applied by one skilled in the art to treatment of veterinary herpesvirus infections including equine herpesviruses, bovine viruses such as bovine viral diarrhea virus (for example, the E2 antigen), bovine herpesviruses, Marek's disease virus in chickens and other fowl; animal retroviral and lentiviral diseases (e.g., feline leukemia, feline immunodeficiency, simian immunodeficiency viruses, etc.); pseudorabies and rabies; and the like.

As for tumor antigens, any tumor-associated or tumor-specific antigen that can be recognized by T cells, preferably by CTL, can be used. In addition to the HPV-E7 antigen exemplified herein is mutant p53 or HER2/neu or a peptide thereof. Any of a number of melanoma-associated antigens may be used, such as MAGE-1, MAGE-3, MART-1/Melan-A, tyrosinase, gp75, gp100, BAGE, GAGE-1, GAGE-2, GnT-V, and p15 (see, U.S. Pat. No. 6,187,306).

The following references set forth principles and current information in the field of basic, medical and veterinary virology and are incorporated by reference: *Fields Virology*, Fields, B N et al., eds., Lippincott Williams & Wilkins, NY, 1996; *Principles of Virology: Molecular Biology, Pathogenesis, and Control*, Flint, S. J. et al., eds., Amer Society for Microbiology, Washington, 1999; *Principles and Practice of*

*Clinical Virology*, 4th Edition, Zuckerman. A. J. et al., eds., John Wiley & Sons, NY, 1999; *The Hepatitis C Viruses*, by Hagedorn, C H et al., eds., Springer Verlag, 1999; *Hepatitis B Virus: Molecular Mechanisms in Disease and Novel Strategies for Therapy*, Koshy, R. et al., eds, World Scientific Pub Co, 1998; *Veterinary Virology*, Murphy, F. A. et al., eds., Academic Press, NY, 1999; *Avian Viruses: Function and Control*, Ritchie, B. W., Iowa State University Press, Ames, 2000; *Virus Taxonomy: Classification and Nomenclature of Viruses: Seventh Report of the International Committee on Taxonomy of Viruses*, by M. H. V. Van Regenmortel, MHV et al., eds., Academic Press; NY, 2000.

Delivery of Vaccine Nucleic Acid to Cells and Animals

The Examples below describe certain preferred approaches to delivery of the vaccines of the present invention. A broader description of other approaches including viral and nonviral vectors and delivery mechanisms follow.

DNA delivery involves introduction of a "foreign" DNA into a cell ex vivo and ultimately, into a live animal or directly into the animal. Several general strategies for gene delivery (=delivery of nucleic acid vectors) for purposes that include "gene therapy" have been studied and reviewed extensively (Yang, N-S., *Crit. Rev. Biotechnol.* 12:335-356 (1992); Anderson, W. F., *Science* 256:808-813 (1992); Miller, A. S., *Nature* 357:455-460 (1992); Crystal, R. G., *Amer. J. Med.* 92(suppl 6A):44S-52S (1992); Zwiebel, J. A. et al., *Ann. N.Y. Acad. Sci.* 618:394-404 (1991); McLachlin, J. R. et al., *Prog. Nucl. Acid Res. Molec. Biol.* 38:91-135 (1990); Kohn, D. B. et al., *Cancer Invest.* 7:179-192 (1989), which references are herein incorporated by reference in their entirety).

For accomplishing the objectives of the present invention, nucleic acid therapy would be accomplished by direct transfer of a the functionally active DNA into mammalian somatic tissue or organ in vivo. DNA transfer can be achieved using a number of approaches described herein. These systems can be tested for successful expression in vitro by use of a selectable marker (e.g., G418 resistance) to select transfected clones expressing the DNA, followed by detection of the presence of the antigen-containing expression product (after treatment with the inducer in the case of an inducible system) using an antibody to the product in an appropriate immunoassay. Efficiency of the procedure, including DNA uptake, plasmid integration and stability of integrated plasmids, can be improved by linearizing the plasmid DNA using known methods, and co-transfection using high molecular weight mammalian DNA as a "carrier".

In addition to virus-mediated gene transfer in vivo, physical means well-known in the art can be used for direct transfer of DNA, including administration of plasmid DNA (Wolff et al., 1990, supra) and particle-bombardment mediated gene transfer (Yang, N.-S., et al., *Proc. Natl. Acad. Sci. USA* 87:9568 (1990); Williams, R. S. et al., *Proc. Natl. Acad. Sci. USA* 88:2726 (1991); Zelenin, A. V. et al., *FEBS Lett.* 280:94 (1991); Zelenin, A. V. et al., *FEBS Lett.* 244:65 (1989); Johnston, S. A. et al., *In Vitro Cell. Dev. Biol.* 27:11 (1991)). Furthermore, electroporation, a well-known means to transfer genes into cell in vitro, can be used to transfer DNA molecules according to the present invention to tissues in vivo (Titomirov, A. V. et al., *Biochim. Biophys. Acta* 1088:131 ((1991)).

"Carrier mediated gene transfer" has also been described (Wu, C. H. et al., *J. Biol. Chem.* 264:16985 (1989); Wu, G. Y. et al., *J. Biol. Chem.* 263:14621 (1988); Soriano, P. et al., *Proc. Natl. Acad. Sci. USA* 80:7128 (1983); Wang, C-Y. et al., *Proc. Natl. Acad. Sci. USA* 84:7851 (1982); Wilson, J. M. et al., *J. Biol. Chem.* 267:963 (1992)). Preferred carriers are targeted liposomes (Nicolau, C. et al., *Proc. Natl. Acad. Sci. USA* 80:1068 (1983); Soriano et al., supra) such as immunoliposomes, which can incorporate acylated mAbs into the lipid bilayer (Wang et al., supra). Polycations such as asialoglycoprotein/polylysine (Wu et al., 1989, supra) may be used, where the conjugate includes a molecule which recognizes the target tissue (e.g., asialoorosomucoid for liver) and a DNA binding compound to bind to the DNA to be transfected. Polylysine is an example of a DNA binding molecule which binds DNA without damaging it. This conjugate is then complexed with plasmid DNA according to the present invention for transfer.

Plasmid DNA used for transfection or microinjection may be prepared using methods well-known in the art, for example using the Quiagen procedure (Quiagen), followed by DNA purification using known methods, such as the methods exemplified herein.

Having now generally described the invention, the same will be more readily understood through reference to the following examples which are provided by way of illustration, and are not intended to be limiting of the present invention, unless specified.

EXAMPLE I

Materials and Methods

Mice: Six- to eight-week-old female C57BL/6 mice were purchased from the National Cancer Institute (Frederick, Md.) and kept in the oncology animal facility of the Johns Hopkins Hospital (Baltimore, Md.). All animal procedures were performed according to approved protocols and in accordance with the recommendations for the proper use and care of laboratory animals.

Plasmid DNA Construction: The E7/70 gene was cloned into pNGVL4a (National Gene Vector Laboratory) using the EcoRI and KpnI restriction sites. Using site-directed mutagenesis, two point mutations, which had previously been found to reduce Rb binding (Munger, K et al., *EMBO J* 1989, 8:4099-4105), were introduced into the E7 gene. The primers used to introduce these mutations were as follows:

```
mE7 Forward:
                                    [SEQ ID NO: 14]
5' ctgatctctacggttatgggcaattaaatgacagetc 3'
and mE7 Reverse:
                                    [SEQ ID NO: 15]
5' gagctgtcatttaattgcccataaccgtagagatca 3'.
```

For construction of pNGVL4a-Sig/E7(detox)/HSP70, Sig was cut from pCMV-neoSig/E7/LAMP-1 (Chen, C H et al., *Gene Ther* 1999, 6:1972-1981) by EcoRI/NsiI, and E7(detox)/HSP70 was cut from pNGVL4a-E7(detox)/HSP70 by NsiI/XbaI. Sig and E7(detox)/HSP70 were ligated and cloned into pNGVL4a vector cut with EcoRI/XbaI. The accuracy of DNA constructs was confirmed by DNA sequencing.

The production and maintenance of TC-1 cells has been described previously (Lin, K Y et al., *Cancer Res* 1996, 56:21-26.). In brief, HPV-16 E6, E7 and ras oncogene were used to transform primary C57BL/6 mice lung epithelial cells to generate TC-1.

Needle IM Mediated DNA Vaccination: The pNGVL4a-Sig/E7(detox)/HSP70 vaccine was administered to groups of mice by three different methods. For needle i.m. mediated DNA vaccination, 50 μg/mouse of pNGVL4a-Sig/E7(detox)/HSP70 DNA vaccines were delivered intramuscularly by syringe needle injection. The dose was chosen based on the optimal dosage conditions most commonly used in other studies [Gurunathan, S et al., *Annu Rev Immunol* 2000, 18:927-974]. These mice received a booster with the same regimen one week later.

Biojector Mediated DNA Vaccination: The Biojector 2000 (Bioject Inc., Portland, Oreg.) is a needle-free jet injection device consisting of an injector and a disposable syringe. The orifice size controls the depth of penetration. 50 μg/mouse of pNGVL4a-Sig/E7(detox)/HSP70 were delivered to the shaved flank region of C57BL/6 mice using the Biojector with no. 2 syringe nozzle. We have adopted the same dosage used in needle i.m. for the biojector administrations. These mice received a booster with the same regimen one week later.

Gene Gun Mediated DNA Vaccination: DNA-coated gold particles (1 μg DNA/bullet) were delivered to the shaved abdominal region of C57BL/6 mice using a helium-driven gene gun (BioRad, Hercules, Calif.) with a discharge pressure of 400 p.s.i. C57BL/6 Mice were vaccinated via gene gun with 2 μg of pNGVL4a-Sig/E7(detox)/HSP70 DNA vaccine. The dose was chosen based on the optimal dosage conditions most commonly used in other studies (Gurunathan et al., supra). These mice received a booster with the same regimen one week later.

Intracellular Cytokine Staining with Flow Cytometry Analysis to Detect IFN-γ Secretion by E7-Specific $CD8^+$ T Cells: Cell surface marker staining for CD8 and intracellular cytokine staining for IFN-γ as well as FACScan analysis were performed using conditions described previously (Chen, C H et al., *Vaccine* 2000, 18:2015-2022). Prior to FACScan, splenocytes from different vaccinated groups of mice were collected and incubated for 20 hours either with or without 1 μg/ml of E7 peptide (aa 49-57, RAHYNIVTF (SEQ ID NO:16) [Feltkamp, M C et al., *Eur J Immunol* 1993, 23:2242-2249] containing an MHC class I epitope for detecting E7-specific CD8 T cell precursors. The number of IFN-γ-secreting $CD8^+$ T cells was analyzed using flow cytometry. Analysis was performed on a Becton-Dickinson FACScan with CELLQuest software (Becton Dickinson Immunocytometry System, Mountain View, Calif.).

In vivo Tumor Treatment Experiment: An in vivo tumor treatment experiment was performed using the conditions described previously (Ji, H et al., Int J Cancer 1998, 78:41-45]. Mice (5 per group) were intravenously challenged with $1 \times 10^4$ cells/mouse TC-1 tumor cells via tail vein. Three days after tumor challenge, mice were administered 50 μg/mouse of DNA vaccine by i.m. or biojector or were administered 2 μg/mouse of DNA vaccine by gene gun. One week after the first vaccination, these mice were boosted with the same regimen and method as the first vaccination. Mice were sacrificed and lungs were explanted on day 28 after TC-1 challenge. The number of pulmonary tumor nodules and the total pulmonary weight in each mouse were evaluated.

In Vivo Tumor Protection Experiment: An in vivo tumor protection experiment was performed using the conditions described previously [Lin et al., supra]. Mice (5 per group) received 50 μg/mouse of DNA vaccines by i.m. or biojector, or mice received 2 μg/mouse by gene gun. One week later, mice were boosted with the same regimen and method as the first vaccination. Mice were subcutaneously challenged with $5 \times 10^4$ cells/mouse TC-1 tumor cells one week after the last vaccination. Tumor growth was examined by palpation and inspection twice a week. Percentage of tumor free mice were recorded.

Statistical Analysis: All data expressed as means±SE are representative of at least two different experiments. Data for intracellular cytokine staining with flow cytometry analysis and tumor treatment experiments were evaluated by analysis of variance (ANOVA). Comparisons between individual data points were made using a student's t-test. In the tumor protection experiment, the principal outcome of interest was time to development of tumor. The event time distributions for different mice were compared by use of the method of Kaplan and Meier and by use of the log—

EXAMPLE II pNGVL4a-Sig/E7(detox)/FISP70 DNA Vector Administered by Gene Gun Generated Highest Number of E7-specific $CD8^+$ T Cells in Immunized Mice This study compared the ability of the pNGVL4a-Sig/E7 (detox)/HSP70 DNA vaccine composition to generate E7-specific $CD8^+$ T cell precursors by evaluation intracellular cytokines in splenocytes from mice vaccinated with the same DNA construct by three different modes of administration: needle i.m., biojector, and gene gun. Splenocytes from nave or immunized vaccinated groups of mice were incubated with or without the MHC class I (H-2 $D^b$)-restricted E7 peptide (aa 49-57) (SEQ ID NO:2) to detect E7-specific $CD8^+$ T cells.

Figure 1B:
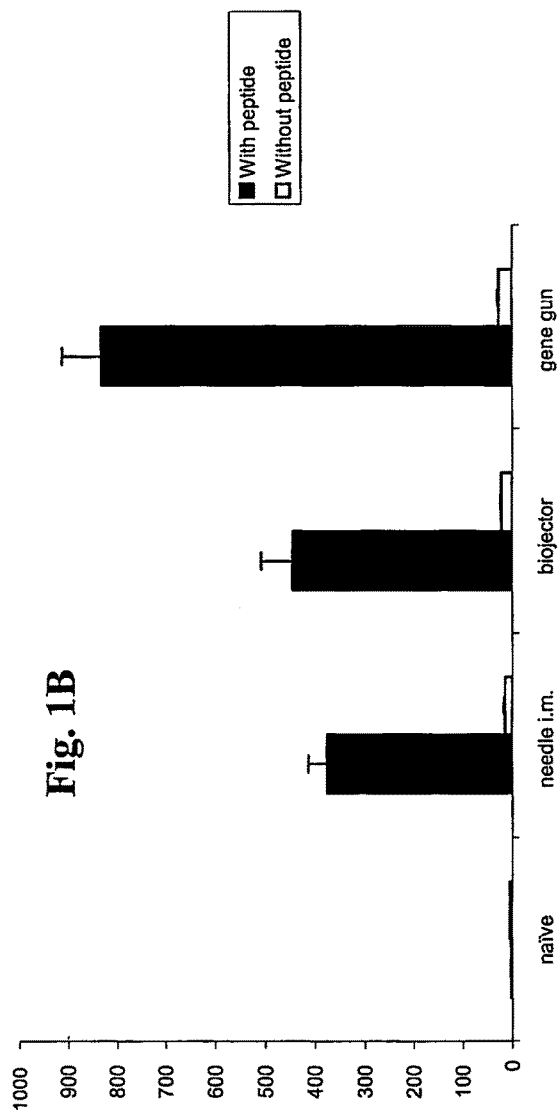

Results are shown in FIGS. 1A and 1B/Mice vaccinated via gene gun exhibited significantly higher numbers ($p<0.05$) of E7-specific IFN-$γ^+$ $CD8^+$ T cell precursors per fixed number of splenocyte (832.5) compared to mice vaccinated via biojector (445.5) and needle i.m. (375.5). These findings suggest that the gene gun approach was somewhat more potent in this setting. However, i.m. injection was also effective.

EXAMPLE III

Vaccinated Mice were Protected In Vivo Against E7-Expressing Tumors

The next study investigated protection against TC-1 tumor, expressing the same antigen, E7, as the pNGVL4a-Sig/E7(detox)/HSP70 vaccine, administered by the three routes. In vivo tumor protection experiment (vaccination before tumor challenge) used the well-characterized E7-expressing tumor model, TC-1. As shown in FIG. 2, mice receiving pNGVL4a-Sig/E7(detox)/HSP70 via gene gun, biojector, or needle i.m. remained 100% tumor free after TC-1 tumor challenge. Thus, this vaccine vector administered by different routes generated total protection against growth of later-administered tumor cells expressing the E7 antigen.

EXAMPLE IV

The E7 Vaccine was Therapeutic in Mice Bearing the TC-1 Tumor

Figure 3:
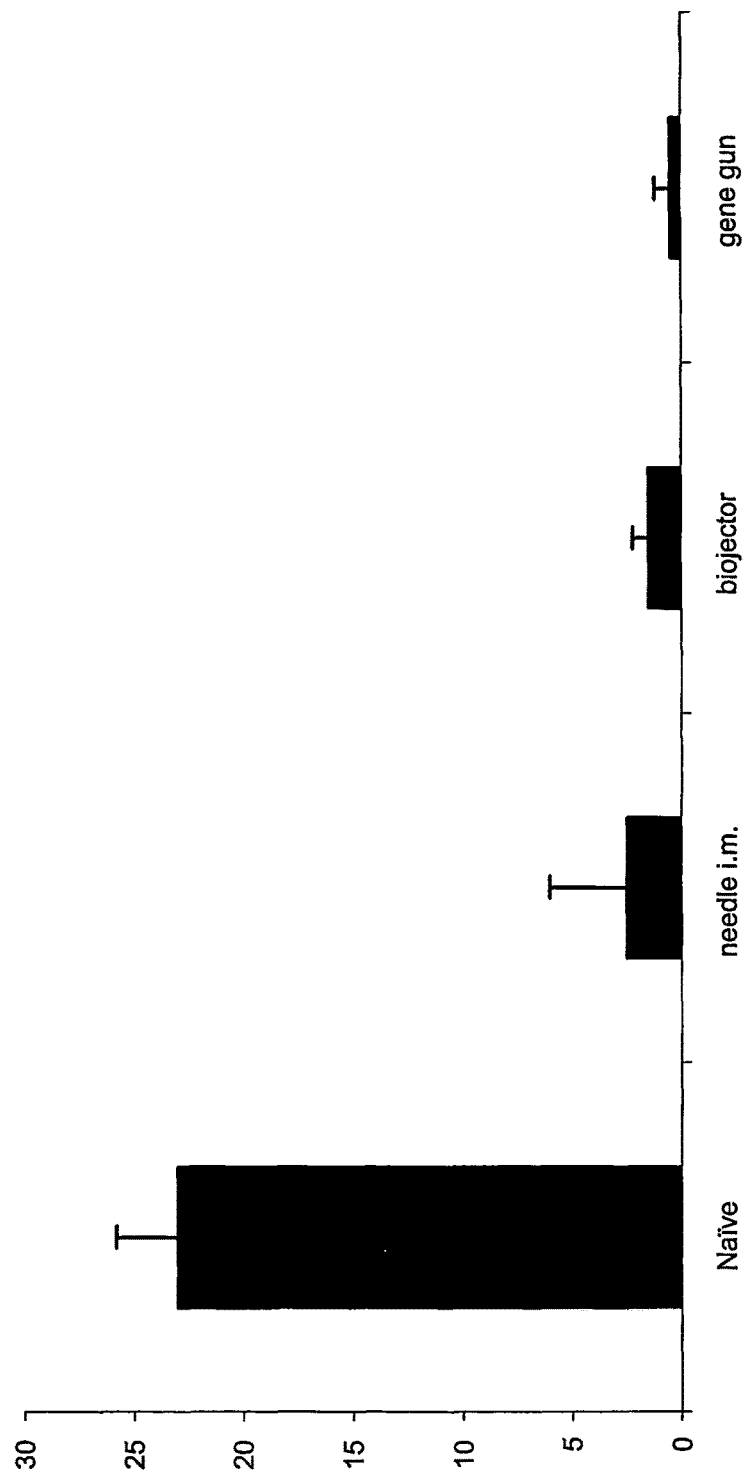
FIGS. 3 and 4 are graphs showing results of in vivo tumor treatment experiments comparing antitumor effects of the vaccine delivered by different routes. Mice were inoculated i.v. with $10^4$ TC-1 tumor cells via the tail vein and were subsequently treated with the DNA vaccine administered via needle i.m., by biojector. and by gene gun.
Figure 4:
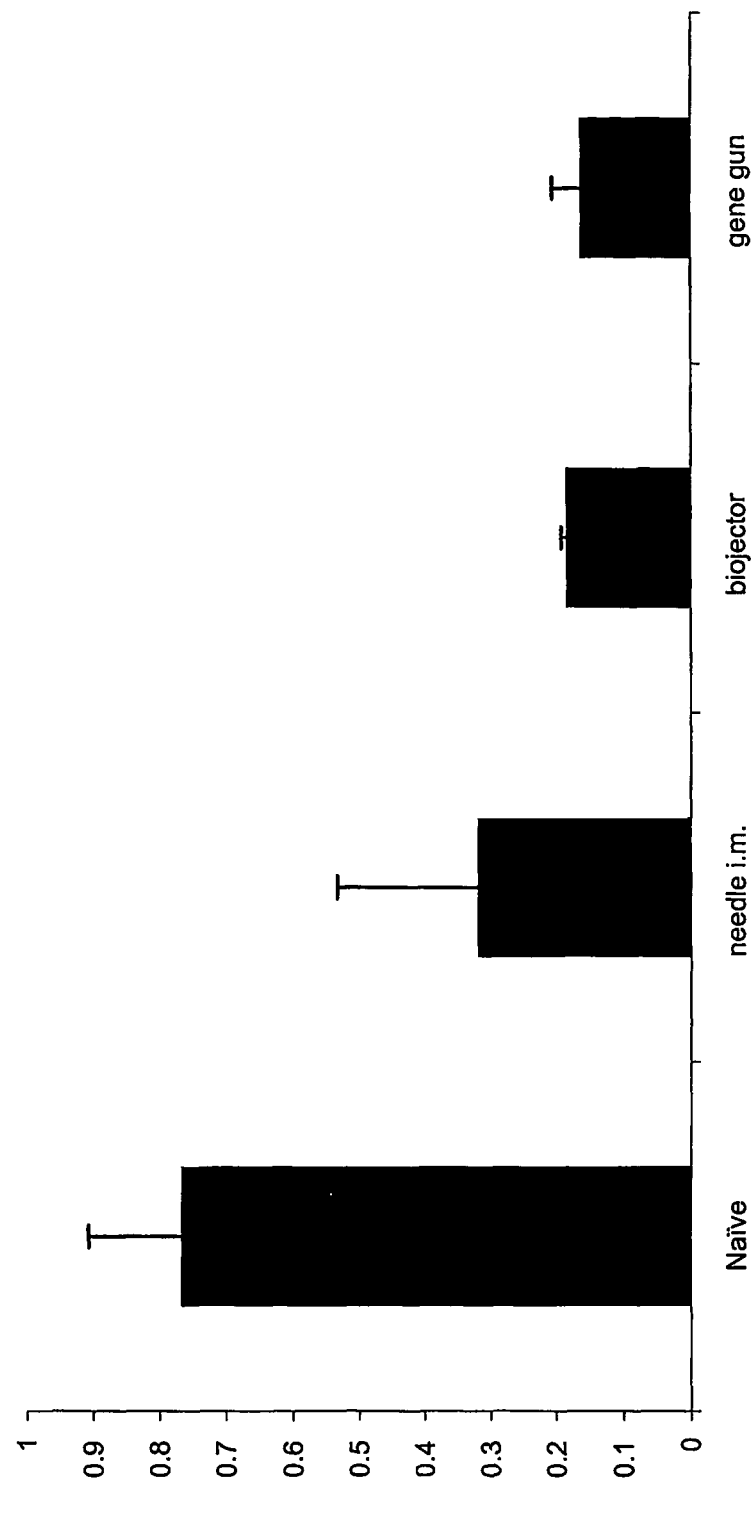

Sig/E7(detox)/HSP70 vaccine was administered to mice bearing the TC-1 tumor under conditions where, in untreated controls, tumor metastasis to the lungs occurred by hematogenous spread. Metastasis was assessed by enumeration of lung nodules and by weighing lungs. As shown in FIGS. 3 and 4, mice receiving pNGVL4a-Sig/E7(detox)/HSP70 via gene gun exhibited the lowest number of pulmonary nodules and lowest pulmonary weight of the three groups of vaccinated mice and naive controls. The differences between the three vaccinated groups did not reach statistical significance.

Furthermore, the variance (standard deviation and standard error (SE)) in the number of pulmonary nodules and pulmonary weight was smaller in the animals vaccinated by gene gun and biojector as compared to the groups vaccinated by injection i.m. with a syringe.

Discussion of Examples I-IV

The foregoing studies focused on the immune and antitumor responses of mice immunized with pNGVL4a-Sig/E7(detox)/HSP70 DNA vaccine administered via needle i.m., biojector, and gene gun in mice. The studies employed doses and conditions shown by the present inventors and their colleagues to be optimal The results indicated that the DNA vaccine administered via gene gun generated the highest immune response, measured as the number of E7-specific $CD8^+$ T cells. The efficacy of this approach was further supported by the fact that gene gun immunization required the least amount of the immunogen to generate a similar or slightly higher antitumor effects.

These observed differences may be attributable to the capacity of these routes of administration to generate professional antigen presenting cells (APCs) that express the antigen. Intradermal immunization by gene gun can directly target antigen to the skin's professional APCs-, Langerhans cells (Condon, C et al., Nat Med 1996, 2:1122-1128; Porgador, A et al., J Exp Med 1998, 188:1075-1082), allowing improved direct presentation of antigen to T cells by DNA-transfected DCs. In comparison, intramuscular immunization likely targets antigen to myocytes and the antigen encoded by the DNA vaccine is eventually is presented through bone marrow-derived APCs [Fu, T M et al., Mol Med 1997, 3(6), 362-37119]. In this setting, the number of professional APCs expressing antigen may be lower. In these ways, it appears that the route of administration may influence the ability of the present inventors' strategy to enhance DNA vaccine potency.

Although gene gun-mediated vaccination may have generated the highest number of antigen-specific $CD8^+$ T cells, mice receiving the DNA vector via all three routes were protected, remaining 100% tumor free, after TC-1 tumor challenge (FIG. 2). It may be that that the experimental window (i.e., time frame of observation and size of tumor inoculum) may not have been sufficient to allow a clear distinction among the three routes.

However, using a more stringent tumor treatment model, only slight and statistically insignificant differences were observed in the number of pulmonary nodules and pulmonary weight among the mice vaccinated with syringe, biojector, and gene gun.

CD8+ T cells are clearly important for the observed antitumor effects of the pNGVL4a-Sig/E7(detox)/HSP70 DNA vaccine.

Using human papillomavirus type 16 E7 as a model antigen, the present inventors and colleagues previously evaluated the impact of linking antigen-encoding DNA to DNA encoding HSP70 on the potency of antigen-specific immunity generated by naked DNA vaccines. Vaccines comprising E7-HSP70 fusion genes increased the frequency of E7-specific CD8+ T cells relative to vaccines containing the wild-type E7 gene alone. More importantly, in vivo antibody depletion experiment demonstrated that E7-HSP70 fusion vaccines exclusively targeted CD8+ T cells; immunological and antitumor effects were completely independent of CD4+ T cells and NK cells.

The addition of a signal peptide (Sig) to E7/HSP70 may lead to exogenous release of chimeric E7/HSP70 protein. Suto et al. Science 1995, 269:1585-1588, demonstrated that an exogenous antigen chaperoned by a heat shock protein can be channeled into the endogenous pathway, presented by MHC class I molecules, and recognized by CD8+ T lymphocytes in the classical phenomenon known as "cross-priming." Additionally, in vivo studies by Chu et. al., Clin Exp Immunol 2000, 121:216-225, using mice depleted of CD8 or CD4 lymphocyte subsets demonstrated that tumor regression following therapeutic hspE7 protein immunization was CD8-dependent and CD4-independent. Moreover, Huang et al. J Exp Med 2000, 191:403-408, showed that Hsp70 fusion proteins elicit CD4-independent CTL responses. Thus, there are several bases for the conclusion that fusion of HSP70 to E7 enhances the potency of vaccines via CD8-dependent pathways.

The administration of the pNGVL4a-Sig/E7(detox)/HSP70 DNA vaccine via the gene gun and biojector may provide more consistency (i.e., lower variance) than intramuscular administration via syringe. Results appearing in FIGS. 3 and 4 showed that the variance in the number of pulmonary nodules and pulmonary weight was smaller when the DNA vaccine is administered by gene gun and biojector than by syringe.

Thus, it appears that the instrumentation and method of delivery may influence the consistency of response to this vaccine. Both the gene gun apparatus and the biojector device utilize a standard mechanical method of delivering DNA and may avoid some of the inconsistency introduced by a method that is inherently more variable. Results of previous studies suggested that the biojector apparatus may be a more consistent means than a syringe in delivering such vaccines (Lemon, S M et al., J Med Virol 1983, 12:129-136; Aguiar, J C et al., Vaccine 2001, 20:275-280; Rogers, W O et al., Infect Immun 2001, 69:5565-5572).

For mass immunization of humans, safety is an important consideration. First, the DNA may integrate into the host genome, resulting in the inactivation of tumor suppresser genes or the activation of oncogenes which could lead to malignant transformation of the host cell. Because it is estimated that the frequency of integration is much lower than that of spontaneous mutation, integration should not pose any real risk (Nichols, W W et al., Ann N Y Acad Sci 1995, 772:30-39). A second concerns is the potential risk associated with the presence of HPV-16 E7 oncoprotein in host cells. The same concern holds true for the HPV E6 protein. E7 is an oncoprotein that disrupts cell cycle regulation by binding to tumor suppressor pRB protein in nuclei [Lukas, J, J Cell Biol 1994, 125:625-638]. The presence of E7 in host cells may lead to an accumulation of genetic aberrations and eventual malignant transformation. The pNGVL4a-Sig/E7(detox)/HSP70 DNA vaccine allays the latter concern by introducing two key mutations into E7 which preserve its immunogenicity but alleviate its oncogenicity by destroying its ability to bind pRB. A third concern is the risk of inducing for autoimmunity mediated by CTL clones specific for mycobacterial HSP that might cross-react to host HSP. Pathological examination of the vital organs in the pNGVL4a-Sig/E7(detox)/HSP70 DNA vaccinated mice (and recipients of all other similar DNA vaccines that the present inventors have tested) did not reveal any detrimental or other autoimmune pathology.

In summary, as shown herein, vaccination with pNGVL4a-Sig/E7(detox)/HSP70 DNA is a safe and effective way to enhance antigen-specific CD8⁺ T cell immune responses and antigen-specific antitumor effects.

The references cited above are all incorporated by reference herein, whether specifically incorporated or not. All publications, patents, patent applications, GenBank sequences and ATCC deposits, cited herein are hereby expressly incorporated by reference for all purposes.

Citation of the documents herein is not intended as an admission that any of them is pertinent prior art. All statements as to the date or representation as to the contents of these documents is based on the information available to the applicant and does not constitute any admission as to the correctness of the dates or contents of these documents.

The invention claimed is:

1. A nucleic acid molecule encoding a fusion polypeptide useful as a vaccine composition, which molecule comprises:
   (a) a first nucleic acid sequence encoding a first polypeptide or peptide that promotes processing via the MHC class I pathway,
   wherein the first polypeptide or peptide is encoded by
      (i) SEQ ID NO: 9; or
      (ii) comprises the amino acid sequence of SEQ ID NO: 10; or
      (iii) comprises an active C-terminal domain of the polypeptide or peptide encoded by (i) or comprising (ii);
   (b) fused in frame with the first nucleic acid sequence, a second nucleic acid sequence encoding a signal peptide for secreting the fusion polypeptide; and
   (c) a third nucleic acid sequence that is linked in frame to said first nucleic acid sequence and that encodes a non-oncogenic mutant of an E7 polypeptide of HPV-16 having the sequence SEQ ID NO: 2, said mutant of SEQ ID NO: 2 comprises a Glycine at positions 24 and 26, wherein positions 24 and 26 correspond to positions 24 and 26 of SEQ ID NO: 2.

2. The nucleic acid molecule of claim 1, that is characterized as pNGVL4a-Sig/E7 (detox)/HSP70, and has the sequence SEQ ID NO: 13.

3. An expression vector comprising the nucleic acid molecule of claim 1 operatively linked to
   (a) a promoter; and
   (b) optionally, additional regulatory sequences that regulate expression of said nucleic acid in a eukaryotic cell.

4. The expression vector of claim 3, which comprises plasmid PNGVL4a.

5. A pharmaceutical composition comprising:
   (a) pharmaceutically and immunologically acceptable excipient in combination with;
   (b) the nucleic acid molecule of claim 1.

6. A pharmaceutical composition comprising:
   (a) pharmaceutically and immunologically acceptable excipient in combination with;
   (b) the nucleic acid molecule of claim 2.

7. A pharmaceutical composition comprising:
   (a) pharmaceutically and immunologically acceptable excipient in combination with;
   (b) the expression vector of claim 3.

8. A pharmaceutical composition immune response, comprising:
   (a) pharmaceutically and immunologically acceptable excipient in combination with;
   (b) the expression vector of claim 4.

9. A method of inducing or enhancing a HPV antigen specific immune response in a subject comprising administering to the subject an effective amount of the pharmaceutical composition of claim 7, thereby inducing or enhancing said response.

10. A method of inducing or enhancing a HPV antigen specific immune response in a subject comprising administering to the subject an effective amount of the pharmaceutical composition of claim 8, thereby inducing or enhancing said response.

11. The method of claim 9, wherein said subject is a human.

12. The method of claim 10, wherein said subject is a human.

13. The method of claim 11, wherein said administering is by an intramuscular injection by gene gun administration or by needle-free jet injection.

14. The method of claim 12, wherein said administering is by an intramuscular injection by gene gun administration or by needle-free jet injection.

15. The nucleic acid molecule of claim 1, wherein the mutant of SEQ ID NO: 2 further comprises a Glycine or Alanine substitution at position 91, wherein position 91 corresponds to position 91 of SEQ ID NO: 2.

16. A pharmaceutical composition comprising:
   (a) pharmaceutically and immunologically acceptable excipient in combination with;
   (b) the nucleic acid molecule of claim 15.

* * * * *

UNITED STATES PATENT AND TRADEMARK OFFICE
CERTIFICATE OF CORRECTION

PATENT NO. : 9,701,725 B2
APPLICATION NO. : 10/555669
DATED : July 11, 2017
INVENTOR(S) : Tzyy-Choou Wu and Chien-Fu Hung Page 1 of 1

It is certified that error appears in the above-identified patent and that said Letters Patent is hereby corrected as shown below:

In the Specification

Column 1 Line 5 immediately after the title please insert the following paragraph (government support statement):
--STATEMENT OF GOVERNMENTAL INTEREST
This invention was made with government support under grant number CA083706, awarded by the National Institutes of Health. The government has certain rights in the invention.--

Signed and Sealed this
Sixth Day of February, 2018

Joseph Matal
*Performing the Functions and Duties of the*
*Under Secretary of Commerce for Intellectual Property and*
*Director of the United States Patent and Trademark Office*

UNITED STATES PATENT AND TRADEMARK OFFICE
CERTIFICATE OF CORRECTION

PATENT NO. : 9,701,725 B2
APPLICATION NO. : 10/555669
DATED : July 11, 2017
INVENTOR(S) : Tzyy-Choou Wu et al.

Page 1 of 1

It is certified that error appears in the above-identified patent and that said Letters Patent is hereby corrected as shown below:

In the Specification

1. Please correct SEQ ID NO.: 9 at Column 20 as follows:
Sequence 79-88 (Lines 2-3), replace "cccggtcgtc tcggccaact" with --cccggtcgtc gtcgccaact--;
Sequence 279-298 (Line 8), replace "accgcattctg tgaagctga" with --ccgcattctg atgaagctga--.

2. Please correct SEQ ID NO.: 10 at Column 22 as follows:
Sequence 541-550 (Line 10), replace "KNKVDAAVAE" with --LNKVDAAVAE--.

3. Please correct SEQ ID NO.: 13 at Columns 25-31 as follows:
At Column 25, sequence 771-780, replace "AGGCACGTAT" with --AGGCACCTAT--;
At Column 27, sequence 1911-1920, replace "CCGTTATTGA" with --CCGTTATTCA--;
At Column 27, sequence 1981-1990, replace "CAGGAATGGA" with --CAGGAATCGA--;
At Column 27, sequence 2341-2350, replace "TTAATCGGGG" with --TTAATCGCGG--;
At Column 27, sequence 2591-2600, replace "TCCGGGCACA" with --TCCGCGCACA--;
At Column 29, sequence 3541-3550, replace "ATTGACGGAA" with --ATTGACGCAA--;
At Column 29, sequence 3731-3740, replace "GTAAGTTCCG" with --GTAAGTACCG--;
At Column 29, sequence 4031-4040, replace "ATATGGAATT" with --ATATCGAATT--;
At Column 29, between Lines 32 and 33, insert:
--5051 GACCAGCGGG TCGTCGATTG GCTGGTGGAC AAGTTCAAGG GCACCAGCGG--;
At Column 29, sequence 5321-5330, replace "TCGGTGATGG" with --TCGGTGATCG--.

Signed and Sealed this
Fifteenth Day of December, 2020

Andrei Iancu
*Director of the United States Patent and Trademark Office*

SEQUENCE LISTING

```
<160> NUMBER OF SEQ ID NOS: 20

<210> SEQ ID NO 1
<211> LENGTH: 297
<212> TYPE: DNA
<213> ORGANISM: Human papillomavirus
<220> FEATURE:
<221> NAME/KEY: CDS
<222> LOCATION: (1)..(297)

<400> SEQUENCE: 1 atg cat gga gat aca cct aca ttg cat gaa tat atg tta gat ttg caa      48
Met His Gly Asp Thr Pro Thr Leu His Glu Tyr Met Leu Asp Leu Gln
1               5                   10                  15 cca gag aca act gat ctc tac tgt tat gag caa tta aat gac agc tca      96
Pro Glu Thr Thr Asp Leu Tyr Cys Tyr Glu Gln Leu Asn Asp Ser Ser
                20                  25                  30 gag gag gag gat gaa ata gat ggt cca gct gga caa gca gaa ccg gac     144
Glu Glu Glu Asp Glu Ile Asp Gly Pro Ala Gly Gln Ala Glu Pro Asp
            35                  40                  45 aga gcc cat tac aat att gta acc ttt tgt tgc aag tgt gac tct acg     192
Arg Ala His Tyr Asn Ile Val Thr Phe Cys Cys Lys Cys Asp Ser Thr
        50                  55                  60 ctt cgg ttg tgc gta caa agc aca cac gta gac att cgt act ttg gaa     240
Leu Arg Leu Cys Val Gln Ser Thr His Val Asp Ile Arg Thr Leu Glu
65                  70                  75                  80 gac ctg tta atg ggc aca cta gga att gtg tgc ccc atc tgt tct cag     288
Asp Leu Leu Met Gly Thr Leu Gly Ile Val Cys Pro Ile Cys Ser Gln
                85                  90                  95 gat aag ctt                                                         297
Asp Lys Leu <210> SEQ ID NO 2
<211> LENGTH: 99
<212> TYPE: PRT
<213> ORGANISM: Human papillomavirus

<400> SEQUENCE: 2

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Asp Lys Leu

<210> SEQ ID NO 3
```

```
<211> LENGTH: 98
<212> TYPE: PRT
<213> ORGANISM: Human papillomavirus

<400> SEQUENCE: 3

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 4
<211> LENGTH: 158
<212> TYPE: PRT
<213> ORGANISM: Human papillomavirus

<400> SEQUENCE: 4

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
                20                  25                  30

Ile Ile Leu Glu Cys Val Tyr Cys Lys Gln Gln Leu Leu Arg Arg Glu
            35                  40                  45

Val Tyr Asp Phe Ala Phe Arg Asp Leu Cys Ile Val Tyr Arg Asp Gly
50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
            115                 120                 125

Lys Gln Arg Phe His Asn Ile Arg Gly Arg Trp Thr Gly Arg Cys Met
            130                 135                 140

Ser Cys Cys Arg Ser Ser Arg Thr Arg Glu Thr Gln Leu
145                 150                 155

<210> SEQ ID NO 5
<211> LENGTH: 151
<212> TYPE: PRT
<213> ORGANISM: Human papillomavirus

<400> SEQUENCE: 5

Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
                20                  25                  30

Cys Lys Gln Gln Leu Leu Arg Arg Glu Val Tyr Asp Phe Ala Phe Arg
```

```
                35                  40                  45
Asp Leu Cys Ile Val Tyr Arg Asp Gly Asn Pro Tyr Ala Val Cys Asp
 50                  55                  60

Lys Cys Leu Lys Phe Tyr Ser Lys Ile Ser Glu Tyr Arg His Tyr Cys
 65                  70                  75                  80

Tyr Ser Leu Tyr Gly Thr Thr Leu Glu Gln Gln Tyr Asn Lys Pro Leu
                 85                  90                  95

Cys Asp Leu Leu Ile Arg Cys Ile Asn Cys Gln Lys Pro Leu Cys Pro
                100                 105                 110

Glu Glu Lys Gln Arg His Leu Asp Lys Lys Gln Arg Phe His Asn Ile
            115                 120                 125

Arg Gly Arg Trp Thr Gly Arg Cys Met Ser Cys Cys Arg Ser Ser Arg
130                 135                 140

Thr Arg Arg Glu Thr Gln Leu
145                 150

<210> SEQ ID NO 6
<211> LENGTH: 378
<212> TYPE: DNA
<213> ORGANISM: Human papillomavirus

<400> SEQUENCE: 6
atggcggccc ccggcgcccg gcggccgctg ctcctcctgc tgctggcagg ccttgcacat      60
ggcgcctcag cactctttga ggatctaatc atgcatggag atacacctac attgcatgaa     120
tatatgttag atttgcaacc agagacaact gatctctact gttatgagca attaaatgac     180
agctcagagg aggaggatga aatagatggt ccagctggac aagcagaacc ggacagagcc     240
cattacaata ttgtaacctt ttgttgcaag tgtgactcta cgcttcggtt gtgcgtacaa     300
agcacacacg tagacattcg tactttggaa gacctgttaa tgggcacact aggaattgtg     360
tgccccatct gttctcaa                                                   378

<210> SEQ ID NO 7
<211> LENGTH: 127
<212> TYPE: PRT
<213> ORGANISM: Human papillomavirus

<400> SEQUENCE: 7

Met Ala Ala Pro Gly Ala Arg Arg Pro Leu Leu Leu Leu Leu Leu Ala
  1               5                  10                  15

Gly Leu Ala His Gly Ala Ser Ala Leu Phe Glu Asp Leu Ile Met His
                 20                  25                  30

Gly Asp Thr Pro Thr Leu His Glu Tyr Met Leu Asp Leu Gln Pro Glu
             35                  40                  45

Thr Thr Asp Leu Tyr Cys Tyr Glu Gln Leu Asn Asp Ser Ser Glu Glu
 50                  55                  60

Glu Asp Glu Ile Asp Gly Pro Ala Gly Gln Ala Glu Pro Asp Arg Ala
 65                  70                  75                  80

His Tyr Asn Ile Val Thr Phe Cys Cys Lys Cys Asp Ser Thr Leu Arg
                 85                  90                  95

Leu Cys Val Gln Ser Thr His Val Asp Ile Arg Thr Leu Glu Asp Leu
                100                 105                 110

Leu Met Gly Thr Leu Gly Ile Val Cys Pro Ile Cys Ser Gln Pro
            115                 120                 125

<210> SEQ ID NO 8
```

```
<211> LENGTH: 90
<212> TYPE: DNA
<213> ORGANISM: Human papillomavirus

<400> SEQUENCE: 8
atggcggccc ccggcgcccg gcggccgctg ctcctgctgc tgctggcagg ccttgcacat      60
ggcgcctcag cactctttga ggatctaatc                                      90

<210> SEQ ID NO 9
<211> LENGTH: 1878
<212> TYPE: DNA
<213> ORGANISM: Mycobacterium tuberculosis

<400> SEQUENCE: 9
atggctcgtg cggtcgggat cgacctcggg accaccaact ccgtcgtctc ggttctggaa      60
ggtggcgacc cggtcgtcgt cgccaactcc gagggctcca ggaccacccc gtcaattgtc     120
gcgttcgccc gcaacggtga ggtgctggtc ggccagcccg ccaagaacca ggcagtgacc     180
aacgtcgatc gcaccgtgcg ctcggtcaag cgacacatgg gcagcgactg gtccatagag     240
attgacggca agaaatacac cgcgccggag atcagcgccc gcattctgat gaagctgaag     300
cgcgacgccg aggcctacct cggtgaggac attaccgacg cggttatcac gacgccgcc     360 tacttcaatg acgcccagcg tcaggccacc aaggacgccg ccagatcgc cggcctcaac     420 gtgctgcgga tcgtcaacga gccgaccgcg gccgcgctgg cctacggcct cgacaagggc     480
gagaaggagc agcgaatcct ggtcttcgac ttgggtggtg gcactttcga cgtttccctg     540
ctggagatcg gcgagggtgt ggttgaggtc cgtgccactt cgggtgacaa ccacctcggc     600
ggcgacgact gggaccagcg ggtcgtcgat tggctggtgg acaagttcaa gggcaccagc     660
ggcatcgatc tgaccaagga caagatggcg atgcagcggc tgcgggaagc cgccgagaag     720
gcaaagatcg agctgagttc gagtcagtcc acctcgatca acctgcccta catcaccgtc     780
gacgccgaca gaacccgtt gttcttagac gagcagctga cccgcgcgga gttccaacgg     840
atcactcagg acctgctgga ccgcactcgc aagccgttcc agtcggtgat cgctgacacc     900
ggcatttcgg tgtcggagat cgatcacgtt gtgctcgtgg gtggttcgac ccggatgccc     960
gcggtgaccg atctggtcaa ggaactcacc ggcggcaagg aacccaacaa gggcgtcaac    1020
cccgatgagg ttgtcgcggt gggagccgct ctgcaggccg cgtcctcaa gggcgaggtg    1080 aaagacgttc tgctgcttga tgttacccg ctgagcctgg gtatcgagac caagggcggg    1140
gtgatgacca ggctcatcga gcgcaacacc acgatcccca ccaagcggtc ggagactttc    1200
accaccgccg acgacaacca accgtcggtg cagatccagg tctatcaggg ggagcgtgag    1260
atcgccgcgc acaacaagtt gctcgggtcc ttcgagctga ccggcatccc gccggcgccg    1320
cgggggattc gcagatcga ggtcactttc gacatcgacg ccaacggcat tgtgcacgtc    1380
accgccaagg acaagggcac cggcaaggag aacacgatcc gaatccagga aggctcgggc    1440
ctgtccaagg aagacattga ccgcatgatc aaggacgccg aagcgcacgc cgaggaggat    1500
cgcaagcgtc gcgaggaggc cgatgttcgt aatcaagccg agacattggt ctaccagacg    1560
gagaagttcg tcaaagaaca gcgtgaggcc gagggtggtt cgaaggtacc tgaagacacg    1620
ctgaacaagg ttgatgccgc ggtggcggaa gcgaaggcgg cacttggcgg atcggatatt    1680
tcggccatca gtcggcgat ggagaagctg gccaggagt cgcaggctct ggggcaagcg    1740
atctacgaag cagctcaggc tgcgtcacag gccactggcg ctgcccaccc cggcggcgag    1800
ccgggcggtg cccaccccgg ctcggctgat gacgttgtgg acgcggaggt ggtcgacgac    1860
```

```
ggccgggagg ccaagtga                                                        1878
```

<210> SEQ ID NO 10
<211> LENGTH: 625
<212> TYPE: PRT
<213> ORGANISM: Mycobacterium tuberculosis
<400> SEQUENCE: 10

```
Met Ala Arg Ala Val Gly Ile Asp Leu Gly Thr Thr Asn Ser Val Val
1               5                   10                  15

Ser Val Leu Glu Gly Gly Asp Pro Val Val Ala Asn Ser Glu Gly
            20                  25                  30

Ser Arg Thr Thr Pro Ser Ile Val Ala Phe Ala Arg Asn Gly Glu Val
        35                  40                  45

Leu Val Gly Gln Pro Ala Lys Asn Gln Ala Val Thr Asn Val Asp Arg
    50                  55                  60

Thr Val Arg Ser Val Lys Arg His Met Gly Ser Asp Trp Ser Ile Glu
65                  70                  75                  80

Ile Asp Gly Lys Lys Tyr Thr Ala Pro Glu Ile Ser Ala Arg Ile Leu
                85                  90                  95

Met Lys Leu Lys Arg Asp Ala Glu Ala Tyr Leu Gly Glu Asp Ile Thr
            100                 105                 110

Asp Ala Val Ile Thr Thr Pro Ala Tyr Phe Asn Asp Ala Gln Arg Gln
        115                 120                 125

Ala Thr Lys Asp Ala Gly Gln Ile Ala Gly Leu Asn Val Leu Arg Ile
    130                 135                 140

Val Asn Glu Pro Thr Ala Ala Ala Leu Ala Tyr Gly Leu Asp Lys Gly
145                 150                 155                 160

Glu Lys Glu Gln Arg Ile Leu Val Phe Asp Leu Gly Gly Gly Thr Phe
                165                 170                 175

Asp Val Ser Leu Leu Glu Ile Gly Glu Gly Val Val Glu Val Arg Ala
            180                 185                 190

Thr Ser Gly Asp Asn His Leu Gly Gly Asp Asp Trp Asp Gln Arg Val
        195                 200                 205

Val Asp Trp Leu Val Asp Lys Phe Lys Gly Thr Ser Gly Ile Asp Leu
    210                 215                 220

Thr Lys Asp Lys Met Ala Met Gln Arg Leu Arg Glu Ala Ala Glu Lys
225                 230                 235                 240

Ala Lys Ile Glu Leu Ser Ser Gln Ser Thr Ser Ile Asn Leu Pro
                245                 250                 255

Tyr Ile Thr Val Asp Ala Asp Lys Asn Pro Leu Phe Leu Asp Glu Gln
            260                 265                 270

Leu Thr Arg Ala Glu Phe Gln Arg Ile Thr Gln Asp Leu Leu Asp Arg
        275                 280                 285

Thr Arg Lys Pro Phe Gln Ser Val Ile Ala Asp Thr Gly Ile Ser Val
    290                 295                 300

Ser Glu Ile Asp His Val Val Leu Val Gly Gly Ser Thr Arg Met Pro
305                 310                 315                 320

Ala Val Thr Asp Leu Val Lys Glu Leu Thr Gly Gly Lys Glu Pro Asn
                325                 330                 335

Lys Gly Val Asn Pro Asp Glu Val Val Ala Val Gly Ala Ala Leu Gln
            340                 345                 350

Ala Gly Val Leu Lys Gly Glu Val Lys Asp Val Leu Leu Leu Asp Val
        355                 360                 365
```

```
Thr Pro Leu Ser Leu Gly Ile Glu Thr Lys Gly Gly Val Met Thr Arg
    370                 375                 380

Leu Ile Glu Arg Asn Thr Thr Ile Pro Thr Lys Arg Ser Glu Thr Phe
385                 390                 395                 400

Thr Thr Ala Asp Asp Asn Gln Pro Ser Val Gln Ile Gln Val Tyr Gln
            405                 410                 415

Gly Glu Arg Glu Ile Ala Ala His Asn Lys Leu Leu Gly Ser Phe Glu
        420                 425                 430

Leu Thr Gly Ile Pro Pro Ala Pro Arg Gly Ile Pro Gln Ile Glu Val
            435                 440                 445

Thr Phe Asp Ile Asp Ala Asn Gly Ile Val His Val Thr Ala Lys Asp
    450                 455                 460

Lys Gly Thr Gly Lys Glu Asn Thr Ile Arg Ile Gln Glu Gly Ser Gly
465                 470                 475                 480

Leu Ser Lys Glu Asp Ile Asp Arg Met Ile Lys Asp Ala Glu Ala His
            485                 490                 495

Ala Glu Glu Asp Arg Lys Arg Arg Glu Ala Asp Val Arg Asn Gln
        500                 505                 510

Ala Glu Thr Leu Val Tyr Gln Thr Glu Lys Phe Val Lys Glu Gln Arg
    515                 520                 525

Glu Ala Glu Gly Gly Ser Lys Val Pro Glu Asp Thr Leu Asn Lys Val
530                 535                 540

Asp Ala Ala Val Ala Glu Ala Lys Ala Ala Leu Gly Gly Ser Asp Ile
545                 550                 555                 560

Ser Ala Ile Lys Ser Ala Met Glu Lys Leu Gly Gln Ser Gln Ala
            565                 570                 575

Leu Gly Gln Ala Ile Tyr Glu Ala Ala Gln Ala Ser Gln Ala Thr
        580                 585                 590

Gly Ala Ala His Pro Gly Gly Glu Pro Gly Gly Ala His Pro Gly Ser
            595                 600                 605

Ala Asp Asp Val Val Asp Ala Glu Val Val Asp Gly Arg Glu Ala
    610                 615                 620

Lys
625

<210> SEQ ID NO 11
<211> LENGTH: 2104
<212> TYPE: DNA
<213> ORGANISM: Artificial Sequence
<220> FEATURE:
<221> NAME/KEY: CDS
<222> LOCATION: (1)..(2103)
<220> FEATURE:
<223> OTHER INFORMATION: Description of Artificial Sequence: Synthetic
      construct

<400> SEQUENCE: 11 atg cat gga gat aca cct aca ttg cat gaa tat atg tta gat ttg caa    48
Met His Gly Asp Thr Pro Thr Leu His Glu Tyr Met Leu Asp Leu Gln
 1               5                  10                  15 cca gag aca act gat ctc tac tgt tat gag caa tta aat gac agc tca    96
Pro Glu Thr Thr Asp Leu Tyr Cys Tyr Glu Gln Leu Asn Asp Ser Ser
             20                  25                  30 gag gag gag gat gaa ata gat ggt cca gct gga caa gca gaa ccg gac   144
Glu Glu Glu Asp Glu Ile Asp Gly Pro Ala Gly Gln Ala Glu Pro Asp
         35                  40                  45 aga gcc cat tac aat att gta acc ttt tgt tgc aag tgt gac tct acg   192
Arg Ala His Tyr Asn Ile Val Thr Phe Cys Cys Lys Cys Asp Ser Thr
```

```
                Arg Ala His Tyr Asn Ile Val Thr Phe Cys Cys Lys Cys Asp Ser Thr
                 50                  55                  60 ctt cgg ttg tgc gta caa agc aca cac gta gac att cgt act ttg gaa             240
Leu Arg Leu Cys Val Gln Ser Thr His Val Asp Ile Arg Thr Leu Glu
 65                  70                  75                  80 gac ctg tta atg ggc aca cta gga att gtg tgc ccc atc tgt tct caa             288
Asp Leu Leu Met Gly Thr Leu Gly Ile Val Cys Pro Ile Cys Ser Gln
                     85                  90                  95 gga tcc atg gct cgt gcg gtc ggg atc gac ctc ggg acc acc aac tcc             336
Gly Ser Met Ala Arg Ala Val Gly Ile Asp Leu Gly Thr Thr Asn Ser
                100                 105                 110 gtc gtc tcg gtt ctg gaa ggt ggc gac ccg gtc gtc gtc gcc aac tcc             384
Val Val Ser Val Leu Glu Gly Gly Asp Pro Val Val Val Ala Asn Ser
            115                 120                 125 gag ggc tcc agg acc acc ccg tca att gtc gcg ttc gcc cgc aac ggt             432
Glu Gly Ser Arg Thr Thr Pro Ser Ile Val Ala Phe Ala Arg Asn Gly
        130                 135                 140 gag gtg ctg gtc ggc cag ccc gcc aag aac cag gca gtg acc aac gtc             480
Glu Val Leu Val Gly Gln Pro Ala Lys Asn Gln Ala Val Thr Asn Val
145                 150                 155                 160 gat cgc acc gtg cgc tcg gtc aag cga cac atg ggc agc gac tgg tcc             528
Asp Arg Thr Val Arg Ser Val Lys Arg His Met Gly Ser Asp Trp Ser
                165                 170                 175 ata gag att gac ggc aag aaa tac acc gcg ccg gag atc agc gcc cgc             576
Ile Glu Ile Asp Gly Lys Lys Tyr Thr Ala Pro Glu Ile Ser Ala Arg
                180                 185                 190 att ctg atg aag ctg aag cgc gac gcc gag gcc tac ctc ggt gag gac             624
Ile Leu Met Lys Leu Lys Arg Asp Ala Glu Ala Tyr Leu Gly Glu Asp
            195                 200                 205 att acc gac gcg gtt atc acg acg ccc gcc tac ttc aat gac gcc cag             672
Ile Thr Asp Ala Val Ile Thr Thr Pro Ala Tyr Phe Asn Asp Ala Gln
        210                 215                 220 cgt cag gcc acc aag gac gcc ggc cag atc gcc ggc ctc aac gtg ctg             720
Arg Gln Ala Thr Lys Asp Ala Gly Gln Ile Ala Gly Leu Asn Val Leu
225                 230                 235                 240 cgg atc gtc aac gag ccg acc gcg gcc gcg ctg gcc tac ggc ctc gac             768
Arg Ile Val Asn Glu Pro Thr Ala Ala Ala Leu Ala Tyr Gly Leu Asp
                245                 250                 255 aag ggc gag aag gag cag cga atc ctg gtc ttc gac ttg ggt ggt ggc             816
Lys Gly Glu Lys Glu Gln Arg Ile Leu Val Phe Asp Leu Gly Gly Gly
                260                 265                 270 act ttc gac gtt tcc ctg ctg gag atc ggc gag ggt gtg gtt gag gtc             864
Thr Phe Asp Val Ser Leu Leu Glu Ile Gly Glu Gly Val Val Glu Val
            275                 280                 285 cgt gcc act tcg ggt gac aac cac ctc ggc ggc gac gac tgg gac cag             912
Arg Ala Thr Ser Gly Asp Asn His Leu Gly Gly Asp Asp Trp Asp Gln
        290                 295                 300 cgg gtc gtc gat tgg ctg gtg gac aag ttc aag ggc acc agc ggc atc             960
Arg Val Val Asp Trp Leu Val Asp Lys Phe Lys Gly Thr Ser Gly Ile
305                 310                 315                 320 gat ctg acc aag gac aag atg gcg atg cag cgg ctg cgg gaa gcc gcc            1008
Asp Leu Thr Lys Asp Lys Met Ala Met Gln Arg Leu Arg Glu Ala Ala
                325                 330                 335 gag aag gca aag atc gag ctg agt tcg agt cag tcc acc tcg atc aac            1056
Glu Lys Ala Lys Ile Glu Leu Ser Ser Ser Gln Ser Thr Ser Ile Asn
                340                 345                 350 ctg ccc tac atc acc gtc gac gcc gac aag aac ccg ttg ttc tta gac            1104
Leu Pro Tyr Ile Thr Val Asp Ala Asp Lys Asn Pro Leu Phe Leu Asp
            355                 360                 365
```

| | |
|---|---|
| gag cag ctg acc cgc gcg gag ttc caa cgg atc act cag gac ctg ctg<br>Glu Gln Leu Thr Arg Ala Glu Phe Gln Arg Ile Thr Gln Asp Leu Leu<br>370 375 380 | 1152 |
| gac cgc act cgc aag ccg ttc cag tcg gtg atc gct gac acc ggc att<br>Asp Arg Thr Arg Lys Pro Phe Gln Ser Val Ile Ala Asp Thr Gly Ile<br>385 390 395 400 | 1200 |
| tcg gtg tcg gag atc gat cac gtt gtg ctc gtg ggt ggt tcg acc cgg<br>Ser Val Ser Glu Ile Asp His Val Val Leu Val Gly Gly Ser Thr Arg<br>405 410 415 | 1248 |
| atg ccc gcg gtg acc gat ctg gtc aag gaa ctc acc ggc ggc aag gaa<br>Met Pro Ala Val Thr Asp Leu Val Lys Glu Leu Thr Gly Gly Lys Glu<br>420 425 430 | 1296 |
| ccc aac aag ggc gtc aac ccc gat gag gtt gtc gcg gtg gga gcc gct<br>Pro Asn Lys Gly Val Asn Pro Asp Glu Val Val Ala Val Gly Ala Ala<br>435 440 445 | 1344 |
| ctg cag gcc ggc gtc ctc aag ggc gag gtg aaa gac gtt ctg ctg ctt<br>Leu Gln Ala Gly Val Leu Lys Gly Glu Val Lys Asp Val Leu Leu Leu<br>450 455 460 | 1392 |
| gat gtt acc ccg ctg agc ctg ggt atc gag acc aag ggc ggg gtg atg<br>Asp Val Thr Pro Leu Ser Leu Gly Ile Glu Thr Lys Gly Gly Val Met<br>465 470 475 480 | 1440 |
| acc agg ctc atc gag cgc aac acc acg atc ccc acc aag cgg tcg gag<br>Thr Arg Leu Ile Glu Arg Asn Thr Thr Ile Pro Thr Lys Arg Ser Glu<br>485 490 495 | 1488 |
| act ttc acc acc gcc gac gac aac caa ccg tcg gtg cag atc cag gtc<br>Thr Phe Thr Thr Ala Asp Asp Asn Gln Pro Ser Val Gln Ile Gln Val<br>500 505 510 | 1536 |
| tat cag ggg gag cgt gag atc gcc gcg cac aac aag ttg ctc ggg tcc<br>Tyr Gln Gly Glu Arg Glu Ile Ala Ala His Asn Lys Leu Leu Gly Ser<br>515 520 525 | 1584 |
| ttc gag ctg acc ggc atc ccg ccg gcg ccg cgg ggg att ccg cag atc<br>Phe Glu Leu Thr Gly Ile Pro Pro Ala Pro Arg Gly Ile Pro Gln Ile<br>530 535 540 | 1632 |
| gag gtc act ttc gac atc gac gcc aac ggc att gtg cac gtc acc gcc<br>Glu Val Thr Phe Asp Ile Asp Ala Asn Gly Ile Val His Val Thr Ala<br>545 550 555 560 | 1680 |
| aag gac aag ggc acc ggc aag gag aac acg atc cga atc cag gaa ggc<br>Lys Asp Lys Gly Thr Gly Lys Glu Asn Thr Ile Arg Ile Gln Glu Gly<br>565 570 575 | 1728 |
| tcg ggc ctg tcc aag gaa gac att gac cgc atg atc aag gac gcc gaa<br>Ser Gly Leu Ser Lys Glu Asp Ile Asp Arg Met Ile Lys Asp Ala Glu<br>580 585 590 | 1776 |
| gcg cac gcc gag gag gat cgc aag cgt cgc gag gag gcc gat gtt cgt<br>Ala His Ala Glu Glu Asp Arg Lys Arg Arg Glu Glu Ala Asp Val Arg<br>595 600 605 | 1824 |
| aat caa gcc gag aca ttg gtc tac cag acg gag aag ttc gtc aaa gaa<br>Asn Gln Ala Glu Thr Leu Val Tyr Gln Thr Glu Lys Phe Val Lys Glu<br>610 615 620 | 1872 |
| cag cgt gag gcc gag ggt ggt tcg aag gta cct gaa gac acg ctg aac<br>Gln Arg Glu Ala Glu Gly Gly Ser Lys Val Pro Glu Asp Thr Leu Asn<br>625 630 635 640 | 1920 |
| aag gtt gat gcc gcg gtg gcg gaa gcg aag gcg gca ctt ggc gga tcg<br>Lys Val Asp Ala Ala Val Ala Glu Ala Lys Ala Ala Leu Gly Gly Ser<br>645 650 655 | 1968 |
| gat att tcg gcc atc aag tcg gcg atg gag aag ctg ggc cag gag tcg<br>Asp Ile Ser Ala Ile Lys Ser Ala Met Glu Lys Leu Gly Gln Glu Ser<br>660 665 670 | 2016 |
| cag gct ctg ggg caa gcg atc tac gaa gca gct cag gct gcg tca cag<br>Gln Ala Leu Gly Gln Ala Ile Tyr Glu Ala Ala Gln Ala Ala Ser Gln<br>675 680 685 | 2064 |

-continued

```
gcc act ggc gct gcc cac ccc ggc tcg gct gat gaa agc a            2104
Ala Thr Gly Ala Ala His Pro Gly Ser Ala Asp Glu Ser
    690             695             700
```

<210> SEQ ID NO 12
<211> LENGTH: 701
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 12

```
Met His Gly Asp Thr Pro Thr Leu His Glu Tyr Met Leu Asp Leu Gln
 1               5                  10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Gly Ser Met Ala Arg Ala Val Gly Ile Asp Leu Gly Thr Thr Asn Ser
            100                 105                 110

Val Val Ser Val Leu Glu Gly Gly Asp Pro Val Val Val Ala Asn Ser
        115                 120                 125

Glu Gly Ser Arg Thr Thr Pro Ser Ile Val Ala Phe Ala Arg Asn Gly
    130                 135                 140

Glu Val Leu Val Gly Gln Pro Ala Lys Asn Gln Ala Val Thr Asn Val
145                 150                 155                 160

Asp Arg Thr Val Arg Ser Val Lys Arg His Met Gly Ser Asp Trp Ser
                165                 170                 175

Ile Glu Ile Asp Gly Lys Lys Tyr Thr Ala Pro Glu Ile Ser Ala Arg
            180                 185                 190

Ile Leu Met Lys Leu Lys Arg Asp Ala Glu Ala Tyr Leu Gly Glu Asp
        195                 200                 205

Ile Thr Asp Ala Val Ile Thr Thr Pro Ala Tyr Phe Asn Asp Ala Gln
    210                 215                 220

Arg Gln Ala Thr Lys Asp Ala Gly Gln Ile Ala Gly Leu Asn Val Leu
225                 230                 235                 240

Arg Ile Val Asn Glu Pro Thr Ala Ala Ala Leu Ala Tyr Gly Leu Asp
                245                 250                 255

Lys Gly Glu Lys Glu Gln Arg Ile Leu Val Phe Asp Leu Gly Gly Gly
            260                 265                 270

Thr Phe Asp Val Ser Leu Leu Glu Ile Gly Glu Gly Val Val Glu Val
        275                 280                 285

Arg Ala Thr Ser Gly Asp Asn His Leu Gly Gly Asp Asp Trp Asp Gln
    290                 295                 300

Arg Val Val Asp Trp Leu Val Asp Lys Phe Lys Gly Thr Ser Gly Ile
305                 310                 315                 320

Asp Leu Thr Lys Asp Lys Met Ala Met Gln Arg Leu Arg Glu Ala Ala
                325                 330                 335
```

Glu Lys Ala Lys Ile Glu Leu Ser Ser Ser Gln Ser Thr Ser Ile Asn
                340                 345                 350

Leu Pro Tyr Ile Thr Val Asp Ala Asp Lys Asn Pro Leu Phe Leu Asp
        355                 360                 365

Glu Gln Leu Thr Arg Ala Glu Phe Gln Arg Ile Thr Gln Asp Leu Leu
    370                 375                 380

Asp Arg Thr Arg Lys Pro Phe Gln Ser Val Ile Ala Asp Thr Gly Ile
385                 390                 395                 400

Ser Val Ser Glu Ile Asp His Val Val Leu Val Gly Gly Ser Thr Arg
                405                 410                 415

Met Pro Ala Val Thr Asp Leu Val Lys Glu Leu Thr Gly Gly Lys Glu
            420                 425                 430

Pro Asn Lys Gly Val Asn Pro Asp Glu Val Val Ala Val Gly Ala Ala
        435                 440                 445

Leu Gln Ala Gly Val Leu Lys Gly Glu Val Lys Asp Val Leu Leu Leu
    450                 455                 460

Asp Val Thr Pro Leu Ser Leu Gly Ile Glu Thr Lys Gly Gly Val Met
465                 470                 475                 480

Thr Arg Leu Ile Glu Arg Asn Thr Thr Ile Pro Thr Lys Arg Ser Glu
                485                 490                 495

Thr Phe Thr Thr Ala Asp Asp Asn Gln Pro Ser Val Gln Ile Gln Val
            500                 505                 510

Tyr Gln Gly Glu Arg Glu Ile Ala Ala His Asn Lys Leu Leu Gly Ser
        515                 520                 525

Phe Glu Leu Thr Gly Ile Pro Pro Ala Pro Arg Gly Ile Pro Gln Ile
    530                 535                 540

Glu Val Thr Phe Asp Ile Asp Ala Asn Gly Ile Val His Val Thr Ala
545                 550                 555                 560

Lys Asp Lys Gly Thr Gly Lys Glu Asn Thr Ile Arg Ile Gln Glu Gly
                565                 570                 575

Ser Gly Leu Ser Lys Glu Asp Ile Asp Arg Met Ile Lys Asp Ala Glu
            580                 585                 590

Ala His Ala Glu Glu Asp Arg Lys Arg Arg Glu Glu Ala Asp Val Arg
        595                 600                 605

Asn Gln Ala Glu Thr Leu Val Tyr Gln Thr Glu Lys Phe Val Lys Glu
    610                 615                 620

Gln Arg Glu Ala Glu Gly Gly Ser Lys Val Pro Glu Asp Thr Leu Asn
625                 630                 635                 640

Lys Val Asp Ala Ala Val Ala Glu Ala Lys Ala Ala Leu Gly Gly Ser
                645                 650                 655

Asp Ile Ser Ala Ile Lys Ser Ala Met Glu Lys Leu Gly Gln Glu Ser
            660                 665                 670

Gln Ala Leu Gly Gln Ala Ile Tyr Glu Ala Ala Gln Ala Ala Ser Gln
        675                 680                 685

Ala Thr Gly Ala Ala His Pro Gly Ser Ala Asp Glu Ser
    690                 695                 700

<210> SEQ ID NO 13
<211> LENGTH: 6681
<212> TYPE: DNA
<213> ORGANISM: Artificial Sequence
<220> FEATURE:
<223> OTHER INFORMATION: Description of Artificial Sequence: Synthetic
      vector

<400> SEQUENCE: 13

```
gctccgcccc cctgacgagc atcacaaaaa tcgacgctca agtcagaggt ggcgaaaccc      60
gacaggacta taaagatacc aggcgtttcc ccctggaagc tccctcgtgc gctctcctgt     120
tccgaccctg ccgcttaccg gatacctgtc cgcctttctc ccttcgggaa gcgtggcgct     180
ttctcatagc tcacgctgta ggtatctcag ttcggtgtag gtcgttcgct ccaagctggg     240
ctgtgtgcac gaaccccccg ttcagcccga ccgctgcgcc ttatccggta actatcgtct     300
tgagtccaac ccggtaagac acgacttatc gccactggca gcagccactg gtaacaggat     360
tagcagagcg aggtatgtag gcggtgctac agagttcttg aagtggtggc ctaactacgg     420
ctacactaga agaacagtat ttggtatctg cgctctgctg aagccagtta ccttcggaaa     480
aagagttggt agctcttgat ccggcaaaca aaccaccgct ggtagcggtg ttttttttgt     540
ttgcaagcag cagattacgc gcagaaaaaa aggatctcaa gaagatcctt tgatcttttc     600
tacggggtct gacgctcagt ggaacgaaaa ctcacgttaa gggattttgg tcatgagatt     660
atcaaaaagg atcttcacct agatcctttt aaattaaaaa tgaagtttta atcaatcta     720 aagtatatat gagtaaactt ggtctgacag ttaccaatgc ttaatcagtg aggcacctat     780
ctcagcgatc tgtctatttc gttcatccat agttgcctga ctcggggggg ggggcgctg     840 aggtctgcct cgtgaagaag gtgttgctga ctcataccag ggcaacgttg ttgccattgc     900
tacaggcatc gtggtgtcac gctcgtcgtt tggtatggct tcattcagct ccggttccca     960
acgatcaagg cgagttacat gatcccccat gttgtgcaaa aaagcggtta gctccttcgg    1020
tcctccgatc gttgtcagaa gtaagttggc cgcagtgtta tcactcatgg ttatggcagc    1080
actgcataat tctcttactg tcatgccatc cgtaagatgc ttttctgtga ctggtgagta    1140
ctcaaccaag tcattctgag aatagtgtat gcggcgaccg agttgctctt gcccggcgtc    1200
aatacgggat aataccgcgc cacatagcag aactttaaaa gtgctcatca ttggaaaacg    1260
ttcttcgggg cgaaaactct caaggatctt accgctgttg agatccagtt cgatgtaacc    1320
cactcgtgca cctgaatcgc cccatcatcc agccagaaag tgagggagcc acggttgatg    1380
agagctttgt tgtaggtgga ccagttggtg attttgaact tttgctttgc cacgaacgg    1440 tctgcgttgt cgggaagatg cgtgatctga tccttcaact cagcaaaagt tcgatttatt    1500
caacaaagcc gccgtcccgt caagtcagcg taatgctctg ccagtgttac aaccaattaa    1560
ccaattctga ttagaaaaac tcatcgagca tcaaatgaaa ctgcaattta ttcatatcag    1620
gattatcaat accatatttt tgaaaagcc gtttctgtaa tgaaggagaa aactcaccga    1680
ggcagttcca taggatggca agatcctggt atcggtctgc gattccgact cgtccaacat    1740
caatacaacc tattaatttc ccctcgtcaa aaataaggtt atcaagtgag aaatcaccat    1800
gagtgacgac tgaatccgt gagaatggca aaagcttatg catttctttc cagacttgtt    1860
caacaggcca gccattacgc tcgtcatcaa aatcactcgc atcaaccaaa ccgttattca    1920
ttcgtgattg cgcctgagcg agacgaaata cgcgatcgct gttaaaagga caattacaaa    1980
caggaatcga atgcaaccgg cgcaggaaca ctgccagcgc atcaacaata ttttcacctg    2040
aatcaggata ttcttctaat acctggaatg ctgttttccc ggggatcgca gtggtgagta    2100
accatgcatc atcaggagta cggataaaat gcttgatggt cggaagaggc ataaattccg    2160
tcagccagtt tagtctgacc atctcatctg taacatcatt ggcaacgcta cctttgccat    2220
gtttcagaaa caactctggc gcatcgggct tcccatacaa tcgatagatt gtcgcacctg    2280
attgcccgac attatcgcga gcccatttat acccatataa atcagcatcc atgttggaat    2340
```

```
ttaatcgcgg cctcgagcaa gacgtttccc gttgaatatg gctcataaca ccccttgtat   2400
tactgtttat gtaagcagac agttttattg ttcatgatga tatatttta tcttgtgcaa   2460 tgtaacatca gagattttga gacacaacgt ggctttcccc ccccccccat tattgaagca   2520
tttatcaggt ttattgtctc atgagcggat acatatttga atgtatttag aaaaataaac   2580 aaatagggt tccgcgcaca tttccccgaa aagtgccacc tgacgtctaa gaaaccatta   2640
ttatcatgac attaacctat aaaaataggc gtatacgag gccctttcgt ctcgcgcgtt   2700
tcggtgatga cggtgaaaac ctctgacaca tgcagctccc ggagacggtc acagcttgtc   2760
tgtaagcgga tgccgggagc agacaagccc gtcagggcgc gtcagcgggt gttggcgggt   2820 gtcgggctg gcttaactat gcggcatcag agcagattgt actgagagtg caccatatgc   2880
ggtgtgaaat accgcacaga tgcgtaagga gaaaataccg catcagattg gctattggcc   2940
attgcatacg ttgtatccat atcataatat gtacatttat attggctcat gtccaacatt   3000
accgccatgt tgacattgat tattgactag ttattaatag taatcaatta cggggtcatt   3060
agttcatagc ccatatatgg agttccgcgt tacataactt acggtaaatg gcccgcctgg   3120
ctgaccgccc aacgacccc gcccattgac gtcaataatg acgtatgttc ccatagtaac   3180
gccaataggg acttccatt gacgtcaatg ggtggagtat ttacggtaaa ctgcccactt   3240
ggcagtacat caagtgtatc atatgccaag tacgccccct attgacgtca atgacggtaa   3300
atggcccgcc tggcattatg cccagtacat gaccttatgg gactttccta cttggcagta   3360
catctacgta ttagtcatcg ctattaccat ggtgatgcgg ttttggcagt acatcaatgg   3420
gcgtggatag cggtttgact cacggggatt tccaagtctc cacccccattg acgtcaatgg   3480 gagtttgttt tggcaccaaa atcaacggga cttccaaaa tgtcgtaaca actccgcccc   3540
attgacgcaa atgggcggta ggcgtgtacg gtgggaggtc tatataagca gagctcgttt   3600
agtgaaccgt cagatcgcct ggagacgcca tccacgctgt tttgacctcc atagaagaca   3660
ccgggaccga tccagcctcc gcggccggga acggtgcatt ggaacgcgga ttccccgtgc   3720
caagagtgac gtaagtaccg cctatagact ctataggcac acccctttgg ctcttatgca   3780
tgctatactg tttttggctt ggggcctata cacccccgct tccttatgct ataggtgatg   3840
gtatagctta gcctataggt gtgggttatt gaccattatt gaccactcca acggtggagg   3900
gcagtgtagt ctgagcagta ctcgttgctg ccgcgcgcgc caccagacat aatagctgac   3960
agactaacag actgttcctt tccatgggtc ttttctgcag tcaccgtcgt cgacggtatc   4020
gataagcttg atatcgaatt cctcgacgga tcttatggcg gcccccggcg cccggcggcc   4080
gctgctcctg ctgctgctgg caggccttgc acatggcgcc tcagcactct ttgaggatct   4140
aatcatgcat ggagatacac ctacattgca tgaatatatg ttagatttgc aaccagagac   4200
aactgatctc tacggttatg ggcaattaaa tgacagctca gaggaggagg atgaaataga   4260
tggtccagct ggacaagcag aaccggacag agcccattac aatattgtaa ccttttgttg   4320
caagtgtgac tctacgcttc ggttgtgcgt acaaagcaca cacgtagaca ttcgtacttt   4380
ggaagacctg ttaatgggca cactaggaat tgtgtgcccc atctgttctc aaggatccat   4440
ggctcgtgcg gtcgggatcg acctcggac caccaactcc gtcgtctcgg ttctggaagg   4500
tggcgacccg gtcgtcgtcg ccaactccga gggctccagg accacccccgt caattgtcgc   4560 gttcgccccgc aacggtgagg tgctggtcgg ccagcccgcc aagaaccagg cggtgaccaa   4620
cgtcgatcgc accgtgcgct cggtcaagcg acacatgggc agcgactggt ccatagagat   4680
tgacggcaag aaatacaccg cgccggagat cagcgcccgc attctgatga agctgaagcg   4740
```

-continued

```
cgacgccgag gcctacctcg gtgaggacat taccgacgcg gttatcacga cgcccgccta      4800
cttcaatgac gcccagcgtc aggccaccaa ggacgccggc cagatcgccg gcctcaacgt      4860
gctgcggatc gtcaacgagc cgaccgcggc cgcgctggcc tacggcctcg acaagggcga      4920
gaaggagcag cgaatcctgg tcttcgactt gggtggtggc actttcgacg tttccctgct      4980
ggagatcggc gagggtgtgg ttgaggtccg tgccacttcg ggtgacaacc acctcggcgg      5040
cgacgactgg gaccagcggg tcgtcgattg gctggtggac aagttcaagg gcaccagcgg      5100
catcgatctg accaaggaca agatggcgat gcagcggctg cgggaagccg ccgagaaggc      5160
aaagatcgag ctgagttcga gtcagtccac ctcgatcaac ctgccctaca tcaccgtcga      5220
cgccgacaag aacccgttgt tcttagacga gcagctgacc cgcgcggagt tccaacggat      5280
cactcaggac ctgctggacc gcactcgcaa gccgttccag tcggtgatcg ctgacaccgg      5340
catttcggtg tcggagatcg atcacgttgt gctcgtgggt ggttcgaccc ggatgcccgc      5400
ggtgaccgat ctggtcaagg aactcaccgg cggcaaggaa cccaacaagg gcgtcaaccc      5460
cgatgaggtt gtcgcggtgg agccgctctg caggccggc gtcctcaagg gcgaggtgaa      5520
agacgttctg ctgcttgatg ttaccccgct gagcctgggt atcgagacca agggcggggt      5580
gatgaccagg ctcatcgagc gcaacaccac gatccccacc aagcggtcgg agactttcac      5640
caccgccgac gacaaccaac cgtcggtgca gatccaggtc tatcaggggg agcgtgagat      5700
cgccgcgcac aacaagttgc tcgggtcctt cgagctgacc ggcatcccgc cggcgccgcg      5760
ggggattccg cagatcgagg tcactttcga catcgacgcc aacggcattg tgcacgtcac      5820
cgccaaggac aagggcaccg gcaaggagaa cacgatccga atccaggaag gctcgggcct      5880
gtccaaggaa gacattgacc gcatgatcaa ggacgccgaa gcgcacgccg aggaggatcg      5940
caagcgtcgc gaggaggccg atgttcgtaa tcaagccgag acattggtct accagacgga      6000
gaagttcgtc aaagaacagc gtgaggccga gggtggttcg aaggtacctg aagcacgct      6060 gaacaaggtt gatgccgcgg tggcggaagc gaaggcggca cttggcggat cggatatttc      6120
ggccatcaag tcggcgatgg agaagctggg ccaggagtcg caggctctgg ggcaagcgat      6180
ctacgaagca gctcaggctg cgtcacaggc cactggcgct gcccacccccg gctcggctga      6240 tgaaagctta agtttaaacc gctagcctag agcggccgcg gatccagatc ttttttccctc      6300 tgccaaaaat tatggggaca tcatgaagcc ccttgagcat ctgacttctg ctaataaag     6360 gaaatttatt ttcattgcaa tagtgtgttg gaattttttg tgtctctcac tcggaaggac      6420
atatgggagg gcaaatcatt taaaacatca gaatgagtat ttggtttaga gtttggcaac      6480
atatgcccat tcttccgctt cctcgctcac tgactcgctg cgctcggtcg ttcggctgcg      6540
gcgagcggta tcagctcact caaaggcggt aatacggtta tccacagaat caggggataa      6600
cgcaggaaag aacatgtgag caaaaggcca gcaaaaggcc aggaaccgta aaaaggccgc      6660
gttgctggcg ttttttccata g                                              6681
```

<210> SEQ ID NO 14  
<211> LENGTH: 37  
<212> TYPE: DNA  
<213> ORGANISM: Artificial Sequence  
<220> FEATURE:  
<223> OTHER INFORMATION: Description of Artificial Sequence: Synthetic primer

<400> SEQUENCE: 14

```
ctgatctcta cggttatggg caattaaatg acagctc                                37
```

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gagctgtcat ttaattgccc ataaccgtag agatca                             36

<210> SEQ ID NO 16
<211> LENGTH: 9
<212> TYPE: PRT
<213> ORGANISM: Human papillomavirus

<400> SEQUENCE: 16

Arg Ala His Tyr Asn Ile Val Thr Phe
1               5

<210> SEQ ID NO 17
<211> LENGTH: 21
<212> TYPE: DNA
<213> ORGANISM: Artificial Sequence
<220> FEATURE:
<221> NAME/KEY: CDS
<222> LOCATION: (1)..(21)
<220> FEATURE:
<223> OTHER INFORMATION: Description of Artificial Sequence: Synthetic
      oligonucleotide

<400> SEQUENCE: 17 ctc tac tgt tat gag caa tta                                         21
Leu Tyr Cys Tyr Glu Gln Leu
 1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Tyr Cys Tyr Glu Gln Leu
 1               5

<210> SEQ ID NO 19
<211> LENGTH: 21
<212> TYPE: DNA
<213> ORGANISM: Artificial Sequence
<220> FEATURE:
<221> NAME/KEY: CDS
<222> LOCATION: (1)..(21)
<220> FEATURE:
<223> OTHER INFORMATION: Description of Artificial Sequence: Synthetic
      oligonucleotide

<400> SEQUENCE: 19 ctc tac ggt tat ggg caa tta                                         21
Leu Tyr Gly Tyr Gly Gln Leu
 1               5

<210> SEQ ID NO 20
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 20

Leu Tyr Gly Tyr Gly Gln Leu
 1               5
```